US012729238B2

(12) United States Patent
Steyaert et al.

(10) Patent No.: US 12,729,238 B2
(45) Date of Patent: Sep. 8, 2026

(54) NANODISC-SPECIFIC ANTIGEN-BINDING CHIMERIC PROTEINS

(71) Applicants: VIB VZW, Ghent (BE); VRIJE UNIVERSITEIT BRUSSEL, Brussels (BE); UNITED KINGDOM RESEARCH AND INNOVATION, Swindon (GB)

(72) Inventors: Jan Steyaert, Beersel (BE); Tomasz Uchanski, Luxembourg (LU); Simonas Masiulis, Utrecht (NL); Alexandru Radu Aricescu, Cambridge (GB)

(73) Assignees: United Kingdom Research and Innovation, Swindon (GB); VIB VZW, Ghent (BE); Vrije Universiteit Brussel, Brussels (BE)

( * ) Notice: Subject to any disclaimer, the term of this patent is extended or adjusted under 35 U.S.C. 154(b) by 1073 days.

(21) Appl. No.: 17/770,776

(22) PCT Filed: Oct. 21, 2020

(86) PCT No.: PCT/EP2020/079598
§ 371 (c)(1),
(2) Date: Apr. 21, 2022

(87) PCT Pub. No.: WO2021/078786
PCT Pub. Date: Apr. 29, 2021

(65) Prior Publication Data

US 2022/0380456 A1 Dec. 1, 2022

(30) Foreign Application Priority Data

Oct. 21, 2019 (EP) .................................... 19204412

(51) Int. Cl.
*C07K 16/28* (2006.01)
*C07K 14/775* (2006.01)
*C12N 15/63* (2006.01)

(52) U.S. Cl.
CPC ............ *C07K 16/28* (2013.01); *C07K 14/775* (2013.01); *C12N 15/63* (2013.01); *C07K 2317/31* (2013.01)

(58) Field of Classification Search
None
See application file for complete search history.

(56) References Cited

FOREIGN PATENT DOCUMENTS

WO 2019086548 A1 5/2019

OTHER PUBLICATIONS

Laverty, D., et al. "Cryo-EM structure of the human α1β3γ2 GABAA receptor in a lipid bilayer." Nature 565, 516-520 (2019). https://doi.org/10.1038/s41586-018-0833-4.
PCT International Search Report and Written Opinion; Application No. PCT/EP2020/079598 VIB VZW, International filing date of Oct. 21, 2020, date of mailing Jan. 25, 2021, 12 pages.
Reid, Deseree J, et al. "Engineering Nanodisc Scaffold Proteins for Native Mass Spectrometry." Analytical Chemistry (Washington), vol. 89, No. 21, 2017, pp. 11189-11192.
Uchański, Tomasz, et al. "Megabodies Expand the Nanobody Toolkit for Protein Structure Determination by Single-Particle Cryo—EM." Nature Methods, vol. 18, No. 1, 2021, pp. 60-68.
Wang, Huan, et al. "Nanobody-Based Electrochemical Immunoassay for Ultrasensitive Determination of Apolipoprotein—A1 Using Silver Nanoparticles Loaded Nanohydroxyapatite as Label." Analytical Chemistry (Washington), vol. 87, No. 22, 2015, pp. 11209-11214.

*Primary Examiner* — Ruixiang Li
(74) *Attorney, Agent, or Firm* — Patent Law Works LLP

(57) ABSTRACT

The present invention relates to the field of structural biology. More specifically, the present invention relates to an antigen-binding chimeric protein, called a MegaBody™, specifically binding a nanodisc, more specifically a membrane-scaffold protein (MSP)n which may be part of the nanodisc. The invention further provides for methods and uses of said nanodisc-specific antigen-binding chimeric proteins in three-dimensional high-resolution structural analysis of membrane proteins assembled within nanodiscs. The MSP-binding MegaBodies of the invention provide for a generic tool in membrane protein structural biology, more particular in Cryo-EM, by reducing preferred particle orientation of nanodiscs and of the entrapped target membrane proteins.

11 Claims, 14 Drawing Sheets
(12 of 14 Drawing Sheet(s) Filed in Color)
Specification includes a Sequence Listing.

ELISA

ELISA

| | Theoretical MW | Experimental MW |
|---|---|---|
| Nanodisc MSP1D1 (POPC) | 96.452 kDa | 109.9±0.02 kDa |
| $Mb_{NbF3}^{c7HopQ}$ | 54.977 kDa | 53.6±0.2 kDa |
| Nanodisc:$Mb_{NbF3}^{c7HopQ}$ complex in 1:2 ratio | 190.692 kDa | 191.9±0.03 kDa |

NANODISC-SPECIFIC ANTIGEN-BINDING CHIMERIC PROTEINS

CROSS REFERENCE TO RELATED APPLICATIONS

This application is a national phase entry under 35 U.S.C. § 371 of International Patent Application PCT/EP2020/079598, filed Oct. 21, 2020, designating the United States of America and published in English as International Patent Publication WO 2021/078786 on Apr. 29, 2021, which claims the benefit under Article 8 of the Patent Cooperation Treaty to European Patent Application Serial No. 19204412.1, filed Oct. 21, 2019, the entireties of which are hereby incorporated by reference.

FIELD OF THE INVENTION

The present invention relates to the field of structural biology. More specifically, the present invention relates to an antigen-binding chimeric protein, called a MegaBody™, specifically binding a nanodisc, more specifically a membrane-scaffold protein (MSP)n which may be part of the nanodisc. The invention further provides for methods and uses of said nanodisc-specific antigen-binding chimeric proteins in three-dimensional high-resolution structural analysis of membrane proteins assembled within nanodiscs. The MSP-binding MegaBodies of the invention provide for a generic tool in membrane protein structural biology, more particular in Cryo-EM, by reducing preferred particle orientation of nanodiscs and of the entrapped target membrane proteins.

BACKGROUND

Proteins and their complexes have critical roles in all aspects of life, but the 3D-structural analysis of many of these macromolecular components remains difficult. The preparation of diffraction quality crystals remains the major bottleneck in macromolecular X-ray crystallography. The basis for the strategy is to increase the probability of obtaining well-ordered crystals by first, minimizing the conformational heterogeneity in the target by binding to a specific conformation and second, supplementing the amount of protein surface that can facilitate primary contacts between molecules in the crystal lattice. Nanobodies® have been widely used as facilitators for structural analysis, especially for crystallography of their targets as they stabilize specific conformations[22]. Still, X-ray crystallography intrinsically holds several disadvantages, such as the prerequisite for high quality purified protein, the relatively large amounts of protein that are required, and the difficulty to obtain diffracting quality crystals of many proteins. Single particle electron cryomicroscopy (cryo-EM) has recently developed into an alternative and versatile technique for structural analysis of macromolecular complexes at atomic resolution[23]. Although instrumentation and methods for data analysis improve steadily[24], we are missing tools to analyse small size, low symmetry, and highly flexible particles to high resolution. In addition to the prerequisite homogeneity of a given sample, the highest achievable resolution of the 3D reconstruction is greatly dependent on the ability to iteratively refine the orientation parameters of each individual particle to high accuracy. Preferred particle orientation due to surface properties of the macromolecules that cause specific regions to preferentially adhere to the air-water interface or substrate support represent a recurring issue in cryo-EM. Accordingly, large molecules are relatively easy to recognize in noisy low-dose images of frozen hydrated samples, and these particles have sufficient structural features to facilitate accurate determination of their orientation parameters[25], but the process of collecting and processing images of small particles is much more difficult. To overcome these issues, Steyaert et al. (WO2019/086548A1) came to a novel solution by developing MegaBody™ technology, which consists of the use of antigen-binding chimeric proteins or MegaBodies that are composed of an antigen-binding domain, specific for the target, rigidly fused to a scaffold protein to create MegaBody chaperones that by specific binding to the target add mass, and thereby overcome the typical issues observed in structural analysis of smaller proteins.

Membrane proteins form another class of targets that show difficulties in structural analysis, especially when a native-like or membranous environment is desired. Detergents can help to keep the proteins in solution as to start structural studies, but these do not allow the typical conformational states of the membrane-bound forms. Lipid nanoparticles, liposomes, and nanodiscs have provided an elegant solution in that aspect. Lipid nanoparticles are formed by an assembly of a lipid bilayer, held together by a protein belt. The nanodisc concept is derived from high density lipoprotein (HDL) particles and their primary protein component, Apolipoprotein. The nanodisc is a synthetic non-covalent structure of phospholipid bilayer and membrane scaffold protein (MSP), a genetically engineered protein, which mimics the function of Apolipoprotein A-1 (ApoA-1). A soluble nanodisc assembles as the phospholipid forms a bilayer, which is encircled by two amphipathic MSP molecule belts that cover the hydrophobic alkyl chains of the bilayer.

The length of the MSPs controls the size of the nanodisc structure. Although this technology has successfully been used in membrane protein structure determination by different methodologies[17], cryo-EM may be the one where the advantages of nanodiscs usage is most effectively utilized[26-28], revealing improved resolution and high quality structures beyond the results obtained in other studies[29-30]. However, the use of nanodiscs in cryo-EM studies on membrane proteins also faces the issue of preferred particle orientation for these membrane proteins, which in turn again decreases the opportunities on obtaining high-resolution structures.

SUMMARY OF THE INVENTION

The present invention relates to the design and generation of novel functional antigen-binding chimeric proteins, called MegaBodies, specifically recognizing membrane scaffold proteins (MSPs) which are typically part of a nanodisc, resulting in added mass to those nanodisc particles, improving their suitability for cryo-EM, due to a reduction of the problem of preferred particle orientation of nanodiscs and of the membrane proteins of interest, present within these nanodiscs. MegaBodies or 'antigen-binding chimeric proteins' as interchangeably used herein, comprise a particular protein fusion wherein at least two connection sites within the antigen-binding domain of an immunoglobulin (Ig) domain, i.e. amino acids present in an exposed loop of the Ig fold being cleaved, are connected to another protein, also called 'scaffold protein' or 'fusion partner' protein, thereby interrupting the immunoglobulin domain topology without interfering with the Ig folding or functionality for binding the antigen. This particular fusion type has been shown to result in antigen-binding chimeric proteins that are characterized by an increased rigidity due to the fact that fusion occurs at at least 2 fusion sites, while retaining their typical fold and functionality, i.e. they retain a high affinity to bind to their antigen or target protein (Steyaert et al. WO2019/086548A1). In fact, the genetic fusions made between the antigen-binding domain and the other fusion partner protein do not disturb or alter the complementarity-determining region (CDR) structure within the Ig domain for antigen binding. The present invention concerns MegaBodies or antigen-binding chimeric proteins, as disclosed by Steyaert et al. in WO2019/086548A1, which are novel in the sense that they specifically bind the so-called Membrane Scaffold Proteins (MSPs), or variants thereof, which typically form the protein belt in nanodiscs, making these MSP-specific MegaBodies applicable as a generic fiducial aids in structural analysis of membrane proteins assembled within nanodiscs, instead of requiring target specific tools.

The first aspect of the invention relates to an antigen-binding chimeric or fusion protein comprising an antigen-binding domain that comprises an immunoglobulin (Ig) domain, which is connected to a scaffold or fusion partner protein, at one or more amino acid sites accessible in the first β-turn or loop of the IMGT® annotated Ig domain, basically via two fusions to said antigen-binding domain, resulting in an interruption of the topology of said antigen-binding domain, and wherein the antigen is a membrane scaffold protein (MSP) or MSP variant, capable of constituting a nanodisc. In a particular embodiment of the invention, the fusions can be direct fusions, or fusions made by a linker or linker peptide, said fusion sites being neatly designed to result in a rigid, non-flexible fusion protein. Preferably, the linker comprises ten, nine, eight, seven, six, five, four, three, or more preferably two, and even more preferably one amino acid residue, or is a direct fusion (no linker). The fusion sites or accessible sites involve the β-turn AB, which connects β-strand A and R-strand B of said antigen-binding immunoglobulin variable domain, as defined according to the IMGT® global reference nomenclature (Lefranc, 2014; and as presented in FIG. 2 of WO2019/086548A1). In another specific embodiment, said accessible or exposed sites are different from the antigen-binding loops or CDR loops, as to retain its functionality, i.e. its binding affinity for the nanodisc via the MSP proteins. In one embodiment, said antigen-binding chimeric protein or MegaBody comprises a fusion partner protein with a total molar mass of at least 30 kDa. In another embodiment, the fusion partner protein of the antigen-binding chimeric protein is a labelled protein. In a specific embodiment, the label is a detectable label, which allows in vivo and/or non-covalent detection or labelling of the nanodisc.

In another embodiment, the antigen-binding domain of the chimeric protein of the invention specifically binds an MSP or MSP variants in it nanodisc-bound or nanodisc-formed state. A further specific embodiment relates to the antigen-binding chimeric protein specifically binding an engineered or truncated form or the apolipoproteins (Apo) A-I, preferably the human Apo A-I, or a derivative thereof.

A further specific embodiment relates to said antigen-binding chimeric protein wherein the fusion partner protein comprises the adhesin domain of *Helicobacter pylori* HopQ or comprises the *E. coli* Glucosidase Ygjk, or comprises a variant of any of such HopQ or Ygjk proteins or protein domains, more specifically a circularly permutated variant thereof. In a more specific embodiment, the antigen-binding chimeric protein of the present invention comprises a fusion partner protein comprising the cHopQ (as depicted in SEQ ID NO: 70), c7HopQ (as depicted in SEQ ID NO:71), or the cYgjK (or Ygjk_NO, used interchangeably herein, as depicted in SEQ ID NO:51).

A further specific embodiment relates to the antigen-binding chimeric protein of the present invention selected from the group of antigen-binding chimeric proteins as depicted in SEQ ID NO: 53-67, or a homologue with at least 90% identity of any one thereof, or more specifically as depicted in SEQ ID NO: 20-33 and 52, or a homologue with at least 90% of any one thereof.

One aspect of the invention relates to an antigen-binding domain comprising an immunoglobulin single variable domain (ISVD) or a Nanobody® specifically binding the MSP1 protein, more particularly, an ISVD selected from the group of SEQ ID NOs: 37-50, or a homologue with at least 95% of any one thereof.

A further aspect of the invention relates to a nucleic acid molecule encoding any of the MSP protein-specific antigen-binding chimeric proteins or antigen-binding domains as described herein. Alternatively, in one embodiment, a chimeric gene is provided with at least a promoter, said nucleic acid molecule encoding the antigen-binding chimeric protein, and a 3' end region containing a transcription termination signal. Another embodiment relates to an expression cassette encoding said antigen-binding chimeric protein, the antigen-binding domain, or comprising the nucleic acid molecule or the chimeric gene encoding said antigen-binding chimeric protein or antigen-binding domain. Further embodiments relate to vectors comprising said expression cassette or nucleic acid molecule encoding the antigen-binding chimeric protein or antigen-binding domain of the invention. In particular embodiments, said vector is suited for recombinant expression in prokaryotic or eukaryotic cells, or for surface display in yeast, phages, bacteria, or viruses. In another embodiment, a host cell comprising the antigen-binding chimeric protein of the invention, or the antigen-binding domains described herein is disclosed. Alternatively, a host cell wherein said antigen-binding chimeric protein, or the antigen-binding domain, and the MSP protein or MSP variant are present. A further alternative is provided by the host cell wherein said antigen-binding chimeric protein, or the antigen-binding domain, and the nanodisc containing a membrane protein of interest are present.

Another aspect of the invention relates to a complex comprising said antigen-binding chimeric protein, or the antigen-binding domain of the invention, and a nanodisc, wherein said nanodisc comprises MSP or MSP variant proteins specifically bound to said antigen-binding chimeric proteins or antigen-binding domains. More particular, a complex is provided wherein said nanodisc comprises a membrane protein of interest.

Another aspect of the invention relates to a method of determining the 3-dimensional structure of a target membrane protein, contained in a nanodisc, comprising the steps of:

(i) Incubating a target membrane protein containing sample, wherein said membrane-protein is present within nanodiscs, with the antigen-binding chimeric protein or antigen-binding domain of the invention, to allow binding of the latter to the MSP protein present within said nanodisc, resulting in a complex,
(ii) displaying said complex in suitable conditions, for structural analysis, and
(iii) determining the 3D structure of said target membrane protein, present within the nanodisc at high resolution.

Specifically, said nanodisc of step i) comprises MSP or MSP variant proteins specifically bound by the antigen-binding chimeric protein or antigen-binding domain of the present invention. Preferably, said complex displayed for structural analysis comprises the nanodisc, the antigen-binding domain or antigen-binding chimeric protein bound to the MSP or MSP variants, and the membrane protein of interest (or target membrane protein), which is different from the MSP or MSP variant protein, and wherein the membrane protein of interest is being enclosed within the membrane protein-loaded nanodisc its lipid bilayer.

Another aspect relates to the use of the antigen-binding chimeric protein or the antigen-binding domain of the present invention or to the use of the nucleic acid molecule, the chimeric gene, the expression cassette, the vectors, or the complex, for structural analysis of a target membrane protein, which is not the MSP or MSP variant protein. In particular, the use of the antigen-binding chimeric protein wherein said membrane protein is present within the nanodisc, and is not bound to the antigen-binding chimeric protein or antigen-binding domain of the invention. Specifically, an embodiment relates to the use of the antigen-binding chimeric protein in structural analysis comprising single particle cryo-EM or comprising crystallography.

DESCRIPTION OF THE FIGURES

The patent or application file contains at least one drawing executed in color. Copies of this patent or patent application publication with color drawing(s) will be provided by the Office upon request and payment of the necessary fee.

The drawings described are only schematic and are non-limiting. In the drawings, the size of some of the elements may be exaggerated and not drawn on scale for illustrative purposes.

The standard method for self-assembling a membrane protein (MP) into a nanodisc is shown in route 1 (left): after detergent solubilization and purification, the target MP (green) is mixed with the membrane scaffold protein (MSP, blue) and lipids at the correct stoichiometry, followed by detergent removal through incubation with hydrophobic beads. Often, however, the MP is not stable in detergent for the extended times needed for purification. Alternatively (route 2, right), the starting membrane or tissue can be directly solubilized with excess lipid and MSP protein and rapid detergent removal, resulting in placement of the target MP (green), together with other MPs (gray) in the tissue, into the nanodisc. Subsequent purification, often with an affinity tag, is performed, and the target is stabilized in the nanodisc environment. This latter route can also be used to generate a soluble MP library that faithfully represents the MPs in the starting tissue. Adapted from Denisov et al. (ref. 17).

Figure 2A:
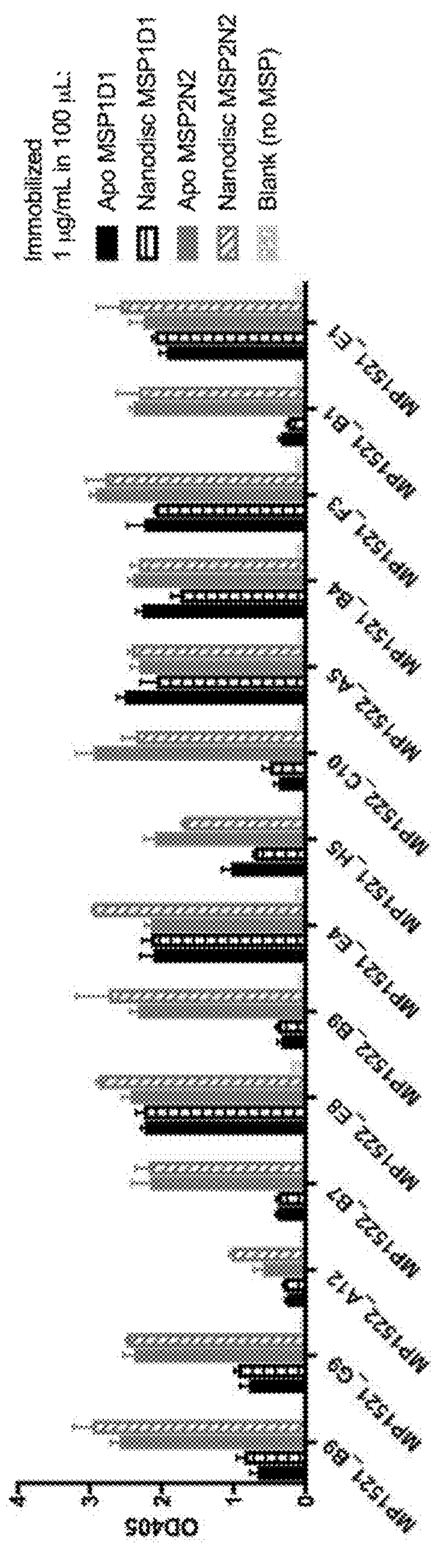
Figure 2B:
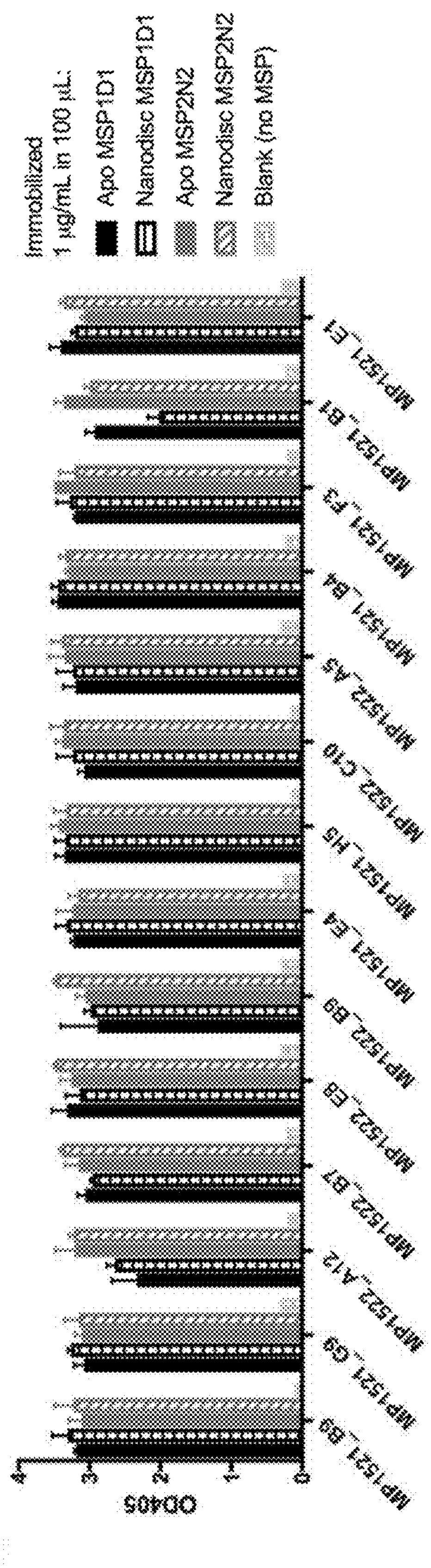

FIGS. 2A and 2B. Functional characterization of anti-MSP Nanobodies using ELISA.

Periplasmic extracts of Nanobodies (SEQ ID: 3-16) were incubated on wells coated with MSP1 D1 (SEQ ID: 1) in Apo- and Nanodisc-state, MSP2N2 (SEQ ID: 2) in Apo- and Nanodisc-state versus non-coated wells. Nanobodies were detected after 1 h (FIG. 2A) and overnight (FIG. 2B) subsequent incubation with a biotinylated CaptureSelect antibody and developed with a Streptavidin Alkaline Phosphatase conjugate. The data are shown as mean standard error of the mean (s.e.m.) of analysed in parallel triplicates n=3.

Figure 3A:
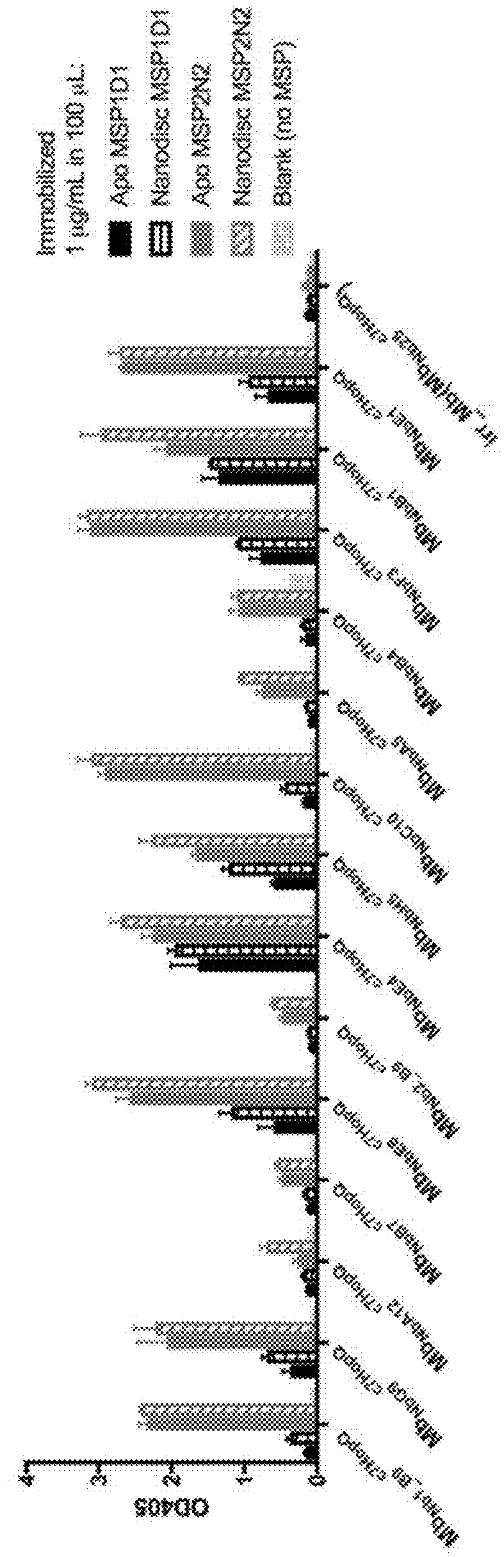
Figure 3B:
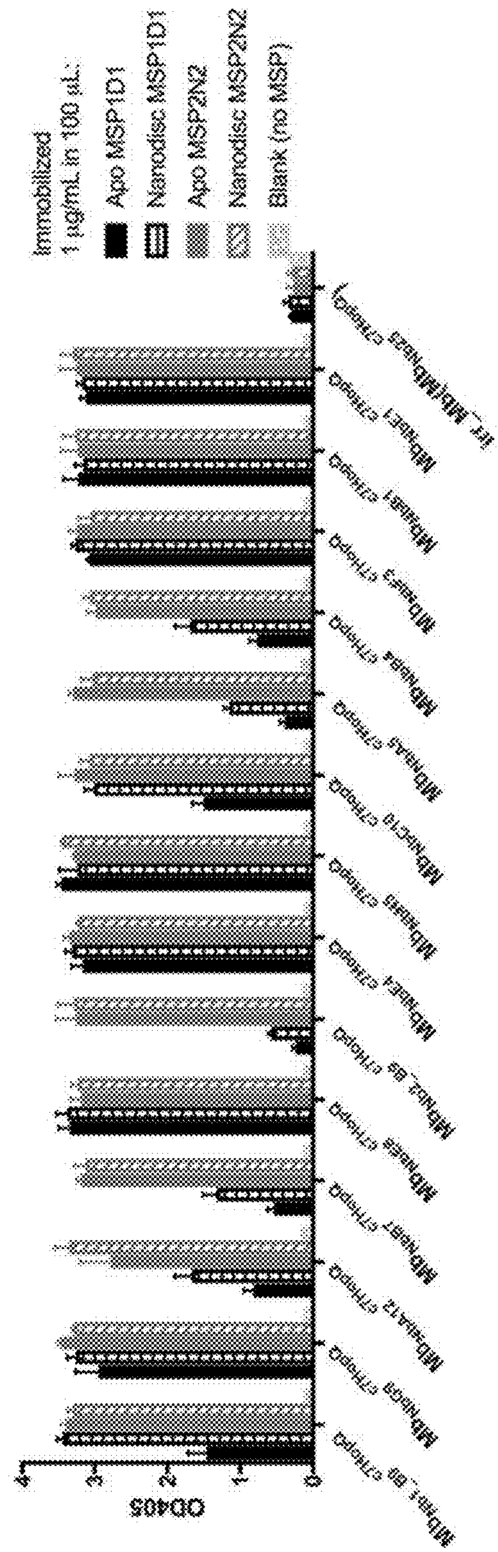

FIGS. 3A and 3B. Functional characterization of anti-MSP Megabodies using ELISA.

Gel-filtration purified Megabodies (100 μL at 200 nM concentration, SEQ ID NOs:20-33) were incubated on wells coated with MSP1 D1 (SEQ ID: 1) in Apo- and Nanodisc-state, MSP2N2 (SEQ ID: 2) in Apo- and Nanodisc-state versus non-coated wells. MegaBodies were detected after 1 h (FIG. 3A) and overnight (FIG. 3B) subsequent incubation with a biotinylated CaptureSelect antibody and developed with a Streptavidin Alkaline Phosphatase conjugate. $Mb_{Nb25}{}^{c7HopQ}$ was used as a negative control. The data are shown as mean standard error of the mean (s.e.m.) of analysed in parallel triplicates n=3.

Figure 4:
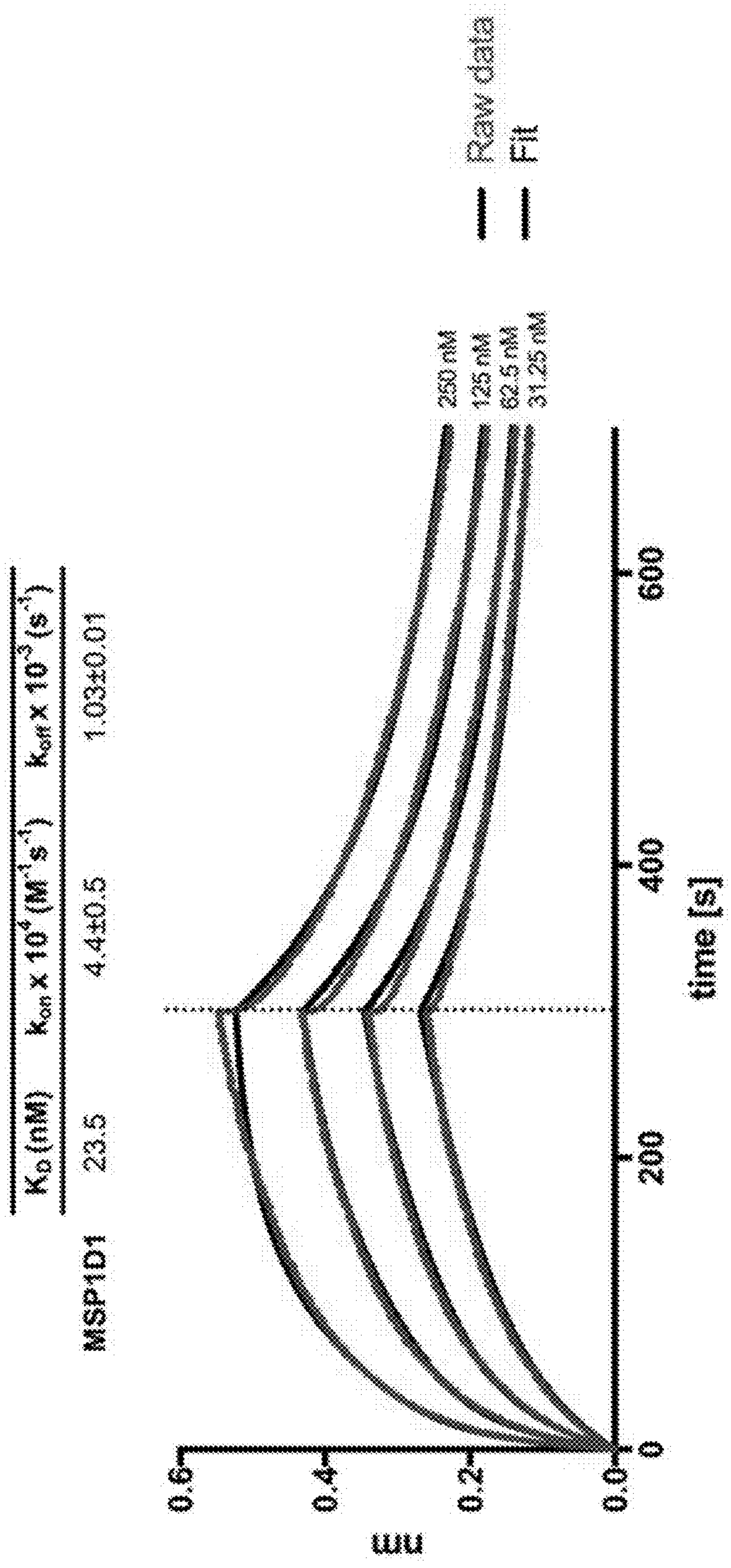

FIG. 4. Binding kinetics of $Mb_{NbF3}{}^{c7HopQ}$ to MSP1 D1.

Sensograms of the association and dissociation of $Mb_{NbF3}{}^{c7HopQ}$ onto immobilized MSP1 D1. Biotinylated MSP1 D1 was immobilized on a Streptavidin (SA) biosensor and the binding kinetics were monitored by bio-layer interferometry (BLI) on OctetRED96 (ForteBio). The measured responses (black lines) were fitted to a monophasic 1:2 binding model (red lines).

Figure 5:
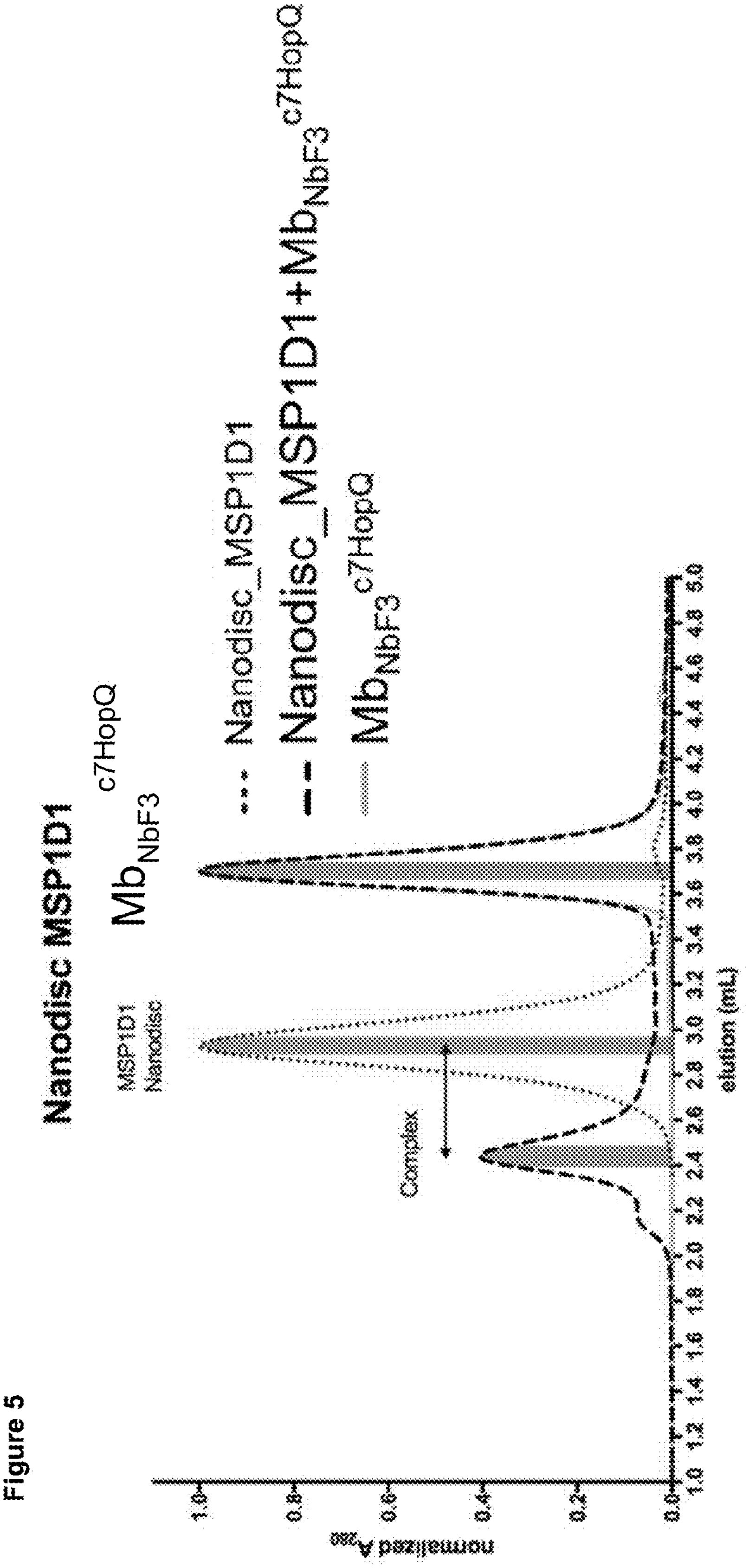

FIG. 5. Formation of a stable $Mb_{NbF3}{}^{c7HopQ}$: MSP1D1 complex.

Size exclusion experiments (SEC-3 column, HPLC) conjugated with MALS to calculate molecular weight of $Mb_{NbF3}{}^{c7HopQ}$ or MSP1 D1 POPC Nanodiscs and $Mb_{NbF3}{}^{c7HopQ}$:MSP1 D1 Nanodiscs complex. Fractions used in for calculation of molecular weight are indicated in grey.

Figure 6A:
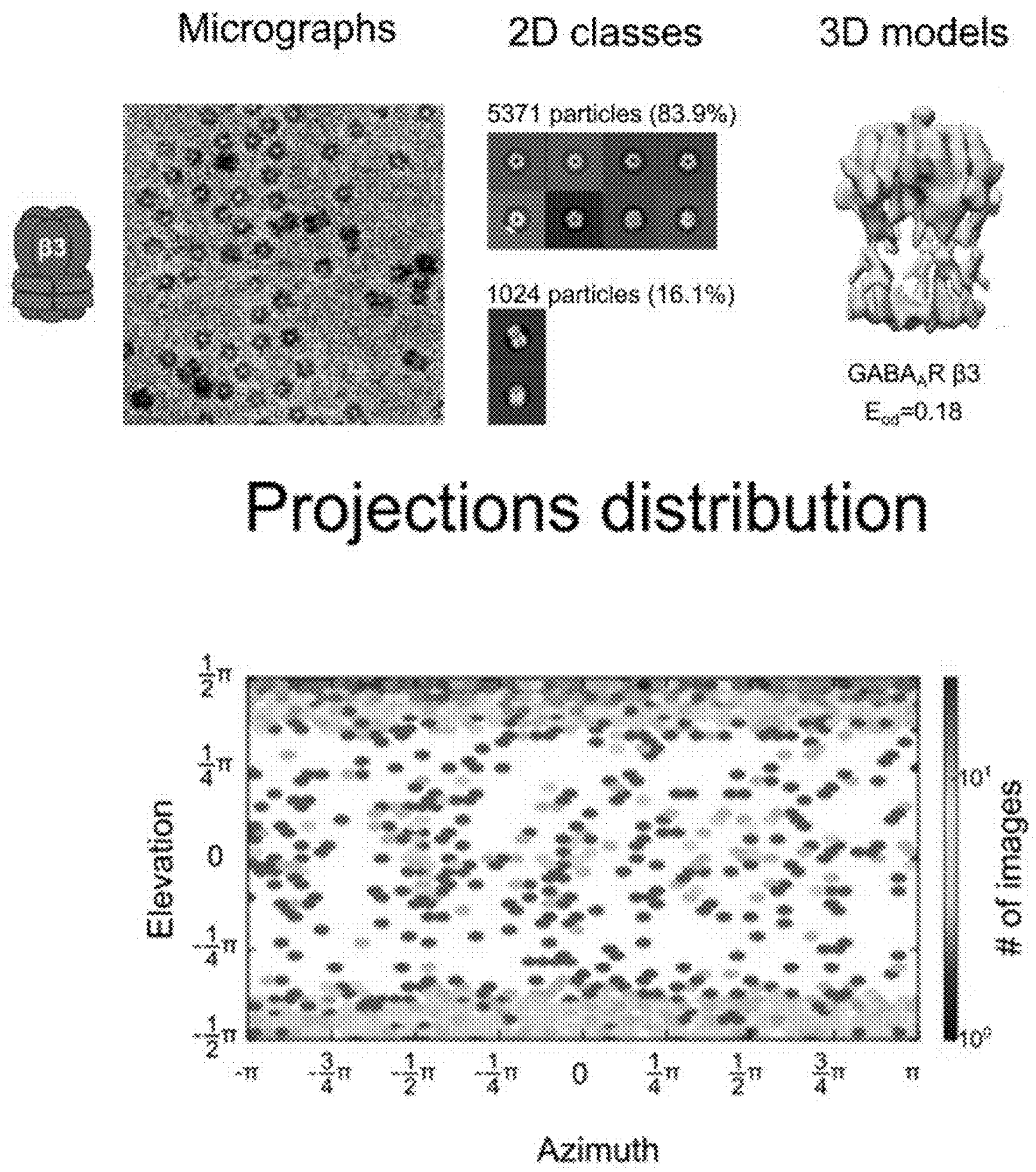
Figure 6B:
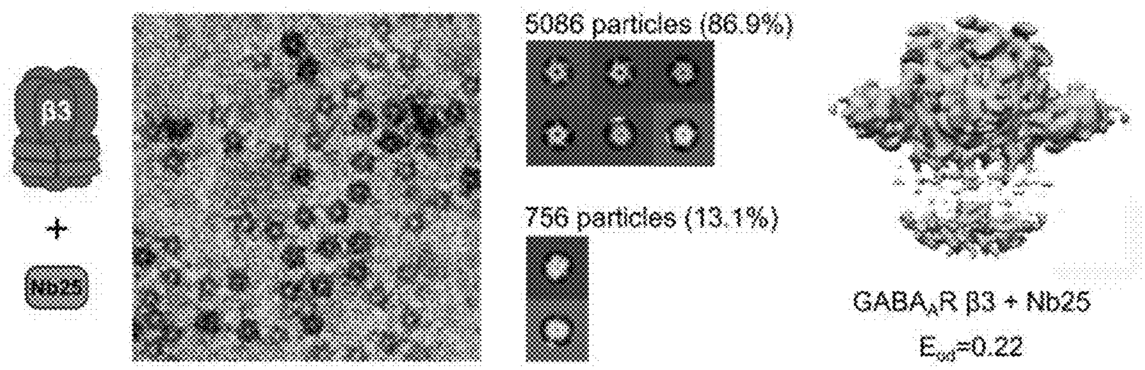
Figure 6B:
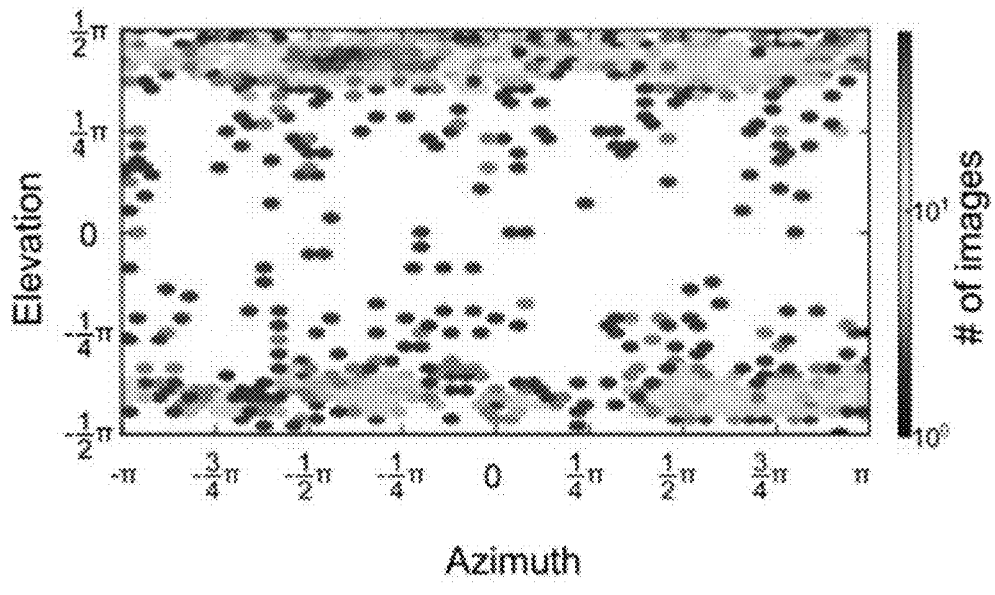
Figure 6C:
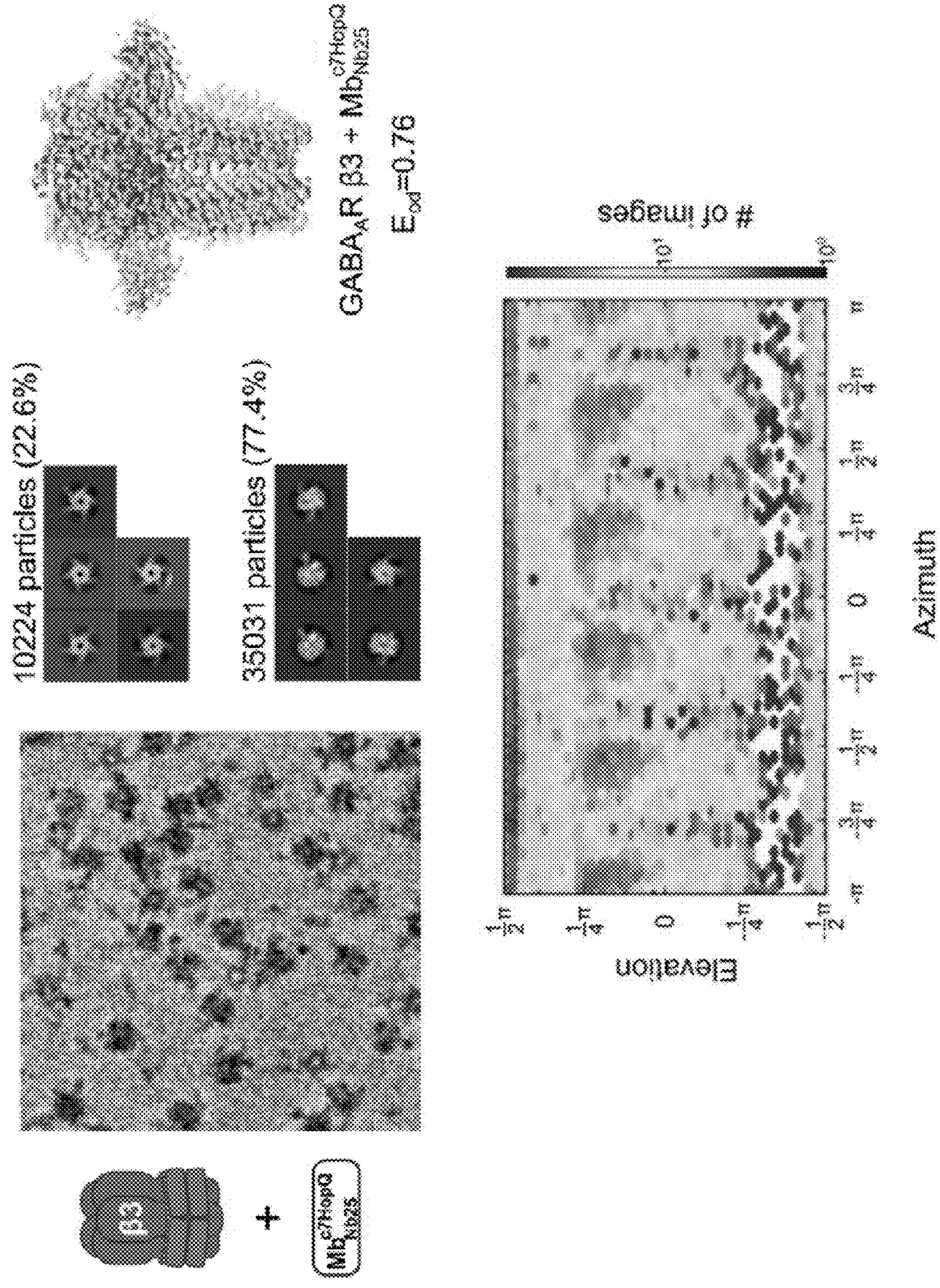

FIGS. 6A-6C. Cryo-EM datasets of the $GABA_AR$-β3: MSP2N2 Nanodisc particle alone, in complex with Nb25 or bound to MegaBody $Mb_{Nb25}{}^{c7HopQ}$, derived from Nb25 (targeting $GABA_AR$).

a-c, Direct comparison of homomeric $GABA_A$ β3 receptor reconstituted in MSP2N2 Nanodisc alone (FIG. 6A), with addition of Nb25 (FIG. 6B) and $Mb_{Nb25}{}^{c7HopQ}$ (FIG. 6C) in cryo-EM. Aligned representative micrographs and 2D classes for each experimental sample are shown in far and middle left panels, respectively. 2D classes were separated into two groups: top-view (top) and side-view (bottom). Counts of particles with a top-view or side-view orientation are indicated. Distributions of viewing directions over azimuth and elevation angles (far right panels) are calculated for shown 3D models (middle right panels).

Figure 7:
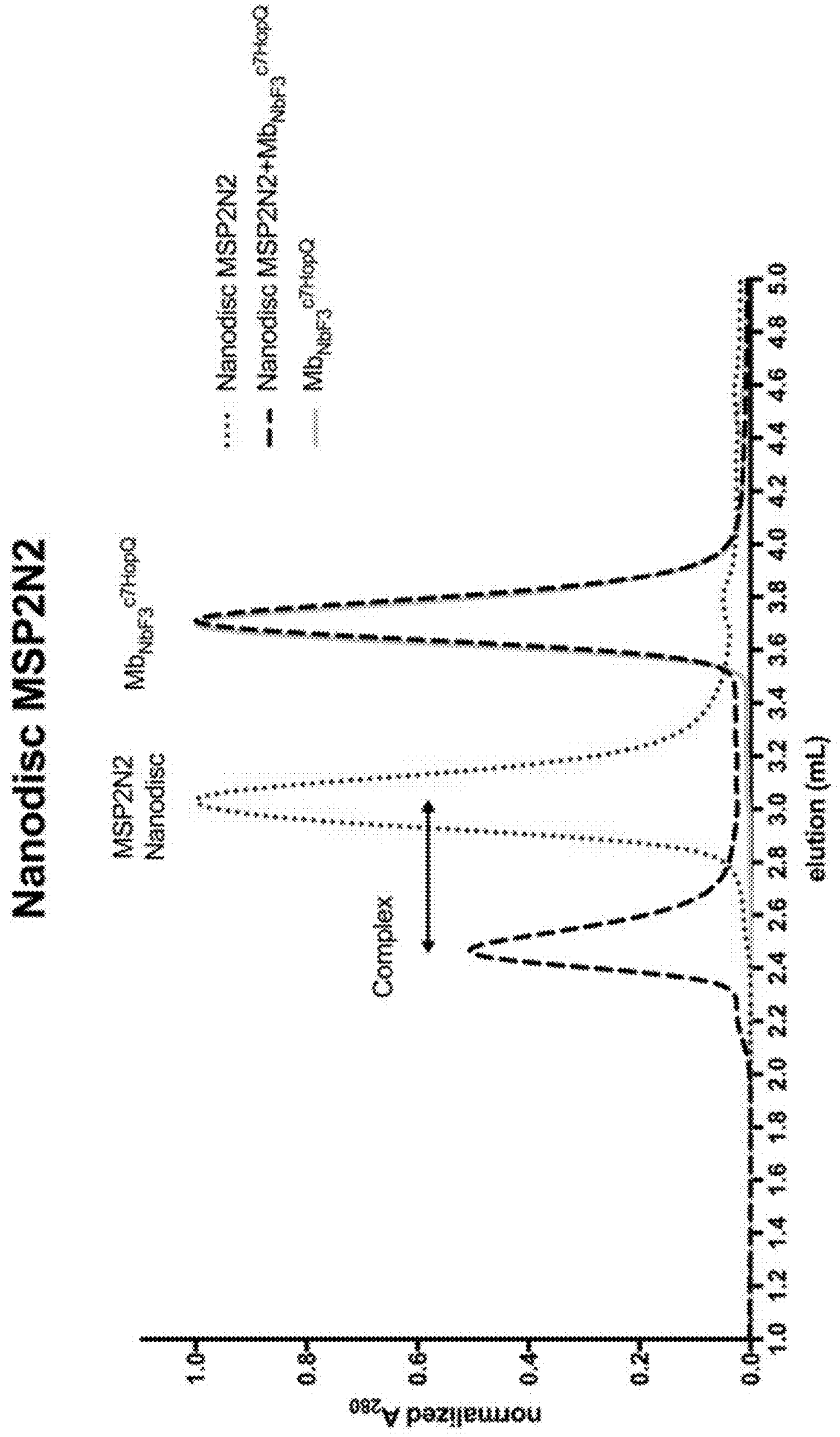

FIG. 7. Formation of a stable $Mb_{NbF3}{}^{c7HopQ}$:MSP2N2 complex. Size exclusion profiles (SEC-3 column, HPLC) of $Mb_{NbF3}{}^{c7HopQ}$, MSP2N2 Nanodiscs and a $Mb_{NbF3}{}^{c7HopQ}$: MSP2N2 Nanodiscs complex.

FIGS. 8A-8F. Cryo-EM datasets of the $GABA_AR$-β3: MSP2N2 Nanodisc particle in complex with anti-Nanodisc $Mb_{NbF3}{}^{c7HopQ}$ MegaBody.

Figure 8A:
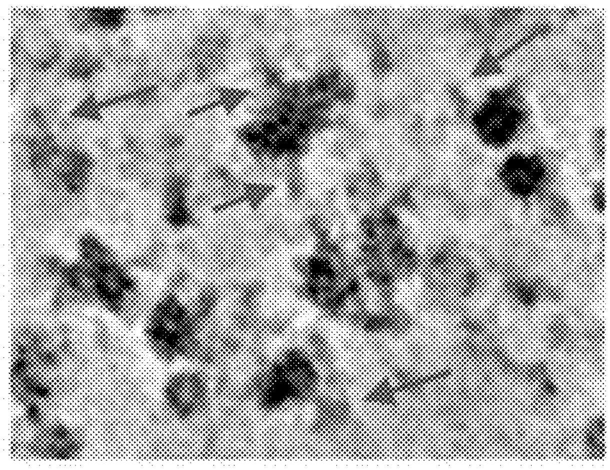
Figure 8B:
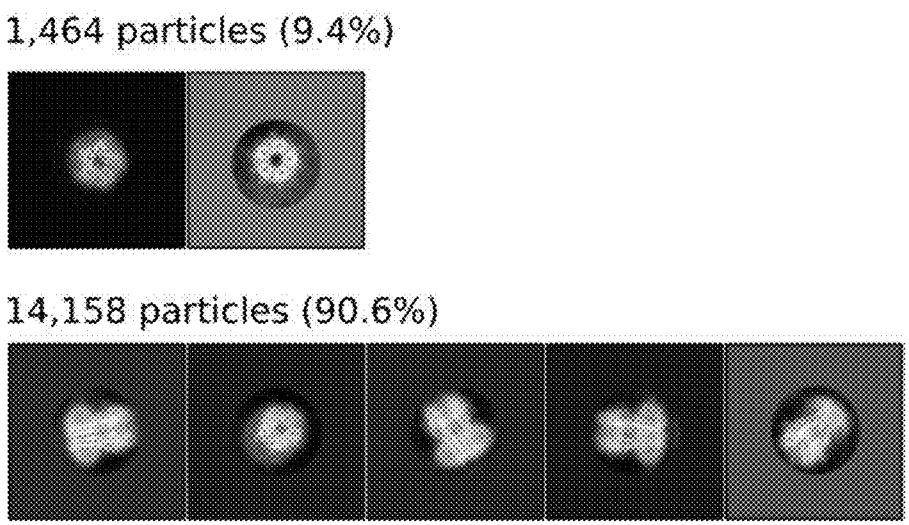
Figure 8C:
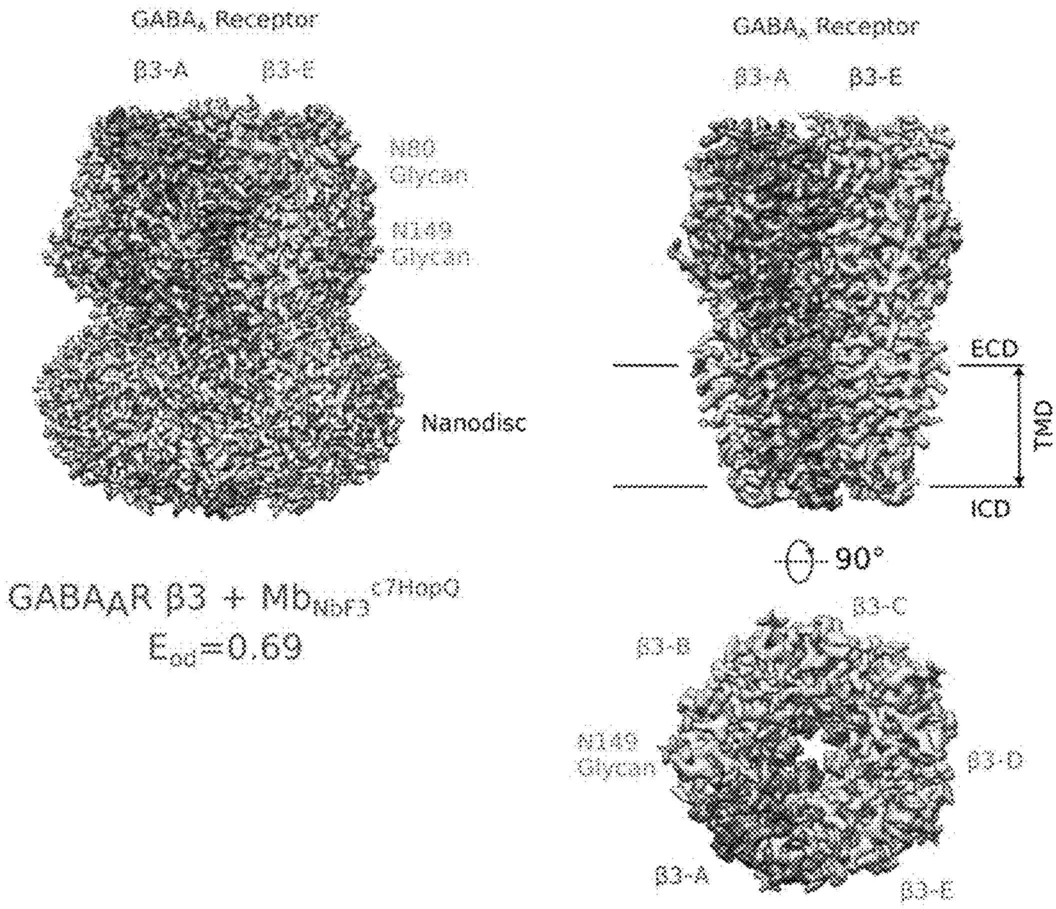

FIGS. 8A-8C, Aligned and motion-corrected cryo-EM micrograph (FIG. 8A), 2D classes (FIG. 8B) and generated 3D model (FIG. 8C) of $GABA_AR$-β3:MSP2N2 Nanodisc particle in complex with anti-Nanodisc $Mb_{NbF3}{}^{c7HopQ}$. (FIG. 8B) 2D classes were separated into two groups: top-view (top) and side-view (bottom).

Figure 8D:
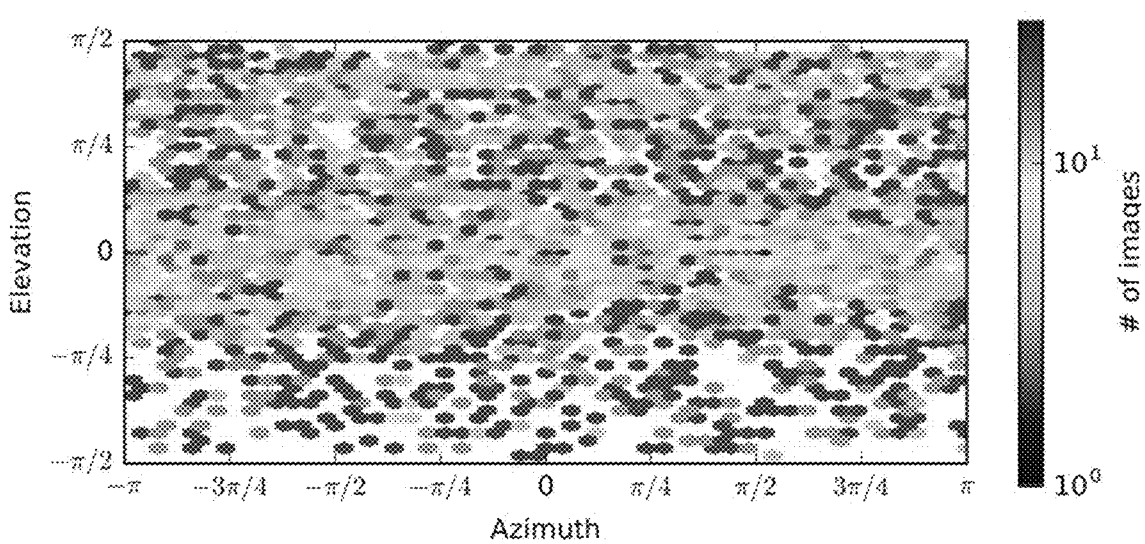
Figure 8E:
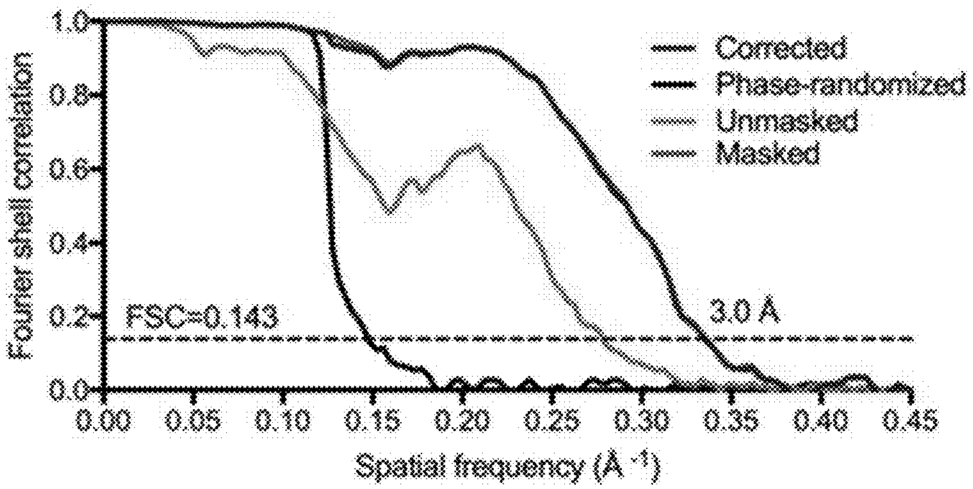

Counts of particles with a top-view or side-view orientation are indicated. FIGS. 8D and 8E, Distributions of viewing directions over azimuth and elevation angles (FIG. 8D) and FSC curves of the using gold-standard refinement (FIG. 8E) are calculated for the 3D model from FIG. 8C. (FIG. 8F) HPLC analysis of complex formation between homopentameric $GABA_AR$ β3 and megabody $Mb_{NbF3}^{c7HopQ}$.

Superposition of gel filtration profiles (Superose Increase 6 3.2/300 column) of β3 $GABA_AR$ reconstituted in MSP2N2 nanodisc alone (blue line) and preincubated with $Mb_{NbF3}^{c7HopQ}$ 1:3 molar ratio (red line).

Figure 9A:
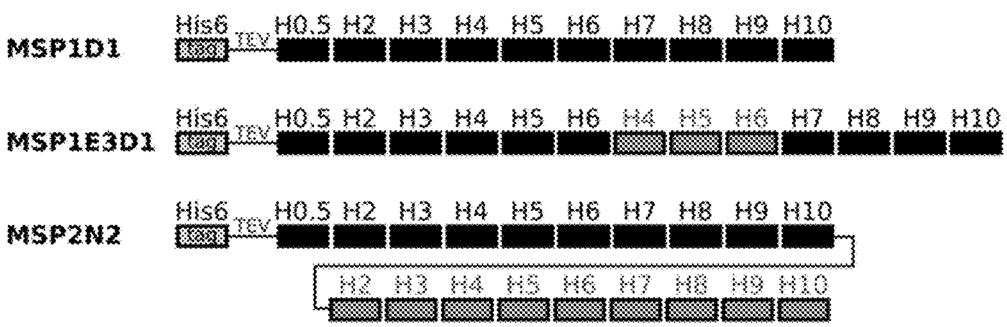
Figure 9B:
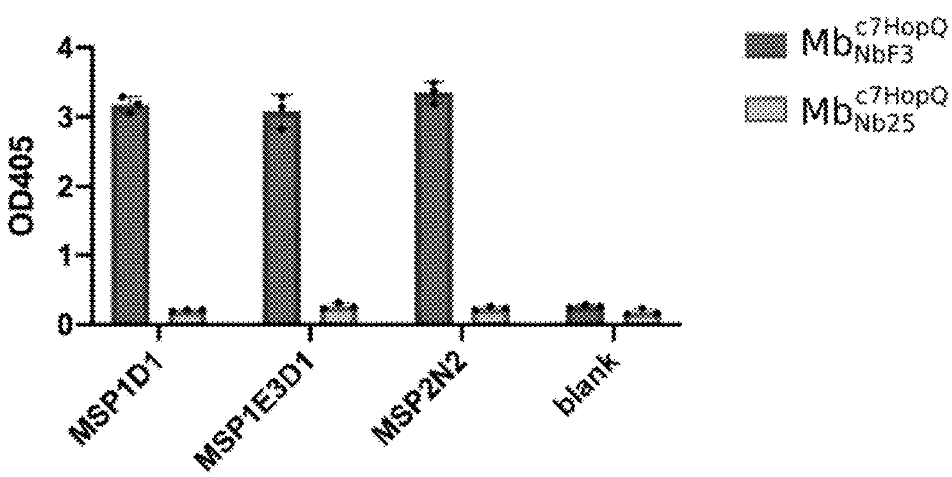

FIGS. 9A and 9B.

$Mb_{NbF3}^{c7HopQ}$, an MSP-specific megabody binding to recombinant MSP variants.

FIG. 9A, Recombinant MSP variants used to assemble nanodiscs: the His6-tag, the TEV cleavage site and the α-helical domains (H) are shown. FIG. 9B. Specific binding of $Mb_{NbF3}^{c7HopQ}$ (SEQ ID NO:31) to different MSP variants analysed by ELISA.

$Mb_{Nb25}^{c7HopQ}$ (SEQ ID NO:34), a megabody that binds $GABA_AR$ was used as a negative control. The data are shown as mean standard error of analysed in parallel triplicates n=3.

Figure 10A:
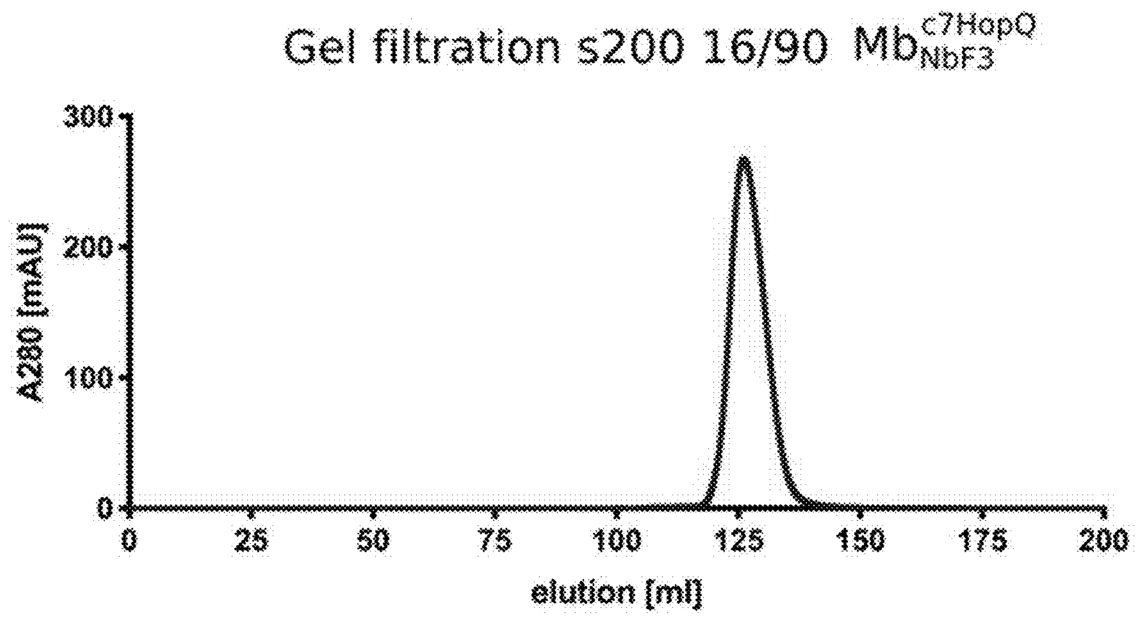
Figure 10B:
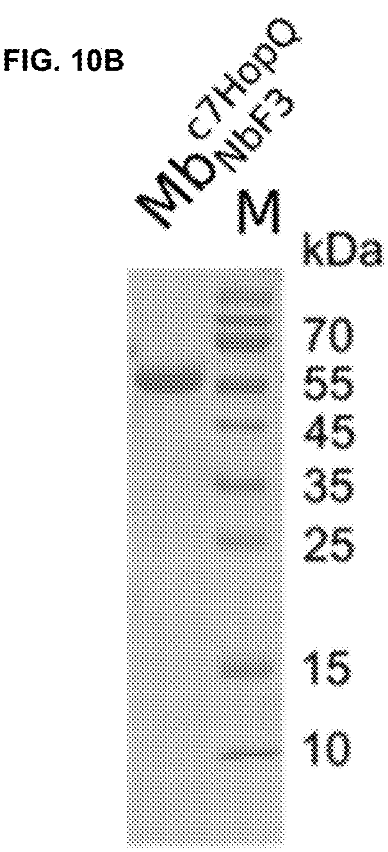

FIGS. 10A and 10B. Production and characterization of megabody $Mb_{NbF3}^{c7HopQ}$.

FIG. 10A, Size exclusion profile of $Mb_{NbF3}^{c7HopQ}$ purified from the periplasm of *E. coli* by Ni-NTA affinity chromatography and size exclusion. FIG. 10B, SDS-PAGE analysis (4-20%) of purified megabody $Mb_{NbF3}^{c7HopQ}$.

DETAILED DESCRIPTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases 'in one embodiment' or 'in an embodiment' in various places throughout this specification are not necessarily all referring to the same embodiment but may.

Definitions

Where an indefinite or definite article is used when referring to a singular noun e.g. 'a' or 'an', 'the', this includes a plural of that noun unless something else is specifically stated. Where the term 'comprising' is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $4^{th}$ ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

'Nucleotide sequence', "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like. "Coding sequence" is a nucleotide sequence, which is transcribed into mRNA and/or translated into a polypeptide when placed under the control of appropriate regulatory sequences. The boundaries of the coding sequence are determined by a translation start codon at the 5-terminus and a translation stop codon at the 3'-terminus. A coding sequence can include, but is not limited to mRNA, cDNA, recombinant nucleotide sequences or genomic DNA, while introns may be present as well under certain circumstances. With a "chimeric gene" or "chimeric construct" or "chimeric gene construct" is meant a recombinant nucleic acid sequence in which a promoter or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence. The regulatory nucleic acid sequence of the chimeric gene is not operatively linked to the associated nucleic acid sequence as found in nature. An "expression cassette" comprises any nucleic acid construct capable of directing the expression of a gene/coding sequence of interest, which is operably linked to a promoter of the expression cassette. Expression cassettes are generally DNA constructs preferably including (5' to 3' in the direction of transcription): a promoter region, a polynucleotide sequence, homologue, variant or fragment thereof operably linked with the transcription initiation region, and a termination sequence including a stop signal for RNA polymerase and a polyadenylation signal. It is understood that all of these regions should be capable of operating in biological cells, such as prokaryotic or eukaryotic cells, to be transformed. The promoter region comprising the transcription initiation region, which preferably includes the RNA polymerase binding site, and the polyadenylation signal may be native to the biological cell to be transformed or may be derived from an alternative source, where the region is functional in the biological cell. Such cassettes can be constructed into a "vector".

The terms "protein", "polypeptide", and "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes posttranslational modifications of the polypeptide, such as glycosylation, phosphorylation and acetylation. Based on the amino acid sequence and the modifications, the atomic or molecular mass or weight of a polypeptide is expressed in (kilo)dalton (kDa). By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation. By "isolated" is meant material that is substantially or essentially free from components that normally accompany it in its native state. For example, an "isolated polypeptide" refers to a polypeptide which has been purified from the molecules which flank it in a naturally-occurring state, e.g., an antigen-binding chimeric protein which has been removed from the molecules present in the production host that are adjacent to said polypeptide, or an "isolated nanodisc complex" referring to a nanodisc containing a membrane protein of interest, and optionally an antigen-binding chimeric protein bound to said nanodisc, which is as a complex purified from the molecules present within a cell, extract, or mixture. An isolated chimer can be generated by amino acid chemical synthesis or can be generated by recombinant production. The expression "heterologous protein" may mean that the protein is not derived from the same species or strain that is used to display or express the protein.

"Homologue", "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met, also indicated in one-letter code herein) occurs in both sequences to yield the number of matched positions, dividing the number of matched positions by the total number of positions in the window of comparison (i.e., the window size), and multiplying the result by 100 to yield the percentage of sequence identity. A "substitution", or "mutation" as used herein, results from the replacement of one or more amino acids or nucleotides by different amino acids or nucleotides, respectively as compared to an amino acid sequence or nucleotide sequence of a parental protein or a fragment thereof. A protein variant may constitute a mutant variant, or contain several substitutions of mutations. It is understood that a protein or a fragment thereof may have conservative amino acid substitutions which have substantially no effect on the protein's activity.

A "protein domain" is a distinct functional and/or structural unit in a protein. Usually a protein domain is responsible for a particular function or interaction, contributing to the overall role of a protein. Domains may exist in a variety of biological contexts, where similar domains can be found in proteins with different functions. Protein secondary structure elements (SSEs) typically spontaneously form as an intermediate before the protein folds into its three dimensional tertiary structure. The two most common secondary structural elements of proteins are alpha helices and beta (β) sheets, though R-turns and omega loops occur as well. Beta sheets consist of beta strands (also β-strand) connected laterally by at least two or three back-bone hydrogen bonds, forming a generally twisted, pleated sheet. A β-strand is a stretch of poly-peptide chain typically 3 to 10 amino acids long with backbone in an extended conformation. A β-turn is a type of non-regular secondary structure in proteins that causes a change in direction of the polypeptide chain. Beta turns (β turns, β-turns, β-bends, tight turns, reverse turns) are very common motifs in proteins and polypeptides, which mainly serve to connect β-strands. For the IMGT© definition of β-turn, as present in a variable domain, see also Lefranc (2014) and Steyaert et al. (WO2019/086548A1, FIG. 25). 3-turns typically consist of four amino acid residues (labelled i, +1, i+2 and +3), and are defined in two ways: or by the possession of an intra-main-chain hydrogen bond between the CO of residue i and the NH of residue i+3; or alternatively, by having a distance of less than 7 Å between the Ca atoms of residues i and +3. The hydrogen bond criterion is the one most appropriate for everyday use, partly because it gives rise to four distinct categories.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified", "mutant", "engineered" or "variant" refers to a gene or gene product that displays modifications in sequence, post-translational modifications and/or functional properties (i.e., altered characteristics) when compared to the wild-type gene or gene product. It is noted that naturally occurring mutants can be isolated; these are identified by the fact that they have altered characteristics when compared to the wild-type gene or gene product.

The term "fused to", as used herein, and interchangeably used herein as "connected to", "conjugated to", "ligated to" refers, in particular, to "genetic fusion", e.g., by recombinant DNA technology, as well as to "chemical and/or enzymatic conjugation" resulting in a stable covalent link. The same applies for the term "inserted in", wherein one nucleic acid or protein sequence part may be inserted in another sequence by fusing the two sequences genetically, enzymatically or chemically.

The terms "chimeric polypeptide", "chimeric protein", "chimer", "fusion polypeptide", "fusion protein", or "non-naturally-occurring protein" are used interchangeably herein and refer to a protein that comprises at least two separate and distinct polypeptide components that may or may not originate from the same protein. The term also refers to a non-naturally occurring molecule which means that it is man-made. The term "fused to", and other grammatical equivalents, such as "covalently linked", "connected", "attached", "ligated", "conjugated" when referring to a chimeric polypeptide (as defined herein) refers to any chemical or recombinant mechanism for linking two or more polypeptide components. The fusion of the two or more polypeptide components may be a direct fusion of the sequences or it may be an indirect fusion, e.g. with intervening amino acid sequences or linker sequences, or chemical linkers. The fusion of two polypeptides or of an antigen-binding domain and a scaffold protein, as described herein, may also refer to a non-covalent fusion obtained by chemical linking.

"Binding" means any interaction, be it direct or indirect. A direct interaction implies a contact between the binding partners. An indirect interaction means any interaction whereby the interaction partners interact in a complex of more than two molecules. The interaction can be completely indirect, with the help of one or more bridging molecules, or partly indirect, where there is still a direct contact between the partners, which is stabilized by the additional interaction of one or more molecules. By the term "specifically binds," as used herein with respect to an antigen-binding, immunoglobulin, immunoglobulin-like domain or antibody domain, is meant a binding domain which recognizes a specific antigen, but does not substantially recognize or bind other molecules in a sample, and is also referred to as an "antigen-binding domain" or "antigen-binding protein". For example, an antibody that specifically binds to an antigen from one species may also bind to that antigen from one or more species, or to variants of the antigen. But, such cross-species reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g. an antigenic determinant or epitope) on the chemical species; for example, an antigen-binding protein recognizes and binds to a specific protein structure rather than to proteins generally. If an antigen-binding protein is specific for epitope "A", the presence of a molecule containing epitope A (or free, unlabeled A), in a reaction containing labeled "A" and the antigen-binding protein, will reduce the amount of labeled A bound to the antigen-binding protein. The term "specificity", as used herein, refers to the ability of a binding domain, in particular an antigen-binding domain, immunoglobulin, or immunoglobulin-like domain, or an immunoglobulin fragment, such as a VHH or Nanobody, to bind preferentially to one antigen, versus a different antigen, and does not necessarily imply high affinity. An "epitope", as used herein, refers to an antigenic determinant of a polypeptide. An epitope could comprise 3 amino acids in a spatial conformation, which is unique to the epitope. Generally, an epitope consists of at least 4, 5, 6, 7 such amino acids, and more usually, consists of at least 8, 9, 10 such amino acids. Methods of determining the spatial conformation of amino acids are known in the art, and include, for example, X-ray crystallography and multi-dimensional nuclear magnetic resonance. A "conformational epitope", as used herein, refers to an epitope comprising amino acids in a spatial conformation that is unique to a folded 3-dimensional conformation of a polypeptide. Generally, a conformational epitope consists of amino acids that are discontinuous in the linear sequence but that come together in the folded structure of the protein. However, a conformational epitope may also consist of a linear sequence of amino acids that adopts a conformation that is unique to a folded 3-dimensional conformation of the polypeptide (and not present in a denatured state). The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological. Macromolecules, W.H. Freeman and Company, 1980, and Creighton, Proteins: Structures and Molecular Properties, W.H. Freeman and Company, 1993.

The term "affinity", as used herein, generally refers to the degree to which a ligand (as defined further herein) binds to a target protein so as to shift the equilibrium of target protein and ligand toward the presence of a complex formed by their binding. Thus, for example, where an antigen-binding chimeric polypeptide and a ligand are combined in relatively equal concentration, a ligand of high affinity will bind to the antigen-binding chimeric polypeptide so as to shift the equilibrium toward high concentration of the resulting complex. The dissociation constant Kd is commonly used to describe the affinity between a ligand and a target protein. Typically, the dissociation constant has a value that is lower than $10^{-5}$ M. Preferably, the dissociation constant is lower than $10^{-6}$ M, more preferably, lower than $10^{-7}$ M. Most preferably, the dissociation constant is lower than $10^{-8}$ M. Other ways of describing the affinity between a ligand and its target protein are the association constant (Ka), the inhibition constant (Ki), or indirectly by evaluating the potency of ligands by measuring the half maximal inhibitory concentration ($IC_{50}$) or half maximal effective concentration ($EC_{50}$). It will be appreciated that within the scope of the present invention, the term "affinity" is used in the context of the antigen-binding chimeric protein comprising the Ig domain that binds a (conformational) epitope of the target protein, more particularly the antigen-binding chimeric protein Ig domain retaining its "functionality" to bind its target via the CDR regions of said Ig domain. Accordingly, as used herein, the term "functional antigen-binding protein" or "conformation-selective antigen-binding domain" in the context of the present invention refers to an Ig domain of said chimeric antigen-binding protein that is functional in binding to its target protein, more specifically the nanodisc belt protein, optionally in a conformation-selective manner, which may be a nanodisc-bound or nanodisc-free (apo)state, or both. The terms "specifically bind", "selectively bind", "preferentially bind", and grammatical equivalents thereof, are used interchangeably herein. The terms "conformational specific" or "conformational selective" are also used interchangeably herein.

The term "antibody" as used herein, refers to an immunoglobulin (Ig) molecule or a molecule comprising an immunoglobulin (Ig) domain, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The term "immunoglobulin (Ig) domain" as used herein refers to a globular region of an antibody chain, or to a polypeptide that essentially consists of such a globular region. Immunoglobulin domains are characterized in that they retain the immunoglobulin fold (Ig fold as named herein) characteristic of antibody molecules, which consists of a two-layer sandwich of about seven to nine antiparallel β-strands arranged in two β-sheets, optionally stabilized by a conserved disulphide bond. The term "immunoglobulin (Ig) domain", includes "immunoglobulin constant domain", and "immunoglobulin variable domain" (abbreviated as "IVD"), wherein the latter means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) (IVDs) that confer specificity to an antibody for the antigen by carrying the antigen-binding site. According to IMGT classification, an immunoglobulin variable domain or V-domain comprises about 100 AA and is made of nine anti-parallel beta-strands (A,B,C,C', C", D, E, F, and G) linked by pi-turns (AB,CC', C"D, DE, and EF), and three loops (or CDRs) (BC, C'C", and FG), forming a sandwich of two sheets [ABED][GFCC'C" ](see WO2019/086548A1 FIG. 25, adapted from Lefranc, 2014). The sheets are closely packed against each other through hydrophobic interactions giving a hydrophobic core, and joined together by a disulfide bridge between a first highly conserved cysteine (1st-Cys) in D3-strand B (in the first sheet) and a second equally conserved cysteine (2nd-Cys) in β-strand F (in the second sheet). The unique numbering of the IMGT® definitive system, as used in the present invention, provides CDR-IMGT accurately and unambiguously delimitated in contrast to the CDR described in the literature. For alternative numbering, also see e.g. Kabat (Kabat et al., 1991) or Chothia (Chothia and Lesk, 1987). For a V-domain, the CDR1-IMGT encompasses positions 27-38, the CDR2-IMGT positions 56-65, and the CDR3-IMGT positions 105-117 (Lefranc, 2014). An "exposed region" or "exposed loop" of the Ig domain of the invention, refers to a region or polypeptide chain that is exposed at the surface of the protein. For the Ig domain, said exposed region or loop is preferably a β-turn, and most preferably a β-turn as defined by Lefranc (2014). Although the CDRs are also considered "loops" according to the IMGT definition, those are not considered as preferred candidates for "exposed regions" of the invention, with accessible sites for fusion of the scaffold, since this would most likely lead to the destruction of antigen-binding, and therefore not allow to obtain functional antigen-binding chimeric proteins.

An "immunoglobulin domain" of this invention also includes "immunoglobulin single variable domains" (abbreviated as "ISVD"), equivalent to the term "single variable domains", and defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen. In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs. As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit). In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody. For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH); other single variable domains, or any suitable fragment of any one thereof. In particular, the immunoglobulin single variable domain may be a Nanobody (as defined herein) or a suitable fragment thereof. Note:Nanobody®, Nanobodies® and Nanoclone® are registered trademarks of Ablynx N.V. For a general description of Nanobodies, reference is made to the further description below, as well as to the prior art cited herein, such as e.g. described in WO2008/020079.

Immunoglobulin domains herein also include "VHH domains", also known as VHHs, VHH domains, VHH antibody fragments, and VHH antibodies, have originally been described as the antigen-binding immunoglobulin (Ig) (variable) domain of "heavy chain antibodies" (i.e., of "antibodies devoid of light chains"; Hamers-Casterman et al (1993) Nature 363: 446-448). The term "VHH domain" has been chosen to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHHs and Nanobody, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As described in these references, Nanobody (in particular VHH sequences and partially humanized Nanobody) can in particular be characterized by the presence of one or more "Hallmark residues" in one or more of the framework sequences. A further description of the Nanobody, including humanization and/or camelization of Nanobody, as well as other modifications, parts or fragments, derivatives or "Nanobody fusions", multivalent constructs (including some non-limiting examples of linker sequences) and different modifications to increase the half-life of the Nanobody and their preparations can be found e.g. in WO 08/101985 and WO 08/142164.

Immunoglobulin single variable domains such as Domain antibodies and Nanobody (including VHH domains and humanized VHH domains), represent in vivo matured macromolecules upon their production, but can be further subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155:1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996). Immunoglobulin single variable domains such as Domain antibodies and Nanobody (including VHH domains) can be subjected to humanization, i.e. increase the degree of sequence identity with the closest human germline sequence. Alternative to Immunoglobulin domains, also an Ig superfamily or "Ig-like domains" are found in many proteins, which in fact constitute domains that are in sequence and structure very alike the Immunoglobulin-domain and Ig fold, respectively, but they are called Ig-like domains as to distinguish them from domains of Immunoglobulin antibodies themselves. Rather than being something special for antigen recognition it turned out that the Ig fold was particularly good for mediating interactions and was widely used. Immunoglobulin-like domains can be classified V, C1, C2, and I according to sequence pattern. Monobodies for instance comprise an immunoglobulin-like domain.

DETAILED DESCRIPTION

The present invention provides for generic protein tools that improve resolution and facilitate structural analysis of membrane proteins present in a native-like lipid environment, as provided by a nanodisc lipoparticle. Particularly, the invention concerns antigen-binding chimeric protein, called MegaBodies, specifically binding nanodisc belt proteins, commonly known as membrane-scaffold proteins (MSPs), which are essential in the assembly of nanodiscs as to wrap the lipid bilayers around the membrane protein of interest, captured or embedded within the nanodisc.

Nanodiscs are known to stabilize and solubilize membrane proteins embedded or captured within their lipid bilayer, so that the study of the nanodisc-entrapped membrane proteins is possible in a native-like environment, providing a better system than liposomes, detergent micelles or amphipols. However, when nanodisc-embedded membrane proteins are subjected to Cryo-EM, the issue of preferred particle orientation remains a hurdle to obtain high-resolution structural information of the embedded membrane protein. The addition of mass or increasing the size of particles in a rigid manner, as previously obtained by adding the MegaBodies specifically binding their (small) target proteins in Steyaert et al. (WO2019/086548A1) could solve this issue. Indeed, we demonstrated that using a MegaBody which specifically binds the target membrane protein enclosed within a nanodisc improves the structural resolution by reducing preferred particle orientation (see Example 4). However, this approach is quite labour intensive as it requires MegaBodies specific to each membrane protein of interest to resolve its structure. A generic target/antigen-binding site when analyzing membrane proteins that is recognized by a MegaBody would solve the issue of preferred particle orientation in Cryo-EM of membrane proteins and allow faster structural analyses. As each membrane protein is different, targeting the membrane proteins itself as previously demonstrated with Megabodies, is not solving this problem for generically approaching membrane protein structural analysis.

Membrane proteins encapsulated in a nanodisc provide for a native-like environment and thus have the components of the nanodisc in common, which may therefore serve as 'generic targets' for a MegaBody perhaps. However, the nanodisc belt proteins, constituting membrane-scaffold proteins (MSPs) in most cases, form a constantly moving dynamic belt around the phospholipid bilayers to hold the nanodisc in its assembled position, and therefore does not position these MSPs as the most straightforward or best candidates to increase the rigidity or fixation of protein particles for obtaining an improved alignment of proteins in these nanodiscs undergoing cryo-EM. The nanodisc-binding MegaBodies add additional mass to these dynamic nanodisc protein belt, but because of this flexible character of the MSP-belt in the nanodisc, this mass addition in itself was not expected to resolve the particle orientation issue of the particles comprising membrane proteins entrapped within the nanodiscs. The anti-MSP MegaBody was made to increase mass for membrane proteins in their nanodisc-bound form, though surprisingly, the anti-MSP MegaBody binding to the nanodisc particles was sufficient to reduce preferred particle orientation of the entrapped membrane protein, and thereby to improve the structural resolution in a similar or better way than the use of Megabodies directly binding the membrane protein of interest. So, the nanodisc-specific antigen-binding chimeric proteins of the invention aid in increasing mass of the nanodisc-containing particles, and increase particle size, reducing preferred particle orientation, and allowing better alignment of fragments to result in increased resolution in structural determination. So, by designing MegaBodies that bind to nanodiscs rather than to the target itself, we unexpectedly obtained a novel generic tool to facilitate high-resolution structural analysis of membrane proteins embedded in nanodiscs, by targeting just a single antigen (a generic nanodisc belt protein, in particular MSP) with this MegaBody.

In the first aspect of the invention, an antigen-binding chimeric protein or MegaBody is disclosed, which comprises an antigen-binding domain based on an immunoglobulin (Ig) domain, more particularly an Immunoglobulin variable domain (IVD), according to IMGT nomenclature, which is connected to a 'scaffold' or 'fusion partnering' protein, at one or more amino acid sites accessible in the first β-turn or loop of the IMGT annotated Ig domain, basically via a fusion to the β-turn AB, which connects β-strand A and β-strand B of the Ig domain, resulting in an interruption of the topology of said Ig antigen-binding domain, the latter capable of specifically binding a nanodisc belt protein, more specifically a Membrane scaffold protein (MSP) or MSP variant, as known in the art, and further defined herein. The β-turn AB of said antigen-binding Ig domain or IVD corresponds to the structural features as defined according to the IMGT® global reference nomenclature (Lefranc, 2014; and as presented in FIG. 2 of WO2019/086548A1). Specifically, said 'accessible' or 'exposed region' comprising said fusion sites is represented by an exposed loop of the Ig domain which is a loop or turn that is not one of the CDR loops, as these are involved in the nanodisc binding. The Ig domain involved in the antigen-binding of the antigen-binding chimeric protein of the invention has an Ig fold with at least 7 anti-parallel β-strands and at least 3 β-turns or loops connecting said β-strands, as defined according to the IMGT® global reference nomenclature (Lefranc, 2014). Specifically, the Ig domain of the antigen-binding chimeric protein may be derived from a VHH, or more preferably derived from an immunoglobulin single variable domain (ISVD) or from a Nanobody®.

In alternative embodiments, the exposed region of said antigen-binding domain of the antigen-binding chimeric protein specifically concerns β-turn AB, CC', C"D, DE, or EF, according to the IMGT nomenclature (Lefranc, 2014). So the scaffold protein is inserted within the antigen-binding domain as follows: in the first β-turn that connects β-strand A and β-strand B of said antigen-binding domain; or in the β-turn that connects β-strand C and β-strand C' of said antigen-binding domain; or in the β-turn that connects β-strand C" and β-strand D of said antigen-binding domain; or in the β-turn that connects β-strand D and β-strand E of said antigen-binding domain; or in the β-turn that connects β-strand E and β-strand F of said antigen-binding domain (wherein said β-turn is defined as by IMGT, Lefranc 2014).

An embodiment provides an antigen-binding chimeric protein wherein the antigen-binding domain is fused with the fusion partner protein, as further defined herein, in such a manner that the fusion partner protein is "interrupting" the antigen-binding domain its topology. In general, the "topology" of a protein refers to the orientation of regular secondary structures with respect to each other in three-dimensional space. Protein folds are defined mostly by the polypeptide chain topology[31]. So, at the most fundamental level, the 'primary topology' is defined as the sequence of secondary structure elements (SSEs), which is responsible for protein fold recognition motifs, and hence secondary and tertiary protein/domain folding. So, in terms of protein structure, the true or primary topology is the sequence of SSEs, i.e. if one imagines of being able to hold the N- and C-terminal ends of a protein chain, and pull it out straight, the topology does not change whatever the protein fold. The protein fold is then described as the tertiary topology, in analogy with the primary and tertiary structure of a protein (also see Ref. 37). The antigen-binding domain of the antigen-binding chimeric protein of the invention is hence interrupted in its primary topology, by introducing the fusion partner protein linkage, but unexpectedly said antigen-binding domain retained its tertiary structure allowing to retain its functional antigen-binding capacity.

In a particular embodiment of the invention, the fusions can be direct fusions, or fusions made by a linker or linker peptide, said fusion sites being immaculately designed to result in a rigid, non-flexible fusion protein. In addition to the position of the selected accessible site(s), the length and type of the linker peptide contributes to the rigidity of the resulting chimeric protein. Within the context of the present invention, the polypeptides constituting the antigen-binding chimeric protein are fused to each other directly, by connection via a peptide bond, or indirectly, whereby indirect coupling assembles two polypeptides through connection via a short peptide linker. Preferred "linker molecules", "linkers", or "short polypeptide linkers" are peptides with a length of maximum ten, or less, e.g. nine, eight, seven, six, five, four, three, or more preferably two, and even more preferably one amino acid residue, or is a direct fusion (no linker) to provide the desired rigidity to the junction of fusion at the accessible sites. Non-limiting examples of suitable linker sequences are described in the Example section.

In an alternative embodiment, an antigen-binding chimeric protein is described as a rigid fusion protein comprising i) a conserved N-terminal amino acid sequence of an immunoglobulin or Ig-like domain, ii) a fusion partner protein, and iii) an immunoglobulin domain sequence lacking said conserved N-terminal amino acid sequence of i), wherein i) and iii) are concatenated to said scaffold protein of ii). In a preferred embodiment, said rigid fusion protein comprises a conserved N-terminal amino acid sequence which is a conserved N-terminal domain of the FR1 region, comprising a conserved consensus sequence with residues as in SEQ ID NO:17, or a homologous sequence thereof, with a length between 11 and 15 residues (the end of the N-terminal part between residue 11 and 15 of SEQ ID NO:3 for example, i.e. near the first beta turn).

The term "fusion partner protein" or "scaffold protein" or "fusion partner protein domain", in the context as a part of the antigen-binding chimeric protein, refers to any type of protein which has a structure allowing a fusion with another protein, in particular with an antigen-binding domain, as described herein. Such a "scaffold", "junction" or "fusion partner" protein preferably has at least one exposed region in its tertiary structure to provide at least one accessible site to cleave as fusion point for the antigen-binding domain. The scaffold or partnering polypeptide is used to assemble with the antigen-binding domain and thereby results in the antigen-binding chimeric protein in a docked configuration to increase mass, provide symmetry, and/or provide a label, and/or add additional antigen-binding sites, and/or increase the half-life, and/or reduce immunogenicity, and/or improve or add a functionality to the antigen-binding domain. So, depending on the type of fusion partner protein that is used, a different purpose of the resulting antigen-binding chimeric protein is foreseen. The type and nature of the fusion partner protein is irrelevant in that it can be any protein, and depending on its structure, size, function, or presence, the fusion partner protein fused with said antigen-binding domain as in the antigen-binding chimeric protein of the invention will be of use in different application fields. The fusion partner protein thus preferably has a globular fold of which the 3D structure is known in the art, and has at least one exposed loop, which is suited for making the genetic fusion with the antigen-binding domain. The fusion partner protein its function is to add mass, rigidity and structural features to the antigen-binding domain, which will facilitate Cryo-EM analysis and this without complicating the structural analysis, i.e. preferably this fusion partner is not a membrane protein itself. The term 'any scaffold protein' or 'any fusion partner protein' as used herein relates to a protein of at least 20 amino acids, and preferably a protein of at least 30, or at least 40, or at least 50, or at least 80, or at least 100, or at least 150, or at least 200, or at least 250, or at least 300 amino acids, most preferably, a protein with a mass of at least 30 kDa. In one embodiment, said antigen-binding chimeric protein or MegaBody is built from a fusion partner protein with a total molar mass of at least 10, at least 20, at least 30, at least 35, at least 40, at least 45, at least 50, at least 60 kDa, or at least 80 kDa, so that the addition of mass by binding to the belt protein will be significant and sufficient to allow 3-dimensional structural analysis of the target protein present in the nanodisc when non-covalently bound to said antigen-binding chimeric protein. This particular size or weight resulting in the mass increase of the antigen-binding domain will affect the signal-to-noise ratio in the images to decrease. Secondly, the antigen-binding chimeric protein will offer a structural guide by providing adequate features for accurate image alignment, such as improved particle orientation, for difficult to crystallize proteins to reach a sufficiently high resolution using cryo-EM and X-ray crystallography.

The fusion partner protein as used herein should not be in itself a protein comprised within a nanodisc belt, such as the MSPs, since this would lead to a chain of antigen-binding domain parts of the antigen-binding chimeric protein binding to the fusion partner part of the antigen-binding chimeric protein of the present invention, and cause aggregation issues. So basically, the antigen-binding chimeric protein or MegaBody of the present invention comprises an antigen-binding domain specifically binding a nanodisc MSP or MSP variant protein, fused to a fusion partner protein which is different from said nanodisc MSP or MSP variant protein antigen, and has at least a size of 20 amino acids.

The structure of the fusion partner or scaffold protein will impact the final chimeric structure, so a person skilled in the art should implement the known structural information on the fusion partner protein and take into account reasonable expectations when selecting the fusion partner protein. Examples of fusion partner proteins are provided in the Examples of the present application, and a non-limiting number of proteins that are enzymes, soluble domains of membrane proteins, receptors, adaptor proteins, chaperones, transcription factors, nuclear proteins, antigen-binding proteins themselves, may be applied as fusion partner protein to create antigen-binding chimeric proteins of the invention. In a preferred embodiment, the 3D-structure of said scaffold proteins is known or can be predicted by a skilled person, so the accessible sites present on exposed regions or loops to fuse the antigen-binding domain with can be determined by said skilled person. In a specific embodiment, the *Helicobacter pylori* strain G27 type 1 HopQ its adhesin domain is used as a fusion partner (PDB 5LP2), wherein a circular permutation has been made in the amino acid sequence to obtain a suitable antigen-binding chimeric protein of the invention, as previously reported in Steyaert et al. (WO2019/086548A1) and as shown in SEQ ID NO:70 and 71, using adapted linker peptides or small truncations at the connecting site of the permutated sequence, respectively. Alternatively, the *E. coli* K12 strain Ygjk glucosidase is used as a fusion partner protein, as exemplified herein, or alternative a circular permutation (e.g. cYgjk or Ygjk_NO named herein, as depicted in SEQ ID NO:51) is used. Further to this principle, HopQ or Ygjk variants are usable as fusion partner proteins in the antigen-binding chimeric protein, and as applicable for the skilled person as well, and include, but are not limited to, further circular permutated proteins, mutants, homologues or orthologues, engineered or truncated forms, among others.

In another embodiment of the invention, the fusion partner protein used to generate the antigen-binding chimeric protein is a circularly permutated protein, more specifically, the circular permutation can be made between the N- and C-terminus of said fusion partner protein. In certain embodiments, the circularly permutated fusion partner protein is cleaved at another (not the N—C-terminus) accessible site of said fusion partner protein, to provide a site for fusion to the accessible site(s) of the Ig domain. The term "circular permutation of a protein" or "circularly permutated protein" refers to a protein which has a changed order of amino acids in its amino acid sequence, as compared to the wild type protein sequence, with as a result a protein structure with different connectivity, but overall similar three-dimensional (3D) shape. A circular permutation of a protein is analogous to the mathematical notion of a cyclic permutation, in the sense that the sequence of the first portion of the wild type protein (adjacent to the N-terminus) is related to the sequence of the second portion of the resulting circularly permutated protein (near its C-terminus), as described for instance in ref. 32. A circular permutation of a protein as compared to its wild protein is obtained through genetic or artificial engineering of the protein sequence, whereby the N- and C-terminus of the wild type protein are 'connected' and the protein sequence is interrupted at another site, to create a novel N- and C-terminus of said protein. The circularly permutated fusion partner proteins of the invention are the result of a connected N- and C-terminus of the wild type protein sequence, and a cleavage or interrupted sequence at an accessible or exposed site (preferentially a β-turn or loop) of said fusion partner protein, whereby the folding of the circularly permutate fusion partner protein is retained or similar as compared to the folding of the wild type protein. Said connection of the N- and C-terminus in said circularly permutated fusion partner protein may be the result of a peptide bond linkage, or of introducing a peptide linker, or of a deletion of a peptide stretch near the original N- and C-terminus if the wild type protein, followed by a peptide bond or the remaining amino acids. So basically, the antigen-binding chimeric protein or MegaBody of the present invention comprises an antigen-binding domain specifically binding a nanodisc belt protein, more specifically an MSP or MSP variant protein, fused to a fusion partner protein which is a circularly permutated protein or protein domain, with at least a size of 20 amino acids.

In another embodiment, the fusion partner protein of the antigen-binding chimeric protein is a labelled protein. In a specific embodiment, the label is a detectable label, which allows in vivo and/or non-covalent detection or labelling of the nanodisc. The term "detectable label", "labelling", "labelled protein", or "tag", as used herein, refers to detectable labels or tags allowing the detection, visualization, and/or isolation, purification and/or immobilization of the isolated or purified (poly-)peptides described herein, and is meant to include any labels/tags known in the art for these purposes. For instance, but not limiting are examples of affinity tags, such as chitin binding protein (CBP), maltose binding protein (MBP), glutathione-S-transferase (GST), poly(His) (e.g., 6×His or His6), Strep-Tag®, Strep-tag II® and Twin-Strep-Tag®; solubilization tags, such as thioredoxin (TRX), poly(NANP) and SUMO; chromatography tags, such as a FLAG-tag; epitope tags, such as V5-tag, myc-tag and HA-tag; fluorescent proteins (e.g., GFP, YFP, RFP etc.). Also included are combinations of any of the foregoing tags. Suitable labels and techniques for attaching, using and detecting them will be clear to the skilled person, and for example include, but are not limited to fluorescent labels or dyes (e.g., FITC, TRITC, coumarin and cyanine), phosphorescent labels, luminescent labels, such as luciferase, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (e.g., peroxidase, alkaline phosphatase, beta-galactosidase, urease or glucose oxidase, . . . ). Other suitable labels will be clear to the skilled person, and for example include moieties that can be detected using NMR or ESR spectroscopy. Such labelled antigen-binding chimeric protein of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

'Membrane proteins' (MP) are defined herein as proteins that are attached to a membranous structure. Peripheral membrane proteins are temporarily attached by non-covalent interactions and associate with one surface of the membrane. Integral membrane proteins are permanently attached to the membrane and are typically transmembrane, i.e. they span across the membrane. Typically, the membrane that must be spanned is composed of a lipid bilayer, that can be divided into three sections. The inner hydrocarbon region is approximately 27 to 32 Å thick. The very narrow boundary region between the hydrophobic inner core and the hydrophilic interfacial regions is approximately 3 Å. Finally, the outer polar head group region is approximately 8-10 Å, although this may be wider in membranes that include large amounts of carbohydrate-rich components. Cell membranes comprise phospholipid bilayers embedded with proteins. The amino acids of a membrane protein are localised according to polarity: non-polar (hydrophobic) amino acids associate directly with the lipid bilayer, whereas polar (hydrophilic) amino acids are located internally and face aqueous solutions. Transmembrane proteins typically adopt one of two tertiary structures: single helices/helical bundles or beta barrels (common in channel proteins). The primary structure of many transmembrane proteins is organized to include linear sequences of 19-23 hydrophobic amino acids to span the hydrophobic interior of a membrane in a helix. This produces a signature by which integral membrane proteins or transmembrane proteins can often be identified by their linear sequence. Other membrane proteins form β-barrels, with hydrophobic residues pointing to the outside of the barrel. Membrane proteins can diffuse in the plane of the membrane, though that can be restricted. Some proteins are kinetically stabilized in the membrane, with a finite lifetime before denaturation to biologically inactive forms. Membrane proteins can be post-translationally modified with lipids and carbohydrates, among other modifications. A number of large classes or families of membrane proteins has been described in the literature, and includes for instance, but non-limiting, receptors, ion channels, transporters, GPCRs, cytochrome proteins, . . . . In fact, membrane proteins constitute the majority of therapeutic targets, though remain hard to study due to their notorious properties (hydrophobic, low solubility, high potential to aggregate, . . . ). Several synthetic systems have been established to allow a more efficient and reliable process to capture, solubilize and stabilize such membranous target proteins. Synthetic polymers, such as styrene-maleic-acid co-polymers (SMAs) and di-isobutylene-maleic acid (DIBMA), efficiently solubilize membrane proteins directly from cells or extracts for instance. Lipoparticles or liposome assemblies are applied to stabilize membrane proteins. Liposomes are artificial spherical lipid membranes where membrane proteins can assemble. The present invention relates to such 'lipoprotein nanoparticles', constituting a lipid bilayer, which is held together by protein belts. More specifically, the synthetic systems of 'nanodiscs' are described herein, wherein the belt contains amphipathic proteins or amphipathic peptides, preferably at each hydrophobic edge, aligning in a double belt. Nanodiscs are structurally very similar to discoidal high-density lipoproteins (HDL), and their belt proteins involve helix-rich membrane scaffold proteins (MSPs), which are known in the art and concern artificially designed proteins comprising truncated forms of apolipoprotein (apo) A-I, wherein several helix elements are repeated or shuffled or engineered further, as to create diverse options for wrapping around the patch of a lipid bilayer to form a disc-like particle.

Nanodiscs are widely applied to reconstitute (detergent-) solubilized membrane proteins in an artificial environment resembling the native membrane, thereby stabilizing membrane proteins to study binding of ligands, agonists or antagonists. Additional apolipoprotein-based nanoparticle systems with varying diameters of the nanodiscs, depending on the MSP variant used to constitute the nanodics, have been developed and are included herein as nanodisc systems 33-3s. Generally, the nanodisc or lipid nanoparticle size is dictated by the scaffolding apolipoprotein-based MSP belt at optimum lipid content. Alternative to the apolipoproteins or MSPs, the saposin-lipoprotein nanoparticle system was developed, applying Saposin-based nanodisc belt proteins instead of apolipoprotein-derived belt proteins[36].

So the term 'nanodisc belt protein' as used herein relates to any protein used to constitute the belt, comprising a multitude of polypeptides, arranged around the lipid bilayer in said synthetic lipoprotein nanoparticle systems, for which Apolipoprotein-derived MSPs and Saposin-based scaffolds are provided as an example herein. These belt proteins, such as MSPs or MSP variants, provide a hydrophobic surface facing the lipids, and a hydrophilic surface at the outside, making the nanodiscs or nanoparticles highly soluble in aqueous solutions. Once assembled into nanodiscs, the target membrane proteins can be kept in solution in the absence of detergents.

In one embodiment, the antigen-binding domain of the antigen-binding chimeric protein of the invention specifically binds a nanodisc MSP or MSP variant protein in it nanodisc-bound state, or in its nanodisc-free state. The term 'nanodisc-bound' refers to the conformation of the belt protein that is accessible for binding to when the MSP belt is present as part of a nanodisc, while the nanodisc-free state refers to the apo-state of the MSP protein, so in a lipid free environment. The size of the nanodiscs or lipid nanoparticles is governed by the MSP belt proteins or type of MSP variant. Typically, the resulting nanobilayer particles are about 7-17 nm in diameter. Depending on the MSP variant used (e.g. MSP1, MSP1E1, MSP1E2, MSP1E3, MSP1D1, MSP1E3D1, MSP1E3D1_D73C, MSP2, MSP2N2, and variants thereof, or as provided in (but not limited to) for instance refs 2, 21, 40, and 41), the apolipoprotein-derived nanodiscs differ in size, and provide for slightly engineered variations in the amino acid sequence. Most widely employed are MSP1D1 and MSP1D1-deltaH5, but also other deletion mutants of MSP1D1 are suitable for the generation of nanodiscs[20]. Larger scaffold protein variants include MSP2N2 and MSP2N3 (e.g. ref. 2).

So, a further embodiment provides for an antigen binding chimeric protein of the invention specifically recognizing a membrane-scaffold protein (MSP), or to an MSP variant, or an engineered mutant or variant thereof. More specifically, the antigen-binding chimeric protein specifically binds an engineered or truncated form or the apolipoproteins (Apo) A-I, preferably the human Apo A-I, or a derivative thereof. The human Apolipoprotein A-I, as depicted in SEQ ID NO:69, provides for the majority of the amino acid sequence of MSP1, covered by amino acid residue 79-267 of SEQ ID NO:1. However, membrane scaffold proteins derived from mouse and rat apo A-I protein instead of the human homologue are often applied for immunization purposes involving nanodisc-entrapped membrane protein (i.e. membrane protein-loaded nanodiscs), since these improve antibody specificity of human target protein-nanodisc complexes, and thus could also constitute the MSP antigen of the invention. The MSP1 variants as exemplified herein and provide by SEQ ID NO:1, 2 and 68, also schematically depicted in FIG. 9*a* demonstrate that an antigen-binding domain specifically binding to MSP may also bind MSP variants. The panel of MSP binders selected herein has shown to be cross-reacting to the MSP variants as well. Nanodiscs, whether apolipoprotein or saposin-based, have a number of advantages compared to other systems for membrane protein solubilization and reconstitution, in particular for ligand binding studies, analysis of conformational dynamics, and protein interaction studies. Proteins have better stability and activity inside nanodiscs. Nanodiscs can be used to reconstitute membrane proteins such as GPCRs or transporters in an artificial environment resembling the native membrane. These nanodisc-stabilized proteins can be directly purified by standard chromatographic procedures. The resulting purified membrane protein/nanodisc complex can be used in applications that require access to both the physiologically intracellular and extracellular surfaces of the protein and thus allows unrestricted access of antagonists, agonists, G proteins and other interaction partners. Membrane protein/nanodisc complexes are advantageous to use in cryo-EM or crystallization studies because of their increased homogeneity, protection from aggregation, and conservation of conformational structure. So, the combination of nanodiscs and EM was proven to be very effective for structural and protein-protein interaction analysis, though for cryo-EM the issue of preferred orientation of the particles during vitrification remained. The antigen-binding chimeric proteins of the invention specifically binding said nanodiscs were shown to further complete the toolbox for cryo-EM by solving this issue in a generic manner.

Figure 1:
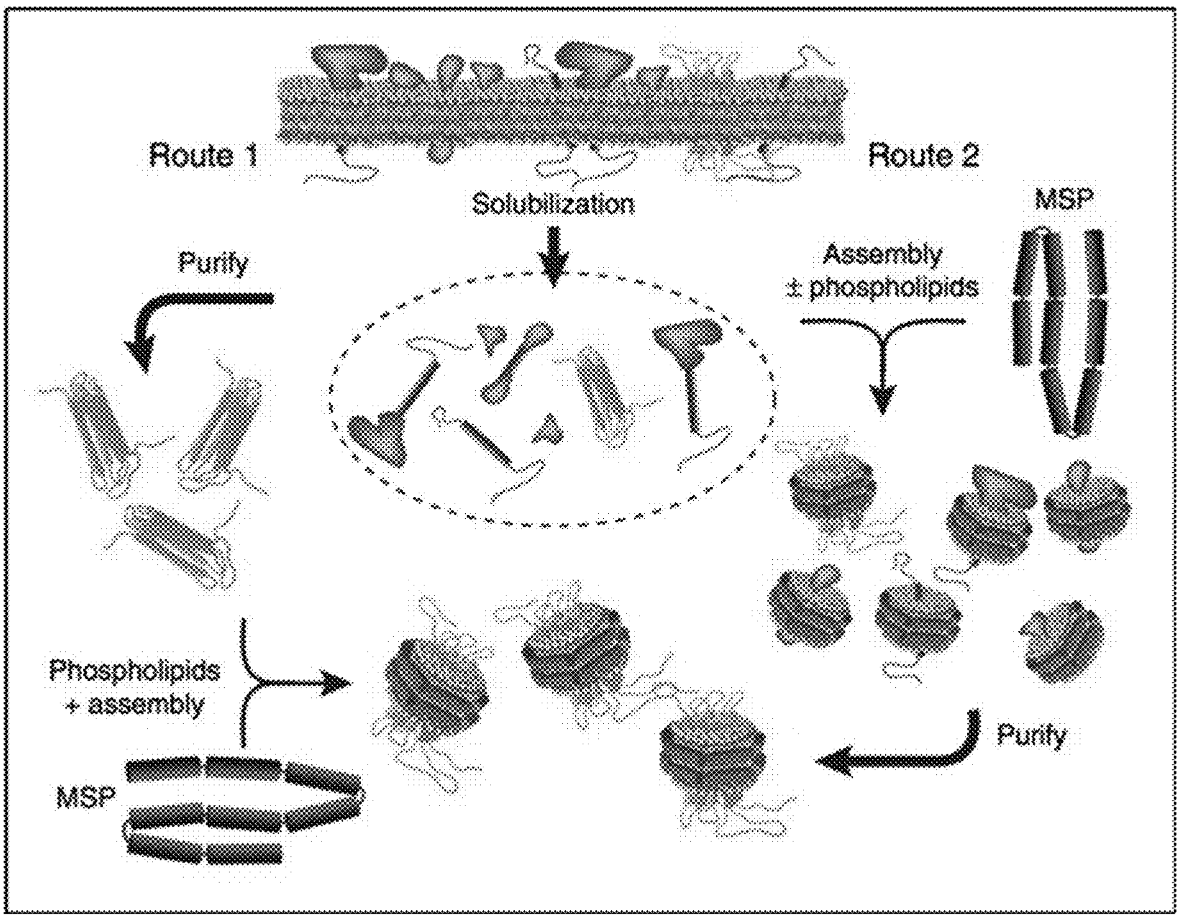
FIG. 1. Assembling Membrane Proteins into nanodiscs.

Nanodiscs are synthesized by mixing together phospholipid/detergent micelles and MSP proteins, followed by detergent removal. The ratio of phospholipids to MSP is a critical factor for successful nanodisc assembly and needs to be determined for each new combination of protein, phospholipid, and MSP. To incorporate an integral or peripheral membrane protein of interest into the disc, the membrane protein solubilized in detergent micelles is also added to the nanodisc mix, before detergent removal. During the process of nanodisc assembly, the amphipol polymers wrap around the hydrophobic patches of the membrane protein to form a stable complex in solution. The self-assembly process may be accomplished in several ways (as shown in FIG. 1). The assembled nanodiscs may be added to a cell-free reaction, where the membrane protein can insert spontaneously. Alternatively, the already solubilized membrane protein is mixed with phospholipids, detergent, and MSP protein. Upon detergent removal, the membrane protein/nanodisc complex forms. Or, detergent and MSP are added to membranes expressing the protein of interest. A complex of membrane phospholipids, proteins, and MSP forms. The advantage of using nanodiscs and thereby removing the detergent prevents damage of detergent compounds to the transmembrane domain's integrity and to its interfaces with the extracellular region[38].

As used herein, the term "protein complex" or "complex" refers to a group of two or more associated macromolecules, whereby at least one of the macromolecules is a protein. A protein complex, as used herein, typically refers to associations of macromolecules that can be formed under physiological conditions. Individual members of a protein complex are linked by non-covalent interactions. A protein complex can be a non-covalent interaction of only proteins, and is then referred to as a protein-protein complex; for instance, a non-covalent interaction of two proteins, of three proteins, of four proteins, etc. More specifically, a complex of the antigen-binding chimeric protein and the antigen itself, i.e. the nanodisc belt protein (in its apo-state), or of the antigen-binding chimeric protein and the nanodisc comprising the antigen, in particular the nanodisc MSP or MSP variant protein, through interaction of the antigen-binding chimeric protein its antigen-binding domain with the nanodisc MSP or MSP variant protein. Specifically, the present invention relates to complexes that comprise the antigen-binding chimeric protein or antigen-binding domain specifically binding the nanodisc MSP or MSP variant protein, and the nanodisc MSP or MSP variant proteins, which may be in a nanodisc-free state (apo-state), or in a nanodisc-bound state, the latter referring to a complex also comprising the nanodisc. In the complex of the present invention, said nanodisc may also comprise other proteins, such as membrane proteins of interest, which are entrapped within the nanodisc. The complex may hence also comprise the antigen-binding chimeric protein or MegaBody, bound to the nanodisc MSP or MSP variant protein, present in a nanodisc-bound state, and a nanodisc, including additional membrane protein(s) present within the assembled nanodisc. Protein complex assembly can result in the formation of homo-multimeric or hetero-multimeric complexes. Moreover, interactions can be stable or transient. The term “multimer(s)”, “multimeric complex”, or “multimeric protein(s)” comprises a plurality of identical or heterologous polypeptide monomers.

Polypeptides can be capable of self-assembling into multimeric assemblies (i.e.: dimers, trimers, hexamers, pentamers, octamers, etc.) formed from self-assembly of a plurality of a single polypeptide monomers (i.e., “homo-multimeric assemblies”). The multimeric assemblies can be used for any purpose, and provide a way to develop a wide array of protein “nanomaterials”.

A specific embodiment discloses a nanodisc comprising MSP or MSP variant belt proteins or double belts of membrane scaffold proteins (MSPs) or of MSP variants, or of a mixture of different MSP variant proteins, a phospholipid assembly, an antigen-binding chimeric protein as disclosed herein, specifically bound to said nanodisc belt protein, and optionally, a target membrane protein, which is different from the MSP or MSP variant belt protein.

Alternatively, a composition of an antigen-binding chimeric protein is disclosed herein, which comprises a first and a second antigen-binding chimeric protein as described herein, wherein the first antigen-binding chimeric protein specifically binds to MSP or MSP variant proteins, and the antigen-binding domain of said second antigen-binding chimeric protein specifically binds the fusion partner protein of the first antigen-binding chimeric protein. To avoid aggregates or chain-reaction of antigen-binding chimeric proteins binding their own fusion partner protein, the fusion partner protein of said second antigen-binding chimeric protein is different from the fusion partner protein of said first antigen-binding chimeric protein. With ‘different’ is meant herein for the purpose of the invention, that an amino acid mutation, deletion, insertion or substitution or a modification of the fusion partner protein of the second antigen-binding chimeric protein results in the non-binding of the antigen-binding domain of the second antigen-binding chimeric protein to said fusion partner protein part of the second antigen-binding chimeric protein. Another embodiment relates to said composition of antigen-binding chimeric proteins, in a complex bound with its antigen or target protein.

One further aspect relates to an antigen-binding domain being an immunoglobulin single variable domain (ISVD) or a Nanobody® specifically binding a nanodisc belt protein, more particularly, an MSP protein or variant of an MSP Nanodisc belt protein, which can be used to increase nanodisc protein mass, to improve stability, or to stabilize certain conformations of the nanodisc complex. In a specific embodiment, the antigen-binding domain ISVDs contain a CDR1, CDR2, and CDR3 sequence selection from the corresponding CDR1, CDR2, and CDR3 annotated regions in the Nb sequence selected from the group of SEQ ID NO:37-50, wherein said CDR annotation is performed according to the IMGT annotation (as provided in LeFranc, 2014), or alternatively delineation of the CDR sequences can also be done by using the MacCallum et al. (J. Mol. Biol. (1996) 262, 732-745), AbM (AbM is Oxford Molecular Ltd.’s antibody modelling package as described on http://www.bioinf.org.uk/abs/index.html), Chothia (Chothia and Lesk, 1987; Mol Biol. 196:901-17), or Kabat (Kabat et al., 1991; $5^{th}$ edition, NIH publication 91-3242). These annotations differ slightly, but each intend to comprise the regions of the loops involved in binding the target. Even more specifically, the antigen-binding domain represented by an ISVD may be provided by a sequence comprising a sequence selected from a group of ISVD sequences depicted in SEQ ID NO:37-50, providing for the exemplified Nbs herein that were selected for specifically binding the MSP1D1 and MSP2N2 variants, or selected from a group of homologous ISVDs with a sequence with at least 95% amino acid identity to any of SEQ ID NO:37-50, or at least 97% identity thereof, wherein the CDRs are 100% identical. The most specific embodiment provides for an ISVD comprising CDR1, CDR2, and CDR3 of SEQ ID NO:48, or alternatively the ISVD comprising SEQ ID NO:48, or a homologue with at least 95% identity thereof, wherein the CDRs are identical and variations in the amino acid sequence are only present in the Framework residues not taking part in antigen-binding.

As described throughout this application, the antigen-binding chimeric proteins ‘MegaBodies’ specifically binding the nanodisc belt MSP or MSP variant protein, according to the invention, are fusion proteins that are designed in a unique manner to avoid that the junction is a flexible, loose, weak link/region within the chimeric protein structure. A convenient means for linking or fusing two polypeptides is by expressing them as a fusion protein from a recombinant nucleic acid molecule, which comprises a first polynucleotide encoding a first polypeptide operably linked to a second polynucleotide encoding the second polypeptide, in the classical known manner. In the recombinant nucleic acid molecule of the present invention however, the interruption of the topology of the antigen-binding domain by said scaffold is also reflected in the design of the genetic fusion from which said antigen-binding chimeric protein is expressed. The antigen-binding domain its topology is interrupted in the fact that its sequence will contain an insertion of the fusion partner or scaffold protein sequence(s) (or a circularly permutated sequence, a variant or a domain or fragment thereof), so that the N-terminal antigen-binding domain fragment and C-terminal antigen-binding domain fragment are separated by the fusion partner protein sequence or fragments thereof within said nucleic acid molecule. Another embodiment relates to the antigen-binding chimeric protein encoded by a chimeric gene formed by recombining parts of a gene encoding for an antigen-binding domain, and parts of a gene encoding the fusion partner protein, wherein said encoded fusion partner protein interrupts the primary topology of the encoded antigen-binding domain at one or more accessible sites of said domain via at least two or more direct fusions or fusions made by encoded peptide linkers. In a specific embodiment, the antigen-binding chimeric protein specifically binding the MSP or MSP variant protein comprises an amino acid sequence that is selected from the group of antigen-binding chimeric protein sequences depicted in SEQ ID NO:53-67, representing the MegaBodies that were designed using the Nbs of SEQ ID NO:37-50, specifically binding MSP, and fused with a cHopQ fusion partner protein, or fused with a cYgjk fusion partner protein. Alternatively the invention provides for an antigen-binding chimeric protein specifically binding the MSP or MSP variant protein comprising an amino acid sequence that is selected from the group of antigen-binding chimeric protein sequences that are homologues with at least 90% amino acid identity to any of SEQ ID NO:53-67, taken over the full length of the sequence, and retaining 100% identity in the CDR regions. More specifically, the invention provides for an antigen-binding chimeric protein specifically binding the MSP or MSP variant protein comprising an amino acid sequence that is selected from the group of antigen-binding chimeric protein sequences that are homologues with at least 95% amino acid identity to any of SEQ ID NO:53-67, taken over the full length of the sequence, and retaining 100% identity in the CDR regions.

In another embodiment, a chimeric gene is described with at least a promoter, said nucleic acid molecule encoding the antigen-binding chimeric protein, and a 3' end region containing a transcription termination signal. Another embodiment relates to an expression cassette encoding said antigen-binding chimeric protein of the present invention, or comprising the nucleic acid molecule or the chimeric gene encoding said antigen-binding chimeric protein. Said expression cassettes are in certain embodiments applied in a generic format as an immune library, containing a large set of Ig domains or Nanobodies or MegaBodies to select for the most suitable binders of the target.

Further embodiments relate to vectors comprising said expression cassette or nucleic acid molecule encoding the nanodisc belt protein-specific antigen-binding chimeric protein of the invention. The term "vector", "vector construct", or "recombinant vector", as used herein, can be double-stranded or single-stranded and may be DNA, RNA, or DNA/RNA hybrid molecules, in any conformation including but not limited to linear, circular, coiled, supercoiled, torsional, nicked and the like. These vectors of the invention include but are not limited to plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC), all of which are well-known and can be purchased from commercial sources. Any vector may be used to construct and express the fusion molecules used in the invention. General classes of vectors of particular interest include prokaryotic and/or eukaryotic cloning vectors, expression vectors, fusion vectors, phage and yeast display vectors, shuttle vectors for use in different hosts, mutagenesis vectors, transcription vectors, vectors for receiving large inserts and the like. Most of the requisite methodology can be found in Ausubel et al. 2007.

In particular embodiments, vectors for recombinant expression in prokaryotic cells or eukaryotic cells allow to produce the antigen-binding chimeric proteins and purify them in the presence or absence of their targets. Vector constructs prepared for introduction and expression into a prokaryotic or eukaryotic host will typically comprise a replication system recognized by the host, including the intended DNA fragment encoding the nucleic acid molecule of the present invention, and will preferably also include transcription and translational initiation regulatory sequences operably linked to the molecule-encoding segment. Expression systems may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included, where appropriate, from secreted polypeptides of the same or related species, which allow the protein to cross and/or lodge in cell membranes, or be secreted from the cell. An appropriate promoter and other necessary vector sequences will be selected so as to be functional in the host. Other vectors can be integrated into the genome of a host cell upon introduction into the host cell, and are thereby replicated along with the host genome. Examples of workable combinations of cell lines and expression vectors are described in for example, Sambrook, et al. Molecular Cloning: A Laboratory Manual, $4^{th}$ ed., Cold Spring Harbor Press, Plainsview, New York (2012); and Ausubel et al., Current Protocols in Molecular Biology (Supplement 114), John Wiley & Sons, New York (2016). Many useful vectors for expression in bacteria, yeast, fungal, mammalian, insect, plant or other cells are well known in the art.

Alternative embodiments relate to host cells, comprising the nanodisc MSP belt protein-specific antigen-binding chimeric protein of the invention, or the nucleic acid molecule or expression cassette or vector encoding the MSP or MSP variant protein-specific antigen-binding chimeric protein of the invention. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. For all standard techniques see, for example, Sambrook et al., Molecular Cloning: A Laboratory Manual, $4^{th}$ ed., Cold Spring Harbor Press, Plainsview, New York (2012); and Ausubel et al., Current Protocols in Molecular Biology (Supplement 114), John Wiley & Sons, New York (2016). Recombinant host cells, in the present context, are those which have been genetically modified to contain an isolated DNA molecule, nucleic acid molecule or expression construct or vector of the invention. The DNA can be introduced by any means known to the art which are appropriate for the particular type of cell, including without limitation, transformation, lipofection, electroporation or viral mediated transduction. A DNA construct capable of enabling the expression of the chimeric protein of the invention can be easily prepared by the art-known techniques such as cloning, hybridization screening and Polymerase Chain Reaction (PCR). Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (2012), Wu (ed.) (1993) and Ausubel et al. (2016).

Host cells can be either prokaryotic or eukaryotic. The host cell may also be a recombinant host cell, which involves a cell which has been genetically modified to contain an isolated DNA molecule, nucleic acid molecule encoding the nanodisc belt protein-specific antigen-binding chimeric protein of the invention.

Representative host cells that may be used include but are not limited to, bacterial cells, yeast cells, plant cells and animal cells. Bacterial host cells suitable for production of the antigen-binding chimeric proteins of antigen-binding domains of the invention include *Escherichia* spp. cells, *Bacillus* spp. cells, *Streptomyces* spp. cells, *Erwinia* spp. cells, *Klebsiella* spp. cells, *Serratia* spp. cells, *Pseudomonas* spp. cells, and *Salmonella* spp. cells. Yeast host cells suitable for use with the invention include species within *Saccharomyces, Schizosaccharomyces, Kluyveromyces, Pichia* (e.g. *Pichia pastoris*), *Hansenula* (e.g. *Hansenula polymorpha*), *Yarrowia, Schwanniomyces, Schizosaccharomyces, Zygosaccharomyces* and the like. *Saccharomyces cerevisiae, S. carlsbergensis* and *K. lactis* are the most commonly used yeast hosts, and are convenient fungal hosts. Animal host cells suitable for use with the invention include insect cells and mammalian cells (most particularly derived from Chinese hamster (e.g. CHO), and human cell lines, such as HeLa). Exemplary insect cell lines include, but are not limited to, Sf9 cells, baculovirus-insect cell systems (e.g. review Jarvis, Virology Volume 310, Issue 1, 25 May 2003, Pages 1-7). The host cells may be provided in suspension or flask cultures, tissue cultures, organ cultures and the like. Alternatively, the host cells may also be transgenic animals.

Another embodiment of the invention relates to a method of producing an the MSP or MSP variant-specific antigen-binding chimeric protein according to the invention comprising the steps of (a) culturing a host comprising the vector, expression cassette, chimeric gene or nucleic acid sequence of the present invention, under conditions conducive to the expression of the antigen-binding chimeric protein, and (b) optionally, recovering the expressed polypeptide.

In particular embodiments, the host cell further co-expresses the antigen, i.e. the nanodisc MSP or MSP variant protein, and/or co-express the target membrane protein that may be entrapped in nanodiscs. Another embodiment relates to said host cell expressing the MSP or MSP variant protein-specific antigen-binding chimeric protein which also contains nanodiscs, which specifically bind the antigen-binding chimeric proteins via binding of the nanodisc its MSP protein-containing belt to the antigen-binding domain of said antigen-binding chimeric proteins. Said host cells may also contain a membrane protein of interest assembled within said nanodiscs.

Another embodiment discloses the use of said host cells, or a membrane preparation isolated thereof, or proteins isolated therefrom, for screening purposes, protein capturing and purification, or biophysical studies. In one embodiment, the vectors of the present invention are suitable to use in a method involving displaying a collection of antigen-binding chimeric proteins, preferably an immune library, at the extracellular surface of a population of cells. Surface display methods are reviewed in Hoogenboom, (2005; Nature Biotechnol 23, 1105-16), and include bacterial display, yeast display, (bacterio)phage display. Preferably, the population of cells are yeast cells. The different yeast surface display methods all provide a means of tightly linking each antigen-binding chimeric protein encoded by the library to the extracellular surface of the yeast cell which carries the plasmid encoding that protein. Most yeast display methods described to date use the yeast *Saccharomyces cerevisiae*, but other yeast species, for example, *Pichia pastoris*, could also be used. More specifically, in some embodiments, the yeast strain is from a genus selected from the group consisting of *Saccharomyces, Pichia, Hansenula, Schizosaccharomyces, Kluyveromyces, Yarrowia*, and *Candida*. The vectors disclosed herein may also be suited for prokaryotic host cells to surface display the proteins or to recombinantly produce the proteins. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. Furthermore, vectors for phage display are applied, and used for display of the antigen-binding chimera on the bacteriophages, followed by panning. Display can for instance be done on M13 particles by fusion of the antigen-binding chimera, within said generic vector, to phage coat protein III (Hoogenboom, 2000; Immunology today. 5699:371-378).

The rigidity of a protein is in fact inherent to the (tertiary) structure of the protein, in this case the nanodisc MSP or MSP variant protein-specific antigen-binding chimeric protein or MegaBody. The rigidity of MegaBodies has been described in Steyaert et al. (WO2019/086548A1) to provide for a rigidity sufficiently strong to 'orient' or 'fix' the target or antigen bound by the MegaBody. In the present invention however, it is not the target of the MegaBody, which is the nanodisc MSP belt protein, but the membrane protein entrapped in said nanodisc MSP belt protein-containing nanodiscs which as a consequence of the MegaBody bound to the nanodisc belt protein could be held in a certain orientation thereby obtaining a membrane protein better suited for structural analysis. Until now, the application of MegaBodies was limited to direct binding to the target of interest, as a directly interacting chaperone. The fact that the MegaBodies of the present invention were capable of providing a structural advantage to membrane proteins present within a nanodisc revealed their generic use in such a commonly used complex. So despite the dynamics and flexibility of the MSP belt as part of the nanodisc system, the addition of extra mass to this nanodisc belt via a non-covalent MegaBody interaction, is apparently sufficient to reduce the preferred particle orientation of the membrane protein entrapped within the nanodisc. The advantages of these generic anti-nanodisc MegaBodies are numerous, with a straightforward use in structural biology of membrane proteins, to facilitate Cryo-EM and X-ray crystallography, by resolving the recurrent issues of limitation in particle size, preferred orientation, and restricted alignment of fragments.

Another aspect of the invention thus relates to the use of the nanodisc MSP protein-specific antigen-binding chimeric protein of the present invention or of the use of the nucleic acid molecule, chimeric gene, the expression cassette, the vectors, the complex, or the compositions, for structural analysis of a target membrane protein. In particular, the use of the antigen-binding chimeric protein in structural analysis of a target membrane protein wherein said target membrane protein is present in the nanodisc or lipid nanoparticle comprising the nanodisc belt proteins that specifically bind the MegaBody, and wherein the target membrane protein is different from the nanodisc MSP or MSP variant belt protein. "Solving the structure" or "structural analysis" as used herein refers to determining the arrangement of atoms or the atomic coordinates of a protein, and is often done by a biophysical method, such as X-ray crystallography or cryogenic electron-microscopy (cryo-EM). Specifically, an embodiment relates to the use in structural analysis comprising single particle cryo-EM or comprising crystallography. The use of antigen-binding chimeric proteins of the present invention in structural biology renders the major advantage to serve as crystallization aids, namely to play a role as crystal contacts and to increase symmetry, and even more to be applied as rigid tools in Cryo-EM, which will be very valuable to solve large structures, but mainly to reduce size barriers coped with today, and finally also to increase symmetry.

Using cryo-EM for structure determination has several advantages over more traditional approaches such as X-ray crystallography. In particular, cryo-EM places less stringent requirements on the sample to be analysed with regard to purity, homogeneity and quantity. Importantly, cryo-EM can be applied to targets that do not form suitable crystals for structure determination. A suspension of purified or unpurified protein, either alone or in complex with other proteinaceous molecules such as an antigen-binding chimeric protein or non-proteinaceous molecules such as a nucleic acid, can be applied to carbon grids for imaging by cryo-EM. The coated grids are flash-frozen, usually in liquid ethane, to preserve the particles in the suspension in a frozen-hydrated state. Larger particles can be vitrified by cryofixation. The vitrified sample can be cut in thin sections (typically 40 to 200 nm thick) in a cryo-ultramicrotome, and the sections can be placed on electron microscope grids for imaging. The quality of the data obtained from images can be improved by using parallel illumination and better microscope alignment to obtain resolutions as high as ~3.3 Å. At such a high resolution, ab initio model building of full-atom structures is possible. However, lower resolution imaging might be sufficient where structural data at atomic resolution on the chosen or a closely related target protein and the selected heterologous protein or a close homologue are available for constrained comparative modelling. To further improve the data quality, the microscope can be carefully aligned to reveal visible contrast transfer function (CTF) rings beyond ⅓ $Å^{-1}$ in the Fourier transform of carbon film images recorded under the same conditions used for imaging. The defocus values for each micrograph can then be determined using software such as CTFFIND.

Another aspect of the invention relates to a method of determining the 3-dimensional structure of a 'target membrane protein' or 'membrane protein of interest', as used interchangeably herein, present within (or encapsulated within) a nanodisc, comprising the steps of:

a) optionally, first assembling a nanodisc comprising a target membrane protein, using a method known by the skilled person, and/or as disclosed herein (e.g. in FIG. 1), and
b) Mixing the (assembled) nanodisc comprising a target membrane protein complex (of step a)) with the MSP or MSP variant protein-specific antigen-binding chimeric protein of the invention, to obtain binding of the latter via its antigen-binding domain to said nanodisc MSP belt, as a non-covalent interaction with the nanodisc its belt proteins, and
c) display said mix or complex in suitable conditions, for structural analysis, to wherein the 3D structure of said target membrane protein is determined, preferably at high-resolution.

With high-resolution is meant, according to the skilled person, at least a resolution equal to or lower than 5 Å.

As used herein, the terms "determining," "measuring," "assessing," and "assaying" are used interchangeably and include both quantitative and qualitative determinations. The terms "suitable conditions" refers to the environmental factors, such as temperature, movement, other components, and/or "buffer condition (s)" among others, wherein "buffer conditions" refers specifically to the composition of the solution in which the assay is performed. The said composition includes buffered solutions and/or solutes such as pH buffering substances, water, saline, physiological salt solutions, glycerol, preservatives, etc. for which a person skilled in the art is aware of the suitability to obtain optimal assay performance.

In a specific embodiment, said structural analysis is done via X-ray crystallography. In another embodiment, said 3D analysis comprises Cryo-EM. More specifically, a methodology for Cryo-EM analysis is described here as follows. A sample (e.g. MegaBody protein of choice in a complex as described previously herein), is applied to a best-performing discharged grid of choice (carbon-coated copper grids, C-Flat, 1.2/1.3 200-mesh: Electron Microscopy Sciences; gold R1.2/1.3 300 mesh UltraAuFoil grids: Quantifoil; etc.) before blotting, and then plunge-frozen in to liquid ethane (Vitrobot Mark IV (FEI) or other plunger of choice). Data for a single grid are collected at 300 kV Electron Microscope (Krios 300 kV as an example with supplemented phase plate of choice) equipped with a detector of choice (Falcon 3EC direct-detector as an example). Micrographs are collected in electron-counting mode at a proper magnification suitable for an expected MegaBody-Nanodisc-protein complex size. Collected micrographs are manually checked before further image processing. Apply drift correction, beam induced motion, dose-weighting, CTF fitting and phase shift estimation by a software of choice (RELION, SPHIRE packages as examples). Pick particles with a software of choice and use them for to 2D classification. Manually-inspected 2D classes and remove false positives. Bin particles accordingly to data collection settings. Generate an initial 3D reference model by applying a proper low-pass filter and generate a number (six as an example) of 3D classes. Use original particles for 3D refinement (if needed use soft mask). Estimate a reconstruction resolution by using Fourier Shell Correlation (FSC)=0.143 criterion. Local resolution can be calculated by the MonoRes implementation in Scipion. Reconstructed cryo-EM maps can be analyzed using UCSF Chimera and Coot software. The design model can be initially fitted using UCSF Chimera and analyzed by software of choice (UCSF Chimera, PyMOL or Coot).

These nanodisc MSP-specific MegaBodies may also be applicable as a chaperone in structure-based drug design and structure-based screening for druggable membrane proteins. So in one embodiment, the method and antigen-binding chimeric protein of the invention is used as a tool or aid for structure-based drug design and structure-based drug screening. The iterative process of structure-based drug design often proceeds through multiple cycles before an optimized lead goes into phase I clinical trials. The first cycle includes the cloning, purification and structure determination of the target protein or nucleic acid by one of three principal methods: X-ray crystallography, NMR, or homology modelling. Using computer algorithms, compounds or fragments of compounds from a database are positioned into a selected region of the structure. One could use the antigen-binding chimeric protein of the invention to fix or stabilize certain structural conformations of a target. The selected compounds are scored and ranked based on their steric and electrostatic interactions with this target site, and the best compounds are tested with biochemical assays. In the second cycle, structure determination of the target in complex with a promising lead from the first cycle, one with at least micromolar inhibition in vitro, reveals sites on the compound that can be optimized to increase potency. Also at this point, the antigen-binding chimeric protein of the invention may come into play, as it facilitates the structural analysis of said target in a certain conformational state. Additional cycles include synthesis of the optimized lead, structure determination of the new target:lead complex, and further optimization of the lead compound. After several cycles of the drug design process, the optimized compounds usually show marked improvement in binding and, often, specificity for the target. A library screening leads to hits, to be further developed into leads, for which structural information as well as medicinal chemistry for Structure-Activity-Relationship analysis is essential.

Another embodiment relates to a method of identifying (conformation-selective) compounds, comprising the steps of:

i) providing a target membrane protein in a nanodisc and an MSP-specific antigen-binding chimeric protein of the invention bound to said nanodisc
ii) providing a test compound
iii) evaluating the selective binding of the test compound to the target membrane protein present in the nanodisc.

The compounds to be tested can be any small chemical compound, or a macromolecule, such as a protein, a sugar, nucleic acid or lipid. Typically, test compounds will be small chemical compounds, peptides, antibodies or fragments thereof. It will be appreciated that in some instances the test compound may be a library of test compounds. In particular, high-throughput screening assays for therapeutic compounds such as agonists, antagonists or inverse agonists and/or modulators form part of the invention.

It is to be understood that although particular embodiments, specific configurations as well as materials and/or molecules, have been discussed herein for engineered cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Specifically, in single particle cryo-EM, membrane proteins embedded in liposomes, lipoparticles or nanodiscs adopt preferential orientations in free-standing ice (FIG. 6*a*). As an alternative, detergent-solubilised receptors possess appropriate particle projection distribution, however, the use of detergents negatively impacts the structural integrity of the transmembrane region and causes the misinterpretation of the structure and related function of the membrane protein[38]. To achieve sufficient particle numbers per micrograph in free-standing ice, detergent-solubilised membrane proteins need to be highly concentrated when compared to other membrane proteins in amphipols or nanodiscs 6,7. Additionally, structural and functional characterisation of membrane proteins embedded in a nanodisc, thus in a native-like lipid bilayer, enable more biologically relevant conditions[17]. So therefore, using the concept as described in Steyaert et al. (WO2019/086548A1), MegaBodies were designed and generated to specifically bind these nanodiscs which contain a membrane protein of interest, so as to apply these MegaBodies as a generic fiducial tool to evade the preferential orientation of membrane proteins reconstituted in nanodisc lipid bilayers.

So, in the below described examples, we provide novel MegaBodies, designed using the concept as described in Steyaert et al. (WO2019/086548A1), to specifically bind different compositions of Nanodiscs (MSP variants), which unexpectedly reduced preferential orientation of membrane proteins reconstituted in Nanodisc lipid bilayers, thereby bypassing the need for selection of target-specific nanobodies or MegaBodies for a particular membrane protein.

Example 1. Generation of Nanobodies Against Nanodiscs

We first generated Nanobodies that are capable of binding to different variants of MSP-constituting Nanodiscs. Accordingly, we immunised two llamas with two different membrane proteins reconstituted in Nanodiscs and generated two phage libraries, as described before[1].

For the phage display selections, we used two different MSP-based Nanodiscs, one comprising His6-TEV-MSP1D1 (SEQ ID NO:1) and the other comprising His6-TEV-MSP2N2 (SEQ ID NO:2). Purified MSP proteins were reconstituted into Nanodiscs using phosphatidylcholine lipids (POPC), as described before[2]. Phage display selection was performed using the described protocol[1]. Briefly, two different Nanodisc, MSP1 D1 and MSP2N2 were immobilized on a 96-well Maxisorp plate (2 g of the protein) in phosphate-buffer saline (PBS). After one round of biopanning with two phage libraries, fourteen Nanobody families (SEQ ID NOs: 3-16) were selected. The binding to MSP1 D1 and MSP2N2 Apo-state and Nanodisc-state was confirmed by enzyme-linked immunosorbent assay (ELISA) using periplasmic-extracts[1] (FIGS. 2A and 2B).

Example 2. Expression, Purification and Characterization of 58 kD MegaBodies Built from a c7HopQ Scaffold Inserted into the First β-Strand AB-Connecting β-Turn of Nanodisc-Specific Nanobodies We reformatted all fourteen Nanobody clones (SEQ ID NOs: 3-16) into c7HopQ-based MegaBodies as described in Steyaert et al. WO2019/086548A1, resulting in the corresponding fourteen MegaBody clones (SEQ ID NOs: 20-33), which contained: the conserved β-strand A of the N-terminus of a Nanobody (see SEQ ID NO:17), a circularly permuted c7HopQ scaffold protein (SEQ ID NO:18), the conserved β-strand B of the N-terminus of a Nanobody (SEQ ID NO:19), C-terminal part of the anti-Nanodisc Nanobodies (residues 17—the end of SEQ ID NO:3-16), 6×His/EPEA tag. Similarly, Megabodies may be built from these Nanobodies using a circularly permutated Ygjk scaffold (cYgjk or Ygjk_NO; SEQ ID NO:51) instead of c7HopQ, resulting for example, using Nb F3 (SEQ ID NO: 14) by genetic fusion of the conserved 3-strand A of the N-terminus of a Nanobody (residues 1-12 of SEQ ID NO:17), cYjgk scaffold protein (SEQ ID NO:51), the conserved β-strand B of the N-terminus of a Nanobody (residues 2—the end of SEQ ID NO:19), C-terminal part of the anti-Nanodisc Nanobodies (residues 17—the end of SEQ ID NO:14) and a C-terminal 6×His/EPEA tag.

Next, we expressed these fourteen anti-Nanodisc MegaBody clones (SEQ ID NOs:20-33) in the periplasm of *E. coli* and purified to homogeneity using NiNTA affinity chromatography followed by size exclusion chromatography (Superdex 200 PG 10/300 column) as described in Steyaert et al. WO2019/086548A1 (e.g. purified $Mb_{NbF3}^{c7HopQ}$ MegaBody in FIGS. 10A and 10B). The functional properties of the purified MegaBodies (SEQ ID NOs: 20-33) were analysed by ELISA. $Mb_{Nb25}^{c7HopQ}$ specifically binding β3-$GABA_AR$ (SEQ ID NO: 34) was used as a negative control for anti-Nanodisc binding. Purified MSP1 D1 (SEQ ID NO:1) and MSP2N2 (SEQ ID NO:2) in Apo- and Nanodisc-state were immobilized in the wells of a maxisorp microtitre plate at a concentration of 1 μg/mL in 100 μL of PBS per well. Residual protein binding sites in the wells were blocked for two hours at room temperature with 4% milk in PBS. Purified MegaBody samples were incubated on Apo/Nanodisc coated and on non-coated wells. After washing steps, the binding of MegaBodies to both types Nanodiscs was examined by using the CaptureSelect biotinylated antibody (Life Technologies) that specifically recognizes the EPEA-tag, present only on the MegaBody. Subsequent detection of Capture Select biotinylated antibody was done with Streptavidin-Alkaline phosphatase (Promega). The absorption at 405 nm was measured after adding the enzyme substrate p-nitrophenyl phosphate. Detected signals show at least 4-fold higher signals of each MegaBody comparing a condition with immobilized MSP1 D1/MSP2N2 in Apo- or Nanodisc-state to no MSP (FIGS. 3A and 3B). The ELISA results indicate that the purified recombinant MegaBodies (SEQ ID NOs: 20-33) can be purified to homogeneity and are capable to specifically bind and form a complex with both, MSP1 D1 and MSP2N2 in Apo- and Nanodisc-state.

Further validation of the MegaBody binding to several variants was obtained by testing a representative anti-Nanodisc $Mb_{NbF3}{}^{c7HopQ}$ MegaBody clone (SEQ ID NO: 31; FIGS. 10A and 10B) to a further MSP variant, MSP1 E3D1, as depicted in FIG. 9*a*, and with the ELISA result shown in FIG. 9*b*, allowing to conclude that the Nanobodies or MegaBodies selected for binding to MSP1 D1 and MSP2N2, both MSP proteins comprising the amino acid residues of H0.5 and H2-H10 of the Apo Al protein, are also capable to bind other MSP variants, such as MSP1 E3D1, wherein shuffled, truncated or repeated parts of the Apo Al H-modules (as for instance depicted in FIG. 4 and Table 1 of Denisov and Sligar (2017).

To further validate the binding kinetics of a representative anti-Nanodisc $Mb_{NbF3}{}^{c7HopQ}$ MegaBody clone (SEQ ID NO: 31) to one particular variant of the Nanodisc belt proteins (MSP1D1 in Apo-state, SEQ ID NO: 1), we performed real-time kinetic analysis using bio-layer interferometry. For immobilization on the biosensors, purified MSP1 D1 in Apo-state was biotinylated with a five-fold molar excess of EZ-link NHS-Biotin (Thermo Fisher Scientific) following the manufacturer's instructions and separated from unreacted NHS-biotin on a NAP10 column (GE Healthcare). The biotin/MSP1D1 ratio was determined using the Pierce Biotin Quantitation kit (Thermo Fisher Scientific). Next, the biotinylated MSP1 D1 was diluted to 0.75 μg/ml in PBS supplemented with 1 mg/mL BSA and directly immobilised on Streptavidin (SA) biosensors at about 1 nm response. After two equilibration steps of 300 s, the binding isotherms were monitored by exposing separate sensors simultaneously to different concentrations of $Mb_{NbF3}{}^{c7HopQ}$ MegaBody. Association kinetics were followed for 300 s at 30° C. under constant stirring at 1000 rpm, tailed by dissociation experiments for 400 s. Association and dissociation rates were estimated by fitting the sensograms using the 1:2 binding model included in the Octet Data Analysis software 9.1 (ForteBio). The representative binding kinetics data for $Mb_{F3}{}^{c7HopQ}$ MegaBody (SEQ ID NO:31) is shown in FIG. 4. Performed measurements confirm the $Mb_{F3}{}^{c7HopQ}$ MegaBody binds to the MSP1D1-containing Nanodisc, with the affinity of 23.5 nM.

Example 3. Characterization of MegaBody·Nanodisc Complex Stoichiometry

To reveal the binding stoichiometry of $Mb_{F3}{}^{c7HopQ}$ MegaBody (SEQ ID NO:31), thus the number of binding sides in MSP1 D1 Nanodisc belts, we performed the high-performance liquid chromatography (HPLC) coupled with multi-angle light scattering (MALS) analysis. Accordingly, purified MSP1 D1 and MSP2N2 Nanodiscs were loaded on a size exclusion SEC-3 column (Agilent Technologies) separately, or in a complex with anti-Nanodisc $Mb_{F3}{}^{c7HopQ}$ MegaBody (SEQ ID NO:31). Unique elution peaks were next analyzed by MALS to experimentally calculate the molecular weight of MSP1 D1 Nanodisc only or in the complexes with $Mb_{F3}{}^{c7HopQ}$ MegaBody clone (FIG. 5). The theoretical molecular weight of MSP1 D1 Nanodisc with POPC lipids (two MSP1 D1 and 62 POPC lipids per one Nanodisc[39]) is 96.452 kDa, whereas of $Mb_{F3}{}^{c7HopQ}$ is 54.977 kDa. The experimentally calculated molecular masses revealed that the Nanodisc·$Mb_{F3}{}^{c7HopQ}$ MegaBody complex is formed in 1:2 molar ratio (FIG. 5).

To further validate the binding stoichiometry calculated by MALS experiments, the Nanodisc-$Mb_{F3}{}^{c7HopQ}$ MegaBody complex is analysed by Transmission Electron Microscope using negative staining. Accordingly, the purified MSP1 D1 Nanodisc·$Mb_{F3}{}^{c7HopQ}$ MegaBody complex is diluted to 0.1 mg/ml with PBS. Aliquots (~3 μl) are adhered to thin PELCO® TEM formvar/carbon-coated 400-mesh copper grids (Support Films), which had been rendered hydrophilic by glow discharge for 30 s. After incubating for ~30 s, the grids are rapidly washed with three successive drops of deionized water (20 μl each) and then exposed to three successive drops of 2% (w/v) uranyl formate (UF) pH 4.6. The excess solution is removed with filter paper from the backside of the grids, after which the specimens are dried for 30 min. Next, prepared grid samples are analysed by JEOL1400+ 120 kV Transmission Electron Microscope. Micrographs are acquired under the low-dose mode (maximal dose, 30 e/Å$^2$) at a magnification of 50,000 with a Gatan lens-coupled 4 k×4 k high-resolution charge-coupled device (UltraCam). The negative stain experiment is to confirm the MSP1D1: $Mb_{F3}{}^{c7HopQ}$ MegaBody binding ratio as 1:2.

Example 4. Cryo-EM Studies of $GABA_AR$-β Reconstituted in MSP2N2 Nanodiscs and the Impact of anti-$GABA_AR$-β3 Nanobody Nb25 and MegaBody $Mb_{Nb25}{}^{c7HopQ}$ $GABA_A$ receptors ($GABA_ARs$) are pentameric ligand gated ion channels (pLGICs) which mediate fast inhibitory signalling in human brain and are targets for clinically-relevant drugs including benzodiazepines and general anaesthetics[3]. In single particle cryo-EM applications, $GABA_ARs$ and related pLGICs adopt preferential orientations in free-standing ice unless detergent is present to shield the protein from interactions with the water-air interface. However, the use of detergent can negatively impact on the structural integrity of heteromeric $GABA_ARs$ obscuring their conformational state interpretation[45]. In addition, detergent solubilized $GABA_AR$ samples need to be highly concentrated (5-6 mg/ml)[5] to achieve sufficient particle numbers per micrograph in free-standing ice when compared to what is required for other membrane protein samples in amphipols or nanodiscs (0.3-0.5 mg/ml)[6,7]. Therefore, if the preferential orientation problem for $GABA_ARs$ was solved without the use of detergents, this would allow their structural analysis in native-like lipid bilayer systems at the fraction of the cost.

First, we aimed to analyze the distribution of $GABA_AR$-β3:MSP2N2 Nanodisc particles alone or in a complex with Nanobody Nb25 (SEQ ID NO: 36) and MegaBody $Mb_{Nb25}{}^{c7HopQ}$ (SEQ ID NO: 34), which both specifically interact with the extracellular domain (ECD) of the $GABA_AR$ (3 subunit via their antigen-binding domain. The Nb25 was previously applied as a crystallization chaperone for homomeric $GABA_ARs$[8].

We first expressed the human $GABA_AR$-β33 (SEQ ID NO: 35), which contains a single point mutation K279T (UniProtKB P28472), an SQPARAA linker[9] substituting the M3-M4 loop, and a C-terminal 1 D4-tag (TETSQVAPA)[10] was transiently expressed in HEK293S-GnTI$^-$ cells as described before[11]. Briefly, HEK293S-GnTI$^-$ cells were grown in protein expression medium (PEM, Thermo Fisher Scientific) supplemented with 1% fetal bovine serum (Invitrogen) at 37° C. and 8% $CO_2$. At a density of ~2×10$^6$ cells/ml, cells were transfected with DNA-PEI transfection mix and 48 h post-transfection cells were harvested by centrifugation at 4,000 g, 4° C. Cell pellets were snap-frozen in liquid $N_2$ and stored at ~80° C. for future use.

Next, we reconstituted purified human $GABA_AR$-β (SEQ ID NO: 35) into MSP2N2 Nanodiscs (SEQ ID NO:2). Accordingly, each of three cell pellets from 0.8 L culture were resuspended by vortexing in dilution buffer: 50 mM HEPES pH 7.6, 300 mM NaCl, 1 mM histamine, 1% (w/v) mammalian protease inhibitor cocktail (Sigma-Aldrich). Solubilisation was performed for 1 h by adding 1% (w/v) lauryl maltose neopentyl glycol (LMNG, Anatrace) and cholesterol hemisuccinate (CHS, Anatrace) at a 10:1 (w/w) ratio. Solubilized $GABA_AR$ was separated from insoluble material by centrifugation (10,000 g, 15 min) and captured on a 1D4 affinity resin (250 pal) by slow rotation for 2 h. The resin was harvested (300 g, 5 min) and washed three times with 50 ml of washing buffer: 50 mM HEPES pH 7.6, 300 mM NaCl, 1 mM histamine (Sigma-Aldrich), 1% (w/v) LMNG and 0.1% CHS. The washed resin was equilibrated with 1 ml of dilution buffer and 240 μl of a mixture containing 80% (w/v) phosphatidylcholine (POPC, Avanti) and 20% of a bovine brain lipid (BBL) extract (Sigma-Aldrich). After 30 min incubation, the resin was equally divided to five Eppendorf tubes and collected by centrifugation. For Nanodisc reconstitution, Bio-Beads (10 mg/ml final concentration) with an excess of MSP2N2 (0.6 mg/ml final concentration) were added to each sample and incubated for 1 h rotating gently. For the conditions of $GABA_AR$-β3:MSP2N2 Nanodisc in a complex with Nb25 (SEQ ID NO: 36) and $Mb_{Nb25}{}^{c7HopQ}$ (SEQ ID NO: 34), 100 μl of Nb25 and $Mb_{Nb25}{}^{c7HopQ}$ protein samples (120 μM) were added to corresponding sample tubes and incubated for 1 h slowly rotating. Resin samples were harvested (300 g, 5 min), washed six times with dilution buffer, resuspended in 50 I of elution buffer: 12.5 mM HEPES pH 7.6, 75 mM NaCl, 0.25 mM histamine, 1.5 mM 1D4 peptide (Cube Biotech) and incubated overnight. Resins were pelleted by centrifugation (300 g, 5 min) to collect the supernatants. These supernatants were supplemented once more with 0.4 μl of ~120 μM of Nb25 and $Mb_{Nb25}{}^{c7HopQ}$ respectively to be used for cryo-EM grid preparation. Accordingly, 3.5 μl of the receptor alone, in complex with Nb25 and $Mb_{Nb25}{}^{c7HopQ}$ were applied onto glow-discharged gold R1.2/1.3 300 mesh UltraAuFoil grids (Quantifoil) for 30 s and blotted for 5.5 s before vitrification in liquid ethane. A Vitrobot Mark IV (Thermo Fisher Scientific) was used for plunge-freezing at ~100% humidity and 14.5° C.

Cryo-EM data off all samples were collected on a 300 kV Titan Krios microscope (Thermo Fisher Scientific) using a Falcon 3EC (Thermo Fisher Scientific) direct electron detector in counting mode and a Volta Phase Plate (VPP, Thermo Fisher Scientific). Data collection parameters are show in Table 1.

In order to investigate the proportion of preferential particle views of β3 $GABA_AR$ particles in samples, where β3 homomer was alone or complexed with Nb25 and $Mb_{Nb25}{}^{c7HopQ}$, small cryo-EM datasets were analysed by using the same basic data processing procedure. First, MotionCor2[12] was used to motion-correct the movies and Warp[13] was applied to estimate the contrast transfer function (CTF), phase shift parameters and to pick, and extract particles. The reference-free 2D classification was performed using RELION 3.0[14]. One round of 2D classification was performed and well-aligned 2D classes showing clear $GABA_AR$ particle projections were used to determine the proportion of preferred particle orientations in each sample (around 6,000 particles for each of the four conditions). Next, the particles from the 2D classification were subjected to reference-free 3D model generation and 3D refinement using cryoSPARC[15]. The efficiency of the particle orientation distribution ($E_{od}$ values) for each 3D model was calculated using cryoEF[16].

Based on the obtained results for $GABA_AR$-β3:MSP2N2 Nanodisc particles alone or in a complex with Nanobody Nb25 (SEQ ID NO: 36) and MegaBody $Mb_{Nb25}{}^{c7HopQ}$ (SEQ ID NO: 34), we were able to evaluate the extent of the preferential particle orientation in free-standing ice in each condition (FIGS. 6A-6C). When $GABA_AR$-β3:MSP2N2 Nanodisc particles were frozen alone, ~84% of the views were observed with the symmetry axis of the protein perpendicular to the vitreous ice layer ("top" views, FIG. 6*a*). The receptor sample in complex with Nb25 also presented a similar fraction of the "top" views (FIG. 6*b*). In both cases 3D reconstructions resulted in severely anisotropic maps with major Fourier space gaps and low particle distribution "efficiencies" ($E_{od}$). Most remarkably, the $GABA_AR$-β3:MSP2N2 Nanodisc in a complex with $Mb_{Nb25}{}^{c7HopQ}$ showed largely improved distribution of orientations with ~77% of particles representing "side" views (FIG. 6*c*). This in turn allowed the reconstruction of a 3D map with 3-fold higher angle distribution "efficiency" and mostly isotropic features. It thus appears that only the $Mb_{Nb25}{}^{c7HopQ}$ MegaBody directly improve the distribution of $GABA_AR$-β3:MSP2N2 Nanodisc particle orientations.

Example 5: Validation of Anti-Nanodisc MegaBodies Impact in Cryo-EM Studies of $GABA_AR$-β3 Reconstituted in MSP2N2 Nanodiscs In Example 4, MegaBody $Mb_{Nb25}{}^{c7HopQ}$, which interact with the extracellular domain (ECD) of the $GABA_AR$ β3 subunit, was shown to directly improve the distribution of $GABA_AR$-β3:MSP2N2 Nanodisc particle orientations. Built on these results, we decided to assess the utility of an anti-Nanodisc MegaBody as a generic tool for single particle cryo-EM structural studies of any membrane protein in Nanodisc. Therefore, we aimed to analyse the distribution of $GABA_AR$-β3:MSP2N2 Nanodisc particles in a complex with $Mb_{F3}{}^{c7HopQ}$ MegaBody (SEQ ID NO: 31), which binds MSP1 D1 and MSP2N2 Nanodisc with high affinity.

Figure 8F:
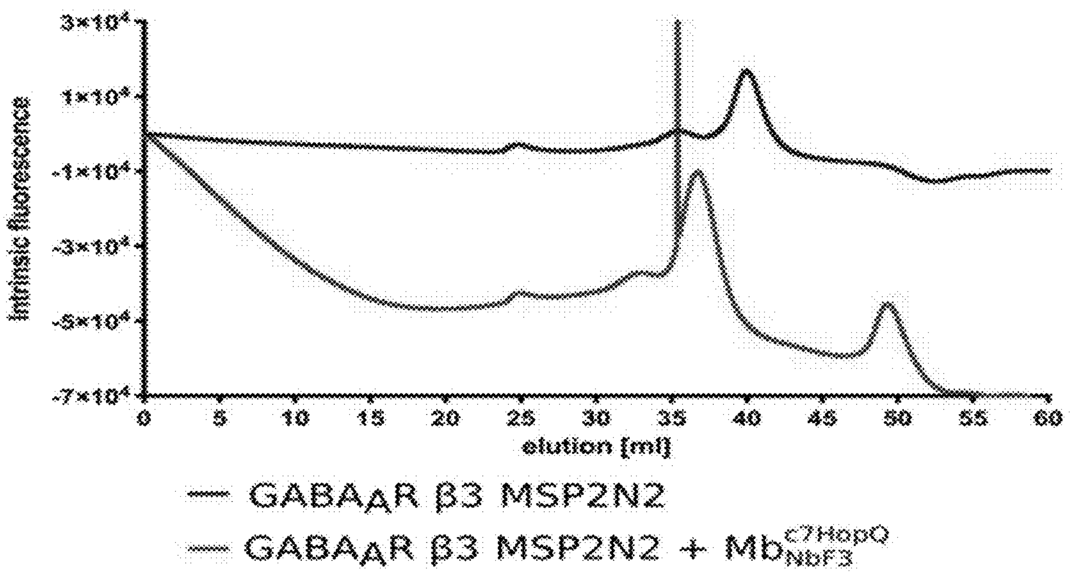

We first validated that $Mb_{F3}{}^{c7HopQ}$ MegaBody forms a stable complex with MSP2N2 Nanodisc in a gel-filtration experiment (FIG. 7, size exclusion SEC-3 column, Agilent Technologies). Next, to perform cryo-EM studies of $GABA_AR$-β3:MSP2N2 Nanodisc in a complex with anti-Nanodisc $Mb_{F3}{}^{c7HopQ}$ MegaBody (SEQ ID NO: 31), the receptor was purified and reconstituted in MSP2N2 Nanodisc as described above, without addition of MegaBody or Histamine during this procedure. After the elution step with 1 D4 peptide, the Histamine (final concentration 1 mM) and MegaBody $Mb_{F3}^{c7HopQ}$ (final concentration 6 μM) were added to the purified GABA$_A$R-β3:MSP2N2 Nanodisc sample (final concentration 0.9 μM) and incubated for 30 min before for cryo-EM grid preparation (FIG. 8*f*). Next, 3.5 μl of this sample was applied onto glow-discharged gold R 2/2 300 mesh grids (Quantifoil) for 30 s and blotted for 3.5 s before vitrification in liquid ethane. A Leica Automatic Plunge Freezer EM GP2 was used for plunge-freezing at ~95% humidity and 14° C. 300 kV Titan Krios microscope (Thermo Fisher Scientific) and a Gatan K2 direct electron detector were used to 200 micrographs of this sample. Cryo-EM data collection parameters are show in Table 1.

First, MotionCor2[12] was used to motion-correct the movies and Warp[13] was applied to estimate the contrast transfer function (CTF), phase shift parameters and to pick, and extract particles. The representative micrograph (denoised by CryoSPARC) is shown in FIGS. 8A-8F. The anti-Nanodisc $Mb_{F3}^{c7HopQ}$ MegaBody bound to the GABA$_A$R-β3:MSP2N2 Nanodisc particles is indicated by arrows. The reference-free 2D classification was performed using CryoSPARC. Remarkably, the 2D classes contained well-aligned GABA$_A$R-β3:MSP2N2 Nanodisc particles, where the alignment was not influenced by $Mb_{F3}^{c7HopQ}$ MegaBody. Additionally, more than 90% of the particle views were observed as "side" views (around 14,000 particles analyzed), which are the most informative for the high-resolution reconstruction. Accordingly, particles from presented 2D classes were selected for reference-free 3D model (CryoSPARC). A 'gold standard' 3D-refinement was performed, yielding the final cryoEM map of 3.0 Å resolution (FSC criteria of 0.143, FIGS. 8A-8F) with the "efficiency" value $E_{od}$=0.69.

These results prove that anti-Nanodisc $Mb_{NbF3}^{c7Hop}$ MegaBodies improve the particle orientation of GABA$_A$R in free-standing ice, maintaining is native structure. Therefore, we conclude that these generic MegaBody tools comparably improve structural resolution obtained in cryo-EM as for the GABA$_A$R-β3-specific $Mb_{Nb25}^{c7HopQ}$ MegaBodies.

TABLE 1

Cryo-EM data collection, refinement and validation statistics.

| | β3 GABA$_A$R alone and in Nb25/ $Mb_{Nb25}^{c7HopQ}$ complex | β3 GABA$_A$R – $Mb_{NbF3}^{c7HopQ}$ complex |
|---|---|---|
| Data collection and processing | | |
| Microscope, location | Krios-II, MRC-LMB | Krios-II 2G, MRC-LMB |
| Magnification | 75,000 | 165,000 |
| Voltage (kV) | 300 | 300 |
| Detector | Falcon 3EC with VPP | Gatan K2 |
| Energy filter, slit | | Gatan Imaging Filter, 20 eV slit |
| Electron Dose ($e^-$/Å$^2$) | 30 | 65 |
| Exposure time (s) | 60 | 8 |
| Pixel Size (Å) | 1.07 | 0.705 |
| Dose rate ($e^-$/pixel/s) | 0.4 | 4.038 |
| Frame number | 75 | 40 |
| Defocus Range (μm) | −0.7 to −0.5 | 0.5 to 1.5 |
| Micrographs collected (no.) | 20 -700 | 200 |
| Micrographs selected (no.) | | 193 |
| Initial particle images (no.) | | 23,431 |
| Final particle images (no.) | | 8,818 |
| Symmetry imposed | | C5 |
| Map resolution (Å) | | 3.0 |
| FSC threshold | | 0.143 |

Aspects of the Disclosure

1. An antigen-binding chimeric protein comprising an antigen-binding domain fused to a scaffold protein, wherein the antigen-binding domain comprises an immunoglobulin (Ig) domain, and wherein the scaffold protein is inserted in the first β-turn that connects β-strand A and B of said Ig domain as defined according to IMGT nomenclature, further characterized in that said antigen-binding domain specifically binds a nanodisc belt protein.
2. The antigen-binding chimeric protein of aspect 1, wherein the scaffold protein has a total molecular mass of at least 30 kDa.
3. The antigen-binding chimeric protein of aspects 1 or 2, wherein the scaffold protein is a labelled protein.
4. The antigen-binding chimeric protein of any of aspects 1 to 3, wherein said antigen-binding chimeric protein binds a nanodisc belt protein in its nanodisc-bound state.
5. The antigen-binding chimeric protein of aspects 1 to 4, wherein said nanodisc belt protein is a membrane-scaffold protein (MSP) or an MSP variant.
6. The antigen-binding chimeric protein of aspect 5, wherein said MSP or MSP variant comprises a truncated or engineered form of apolipoprotein (apo) A-I.
7. The antigen-binding domain specifically binding a nanodisc belt protein, wherein said antigen-binding domain is a nanobody.
8. A nucleic acid molecule encoding the antigen-binding chimeric protein of any of aspects 1 to 6, or the antigen-binding domain of aspect 7.
9. A vector comprising the nucleic acid molecule of aspect 8.
10. The vector according to aspect 9, for expression in prokaryotic or eukaryotic cells, or for surface display in yeast, phages, bacteria, or viruses.
11. A host cell, comprising the antigen-binding chimeric protein of any one of aspects 1 to 6, or the antigen-binding domain of aspect 7, or the nucleic acid of aspect 8, or the vector of aspects 9 or 10.
12. A host cell according to aspect 11, wherein said antigen-binding chimeric protein and the nanodisc belt protein are present.
13. A complex comprising,
    a. the antigen-binding chimeric protein of any of aspects 1 to 6, or the antigen-binding domain of aspect 7, and
    b. a nanodisc, wherein said nanodisc comprises nanodisc belt proteins, and wherein said antigen-binding chimeric protein or antigen-binding domain of (a) is bound to said nanodisc belt proteins.
14. The complex of aspect 13, further comprising a membrane protein present within said nanodisc.
15. A method of determining a 3-dimensional structure of a membrane protein comprising the steps of:
    a. Assembling a nanodisc comprising a membrane protein, and
    b. Incubating said nanodisc of step a. with the antigen-binding chimeric protein of any of aspects 1 to 6, or with the antigen-binding domain of aspect 7, to form a complex, and
    c. display said complex in suitable conditions for structural analysis, wherein the nanodisc of step (a) comprises a nanodisc belt protein specifically binding the antigen-binding chimeric protein or antigen-binding domain of step (b), and wherein the 3D structure of said membrane target protein is determined at high-resolution.
16. The use of the antigen-binding chimeric protein of aspects 1 to 6, the antigen-binding domain of aspect 7, the nucleic acid molecule of aspect 8, the vectors of aspects 9-10, the host cell of aspects 11-12, or the complex of aspects 13-14, for structural analysis of a membrane protein present in a nanodisc.

17. The use of the antigen-binding chimeric protein or the antigen-binding domain according to aspect 16, wherein said structural analysis comprises single particle cryo-EM or crystallography.

Sequence Listing

>SEQ ID NO: 1: His6-TEV-MSP1 D1 (CA15914)
(6xHistag, TEV cleavage site. MSP1D1)
MGHHHHHHHDYDIPTTENLYFQGSTFSKLREQLGPVTQEFWDNLEKETE

GLRQEMSKDLEEVKAKVQPYLDDFQKKWQEEMELYRQKVEPLRAELQEGA

RQKLHELQEKLSPLGEEMRDRARAHVDALRTHLAPYSDELRQRLAARLEA

LKENGGARLAEYHAKATEHLSTLSEKAKPALEDLRQGLLPVLESFKVSFL

SALEEYTKKLNTQ

SEQ ID NO: 2: His6-TEV-MSP2N2 (CA15915) (6×His tag, TEV cleavage site, MSP2N2)
SEQ ID NO: 3: MP1521_B9 Nanobody (CA15883) (Nanobody, 6×His tag, EPEA tag)
SEQ ID NO: 4: MP1521_G9 Nanobody (CA15884) (Nanobody, 6×His tag, EPEA tag)
SEQ ID NO: 5: MP1522_A12 Nanobody (CA15885) (Nanobody, 6×His tag, EPEA tag)
SEQ ID NO: 6: MP1522_B7 Nanobody (CA15886) (Nanobody, 6×His tag, EPEA tag)
SEQ ID NO: 7: MP1522_E8 Nanobody (CA15887) (Nanobody, 6×His tag, EPEA tag)
SEQ ID NO: 8: MP1522_B9 Nanobody (CA15888) (Nanobody, 6×His tag, EPEA tag)
SEQ ID NO: 9: MP1521_E4 Nanobody (CA15889) (Nanobody, 6×His tag, EPEA tag)
SEQ ID NO: 10: MP1521_H5 Nanobody (CA15890) (Nanobody, 6×His tag, EPEA tag)
SEQ ID NO: 11: MP1522_C10 Nanobody (CA15891) (Nanobody, 6×His tag, EPEA tag)
SEQ ID NO: 12: MP1522_A5 Nanobody (CA15892) (Nanobody, 6×His tag, EPEA tag)
SEQ ID NO: 13: MP1521_B4 Nanobody (CA15893) (Nanobody, 6×His tag, EPEA tag)
SEQ ID NO: 14: MP1521_F3 Nanobody (CA15894) (Nanobody, 6×His tag, EPEA tag)
SEQ ID NO: 15: MP1521_B1 Nanobody (CA15895) (Nanobody, 6×His tag, EPEA tag)
SEQ ID NO: 16: MP1521_E1 Nanobody (CA15896) (Nanobody, 6×His tag, EPEA tag)
SEQ ID NO: 17: conserved β-strand A of a Nanobody
SEQ ID NO: 18: circularly permutated c7HopQ variant of *Helicobacter pylori* strain G27 HopQ adhesin domain protein
SEQ ID NO: 19: conserved 3-strand B of a Nanobody > SEQ ID NO: 20: MD$_{Nb1_B9}^{c7HopQ}$ MegaBody (CA15898)
(Nanobody MP1521_B9 sequence, c7HopQ in bold, 6xHis tag, EPEA tag in italics)
QVQLVESGGGLVQTKTTTSVIDTTNDAQNLLTQAQTIVNTLKDYCPILIA

KSSSSNGGTNNANTPSWQTAGGGKNSCATFGAEFSAASDMINNAQKIVQE

TQQLSANQPKNITQPHNLNLNSPSSLTALAQKMLKNAQSQAEILKLANQV

ESDFNKLSSGHLKDYIGKCDASAISSANMTMQNQKNNWGNGCAGVEETQS

-continued

LLKTSAADFNNQTPQINQAQNLANTLIQELGNNTYEQLSRLLTNDNGTNS

KTSAQAINQAVNNLNERAKTLAGGTTNSPAYQATLLALRSVLGLWNSMGY

AVICGGYTKSPGENNQKDFHYTDENGNGTTINCGGSTNSNGTHSYNGTNT

LKADKNVSLSIEQYEKIHEAYQILSKALKQAGLAPLNSKGEKLEAHVTTS

KYGSLRLSCAASGRTLCSIPMGWFRQAPGKEREFVAAIRWSGGSTYYADS

VKGRFSISKDNAKNTVYLQMNNLKPEDTATYYCASAAPYSSWSRGLEYDY

WGQGTQVTVSS*hhhhhhepea*

SEQ ID NO: 21: Mb$_{NbG9}^{c7HopQ}$ MegaBody (CA15899) (Nanobody MP1521_G9 sequence, c7 op in bold, 6×His tag, EPEA tag)
SEQ ID NO: 22: Mb$_{NbA12}^{c7HopQ}$ MegaBody (CA15900) (Nanobody MP1522_A12 sequence, c7HopQ in bold, 6×His tag, EPEA tag)
SEQ ID NO: 23: Mb$_{NbB7}^{c7HopQ}$ MegaBody (CA15901) (Nanobody MP1522_B7 sequence, c7HopQ in bold, 6×His tag, EPEA tag)
SEQ ID NO: 24: Mb$_{NbE8}^{c7HopQ}$ MegaBody (CA15902) (Nanobody MP1522_E8 sequence, c7HopQ in bold, 6×His tag, EPEA tag)
SEQ ID NO: 25: Mb$_{Nb2_B9}^{c7HopQ}$ MegaBody (CA15903) (Nanobody MP1522_B9 sequence, c7HopQ in bold, 6×His tag, EPEA tag)
SEQ ID NO: 26: Mb$_{NbE4}^{c7HopQ}$ MegaBody (CA15191) (Nanobody MP1521_E4 sequence, c7HopQ in bold, 6×His tag, EPEA tag)
SEQ ID NO: 27: Mb$_{NbH5}^{c7HopQ}$ MegaBody (CA15904) (Nanobody MP1521_H5 sequence, c7HopQ in bold, 6×His tag, EPEA tag)
SEQ ID NO: 28: Mb$_{NbC10}^{c7HopQ}$ MegaBody (CA15905) (Nanobody MP1522_C10 sequence, c7HopQ in bold, 6×His tag, EPEA tag)
SEQ ID NO: 29: Mb$_{NbA5}^{c7HopQ}$ MegaBody (CA15906) (Nanobody MP1522_A5 sequence, c7HopQ in bold, 6×His tag, EPEA tag)
SEQ ID NO: 30: Mb$_{NbB4}^{c7HopQ}$ MegaBody (CA15907) (Nanobody MP1521_B4 sequence, c7HopQ in bold, 6×His tag, EPEA tag)
SEQ ID NO: 31: Mb$_{NbF3}^{c7HopQ}$ MegaBody (CA15192) (Nanobody MP1521_F3 sequence, c7HopQ in bold, 6×His tag, EPEA tag)
SEQ ID NO: 32: Mb$_{NbB1}^{c7HopQ}$ MegaBody (CA15908) (Nanobody MP1521_B1 sequence, c7HopQ in bold, 6×His tag, EPEA tag)
SEQ ID NO: 33: Mb$_{NbE1}^{c7HopQ}$ MegaBody (CA15909) (Nanobody MP1521_E1 sequence, c7HopQ in bold, 6×His tag, EPEA tag)
SEQ ID NO: 34: MegaBody Mb$_{Nb25}^{c7HopQ}$ against GABA$_A$R-β

>SEQ ID NO: 35: human GABA$_A$R-β3 with C-terminal 1D4tag
(human GABA$_A$R-β3 SEQUENCE, 1D4tag in bold)
QSVNDPGNMSFVKETVDKLLKGYDIRLRPDFGGPPVCVGMNIDIASIDMV

SEVNMDYTLTMYFQQYWRDKRLAYSGIPLNLTLDNRVADQLWVPDTYFLN

DKKSFVHGVTVKNRMIRLHPDGTVLYGLRITTTAACMMDLRRYPLDEQNC

TLEIESYGYTTDDIEFYWRGGDKAVTGVERIELPQFSIVEHRLVSRNWFA

TGAYPRLSLSFRLKRNIGYFILQTYMPSILITILSWVSFWINYDASAARV

-continued

```
ALGITTVLTMTTINTHLRETLPKIPYVTAIDMYLMGCFVFVFLALLEYAF

VNYIFFSQPARAAAIDRWSRIVFPFTFSLFNLVYWLYYVNgaTETSQVAP

A
```

SEQ ID NO: 36: Nanobody Nb25 against $GABA_AR$-β3 (CA8125)(Nanobody sequence, x is ag, EPEA tag)

SEQ ID NO: 37-50: Nanobody sequences as depicted in SEQID NO:3-16 without the 6×His/EPEA tag.

SEQ ID NO: 51: circular permutated *E.coli* Ygjk protein (PDB 3WFS; Ygjk_NO)

>SEQ ID NO: 52: $MD_{NbF3}^{Ygjk\_NO}$ MegaBody (Nanobody MP1521_F3 sequence, Ygjk_NO underlined), 6xHis tag, EPEA tag in italics)

```
QVQLVESGGGLVKEETQSGLNNYARVVEKGQYDSLEIPAQVAASWESGRD

DAAVFGFIDKEQLDKYVANGGKRSDWTVKFAENRSQDGTLLGYSLLQESV

DQASYMYSDNHYLAEMATILGKPEEAKRYRQLAQQLADYINTCMFDPTTQ

FYYDVRIEDKPLANGCAGKPIVERGKGPEGWSPLFNGAATQANADAVVKV

MLDPKEFNTFVPLGTAALTNPAFGADIYWRGRVWVDQFWFGLKGMERYGY

RDDALKLADTFFRHAKGLTADGPIQENYNPLTGAQQGAPNFSWSAAHLYM

LYNDFFRKQasgggsggggsggggsgNADNYKNVINRTGAPQYMKDYDYD

DHQRFNPFFDLGAWHGHLLPDGPNTMGGFPGVALLTEEYINFMASNFDRL

TVWQDGKKVDFTLEAYSIPGALVQKLTAKDVQVEMTLRFATPRTSLLETK

ITSNKPLDLVWDGELLEKLEAKEGKPLSDKTIAGEYPDYQRKISATRDGL

KVTFGKVRATWDLLTSGESEYQVHKSLPVQTEINGNRFTSKAHINGSTTL

YTTYSHLLTAQEVSKEQMQIRDILARPAFYLTASQQRWEEYLKKGLTNPD

ATPEQTRVAVKAIETLNGNWRSPGGAVKFNTVTPSVTGRWFSGNQTWPWD

TWKQAFAMAHFNPDIAKENIRAVFSWQIQPGDSVRPQDVGFVPDLIAWNL

SPERGGDGGNWNERNTKPSLAAWSVMEVYNVTQDKTWVAEMYPKLVAYHD

WWLRNRDHNGNGVPEYGATRDKAHNTESGEMLFTVKKSLRLSCAASGSGF

GPNVMGWYRQAPGKRRELVATINRIGNINYGDSVKGRFTLSREIAVNTVY

LQMNSLKPEDAANYYCYAAKYGVDYWGKGTQVTVSShhhhhhepea
```

SEQ ID NO: 53-67: MegaBody sequences as depicted in SEQ ID NOs:20-33 and 52 without the 6His/EPEA tag.

SEQ ID NO: 68: MSP1E1D3 MSP variant

SEQ ID NO: 69: human Apolipoprotein A-I (P0264)

>SEQ ID NO: 70: circular permutated HopQ (cHopQ)

```
TKTTTSVIDTTNDAQNLLTQAQTIVNTLKDYCPILIAKSSSSNGGTNNAN

TPSWQTAGGGKNSCATFGAEFSAASDMINNAQKIVQETQQLSANQPKNIT

QPHNLNLNSPSSLTALAQKMLKNAQSQAEILKLANQVESDFNKLSSGHLK

DYIGKCDASAISSANMTMQNQKNNWGNGCAGVEETQSLLKTSAADFNNQT

PQINQAQNLANTLIQELGNNPFRasgggsggggsgKLSDTYEQLSRLLTN

DNGTNSKTSAQAINQAVNNLNERAKTLAGGTTNSPAYQATLLALRSVLGL

WNSMGYAVICGGYTKSPGENNQKDFHYTDENGNGTTINCGGSTNSNGTHS

YNGTNTLKADKNVSLSIEQYEKIHEAYQILSKALKQAGLAPLNSKGEKLE

AHVTTSKY
```

SEQ ID NO:71: circular permutated HopQ wherein the linker and 7 amino acids are truncated (underlined in SEQ ID NO:70) (c7HopQ)

REFERENCES

1. Pardon, E. et al. A general protocol for the generation of Nanobodies for structural biology. Nat. Protoc. 9, 674-693 (2014).
2. Grinkova, Y. V, Denisov, I. G. & Sligar, S. G. Engineering extended membrane scaffold proteins for self-assembly of soluble nanoscale lipid bilayers. Protein Eng. Des. Sel. 23, 843-848 (2010).
3. Sigel, E. & Steinmann, M. E. Structure, Function, and Modulation of GABA A. J. Biol. Chem. 287, 40224-40231 (2012).
4. Phulera, S. et al. Cryo-EM structure of the benzodiazepine-sensitive α1β1γ2S tri-heteromeric $GABA_A$ receptor in complex with GABA. Elife 7, e39383 (2018).
5. Laverty, D. et al. Cryo-EM structure of the human α1β3γ2 $GABA_A$ receptor in a lipid bilayer. Nature 565, 516-520 (2019).
6. Liao, M., Cao, E., Julius, D. & Cheng, Y. Structure of the TRPV1 ion channel determined by electron cryo-microscopy. Nature 504, 107-112 (2013).
7. Gao, Y., Cao, E., Julius, D. & Cheng, Y. TRPV1 structures in nanodiscs reveal mechanisms of ligand and lipid action. Nature 1-17 (2016). doi:10.1038/nature17964
8. Miller, P. S. et al. Structural basis for GABA A receptor potentiation by neurosteroids. Nat. Struct. Mol. Biol. 24, 986-992 (2017).
9. Jansen, M., Bali, M. & Akabas, M. H. Modular design of Cys-loop ligand-gated ion channels: functional 5-HT3 and GABA rho1 receptors lacking the large cytoplasmic M3M4 loop. J. Gen. Physiol. 131, 137-146 (2008).
10. Molday, R. S. & Mackenzie, D. Monoclonal Antibodies to Rhodopsin: Characterization, Cross-Reactivity, and Application as Structural Probest. Biochemistry 22, 653-660 (1983).
11. Miller, P. S. & Aricescu, A. R. Crystal structure of a human GABA A receptor. Nature 512, 270-275 (2014).
12. Zheng, S. Q. et al. MotionCor2: anisotropic correction of beam-induced motion for improved cryo-electron microscopy. Nat. Publ. Gr. 1-2 (2017). doi:10.1038/nmeth.4193
13. Langer, G., Cohen, S. X., Lamzin, V. S. & Perrakis, A. Automated macromolecular model building for X-ray crystallography using ARP/wARP version 7. Nat. Protoc. 3, 1171-1179 (2008).
14. Zivanov, J. et al. New tools for automated high-resolution cryo-EM structure determination in RELION-3. Elife 7, e42166 (2018).
15. Punjani, A., Rubinstein, J. L., Fleet, D. J. & Brubaker, M. A. cryoSPARC: algorithms for rapid unsupervised cryo-EM structure determination. Nat. Methods 14, 290-297 (2017).
16. Naydenova, K. & Russo, C. J. Measuring the effects of particle orientation to improve the efficiency of electron cryomicroscopy. Nat. Commun. 8, 629 (2017).
17. Denisov, I. G. & Sligar, S. G. Nanodiscs for structural and functional studies of membrane proteins. Nat. Struct. Mol. Biol. 23, 481-486 (2016).
18. Zhu, S. et al. Structure of a human synaptic GABA A receptor. Nature 559, 67-72 (2018).
19. Lefranc, M-P. Immunoglobulin and T cell receptor genes: IMGT® and the birth of immunoinformatics. Frontiers in Immunology. 5 (22): 1-22 (2014).

20. Hagn, F. et al. Optimized phospholipid bilayer nanodiscs facilitate high-resolution structure determination of membrane proteins. J.Am.Chem. Soc., 135:1919-1925 (2013).
21. Pandit A., et al. Assembly of the major light-harvesting complex II in lipid nanodiscs. Biophys. J. (2011).
22. Rostislavleva et al. Structure and flexibility of the endosomal Vps34 complex reveals the basis of its function on membranes. Science. 350 (6257):aac7365 (2015).
23. Nogales, E. The development of cryo-EM into a mainstream structural biology technique. Nature Methods 13, 24-27 (2016).
24. Herzik, Wu, and Lander. High-resolution structure determination of sub-100 kDa complexes using conventional cryo-EM. Nature Communications 10: 1032 (2019).
25. Henderson, R. The potential and limitations of neutrons, electrons and X-rays for atomic resolution microscopy of unstained biological molecules. Quarterly reviews of biophysics. 28: 171-193 (1995).
26. Efremov, R.G., Leitner, A., Aebersold, R. & Raunser, S. Architecture and conformational switch mechanism of the ryanodine receptor. Nature 517, 39-43 (2015).
27. Gatsogiannis, C, et. al., Membrane insertion of a Tc toxin in near-atomic detail. Nat. Struct. Mol Biol. 23(10):884-890 (2016).
28. Kedrov et al. Structural Dynamics of the YidC:Ribosome Complex during Membrane Protein Biogenesis. Cell Rep. 13; 17(11):2943-2954 (2016).
29. Gao, Y. et al. TRPV1 structures in nanodiscs reveal mechanisms of ligand and lipid action. Nature, 534 (7607):347-351 (2016).
30. Shen P, Yang X, DeCaen P, Liu X, Bulkley D, Clapham D, et al. The Structure of the Polycystic Kidney Disease Channel PKD2 in Lipid Nanodiscs. Cell. 167:763-773.e11 (2016).
31. Orengo et al. Protein superfamilies and domain superfolds. Nature, 15; 372(6507):631-4 (1994).
32. Bliven, S., Prlic, A. Circular permutation in proteins. PLOS Comput. Biol. 8(3):e1002445 (2012).
33. Hagn, F., Etzkorn, M., Raschle, T. & Wagner, G. Optimized phospholipid bilayer nanodiscs facilitate high-resolution structure determination of membrane proteins. J. Am. Chem. Soc. 135, 1919-1925 (2013).
34. Park, S. H. et al. Nanodiscs versus macrodiscs for NMR of membrane proteins. Biochemistry 50, 8983-8985 (2011).
35. Wang, X., Mu, Z., Li, Y., Bi, Y. & Wang, Y. Smaller nanodiscs are suitable for studying protein lipid interactions by solution NMR. Protein J. 34, 205-211 (2015).
36. Frauenfeld et al. A saposin-lipoprotein nanoparticle system for membrane proteins. Nature Methods, 13(4): 345-51 (2016).
37. Martin, AC. The ups and downs of protein topology; rapid comparison of protein structure. Protein Eng., 13(12):829-37 (2000).
38. Scott, S. & Aricescu, A. R. A structural perspective on $GABA_A$ receptor pharmacology. Curr. Opin. Struct. Biol. 54, 189-197 (2019).
39. Bayburt, T. H. and Sligar, S. G. Single-molecule height measurements on microsomal cytochrome P450 in nanometer-scale phospholipid bilayer disks. Proc. Natl Acad. Sci. USA, 99, 6725-6730 (2002).
40. Denisov and Sligar. Nanodiscs in membrane biochemistry and biophysics (2017) Chem Rev. 117(6): 4669-4713. doi:10.1021/acs.chemrev.6b00690.
41. Denisov et al. (2007) Cooperativity in Cytochrome P450 3A4. J. of Biological chemistry. Vol 282, No. 10, pp. 7066-7076.

The invention claimed is:

1. An antigen-binding domain that specifically binds a membrane-scaffold protein (MSP) or an MSP variant, wherein the antigen-binding domain comprises an immunoglobulin single variable domain (ISVD), and the ISVD comprises an amino acid sequence selected from:

(i) any one of the amino acid sequences of SEQ ID NOs: 37-50; or (ii) a homologue thereof that is at least 95% identical to any one of the amino acid sequences of SEQ ID NOs: 37-50, provided the homologue's CDRs (Complementarity Determining Regions) are identical to the CDRs present in that same one of the amino acid sequences of SEQ ID NOs: 37-50.

2. The antigen-binding domain of claim 1, wherein said antigen-binding domain binds the MSP or MSP variant when the MSP or MSP variant is comprised in a nanodisc.

3. The antigen-binding domain of claim 1, wherein the MSP or MSP variant comprises a truncated or engineered form of apolipoprotein (apo) A-I.

4. A nucleic acid molecule encoding the antigen-binding domain of claim 1.

5. The nucleic acid molecule of claim 4, wherein the nucleic acid molecule is comprised in a vector.

6. The nucleic acid molecule of claim 5, wherein the vector is a vector for expression in prokaryotic or eukaryotic cells, or for surface display in yeast, phage, bacteria, or viruses.

7. The antigen-binding domain of claim 1, wherein the antigen-binding domain is comprised in a host cell.

8. The antigen-binding domain of claim 7, wherein the host cell comprises both the antigen-binding domain and the MSP or MSP variant.

9. A complex comprising, a. the antigen-binding domain of claim 1, and b. a nanodisc, wherein the nanodisc comprises a membrane-scaffold protein (MSP) or MSP variant, and wherein the antigen-binding domain is bound to the MSP or MSP variant protein.

10. The complex of claim 9, further comprising a membrane protein present within the nanodisc.

11. A method for determining the 3-dimensional structure of a membrane protein in a nanodisc, the method comprising:

a. incubating a sample comprising a membrane protein within a nanodisc, wherein the nanodisc comprises a membrane-scaffold protein (MSP) or MSP variant, and the antigen-binding domain of claim 1, to form a complex, b. displaying the complex in suitable conditions for structural analysis, and c. determining the 3D structure of the membrane target protein.

* * * * *

SEQUENCE LISTING

```
<160> NUMBER OF SEQ ID NOS: 71

<210> SEQ ID NO 1
<211> LENGTH: 212
<212> TYPE: PRT
<213> ORGANISM: Artificial Sequence
<220> FEATURE:
<223> OTHER INFORMATION: His6-TEV-MSP1D1 (CA15914)

<400> SEQUENCE: 1

Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125
```

-continued

```
Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210


<210> SEQ ID NO 2
<211> LENGTH: 392
<212> TYPE: PRT
<213> ORGANISM: Artificial Sequence
<220> FEATURE:
<223> OTHER INFORMATION: His6-TEV-MSP2N2 (CA15915)

<400> SEQUENCE: 2

Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Pro Val Thr Gln Glu Phe Trp Asp Asn Leu
    210                 215                 220

Glu Lys Glu Thr Glu Gly Leu Arg Gln Glu Met Ser Lys Asp Leu Glu
225                 230                 235                 240

Glu Val Lys Ala Lys Val Gln Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270
```

-continued

```
Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390


<210> SEQ ID NO 3
<211> LENGTH: 134
<212> TYPE: PRT
<213> ORGANISM: Artificial Sequence
<220> FEATURE:
<223> OTHER INFORMATION: MP1521_B9 Nanobody (CA15883)

<400> SEQUENCE: 3

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Cys Ser Ile
            20                  25                  30

Pro Met Gly Trp Phe Arg Gln Ala Pro Gly Lys Glu Arg Glu Phe Val
        35                  40                  45

Ala Ala Ile Arg Trp Ser Gly Gly Ser Thr Tyr Tyr Ala Asp Ser Val
    50                  55                  60

Lys Gly Arg Phe Ser Ile Ser Lys Asp Asn Ala Lys Asn Thr Val Tyr
65                  70                  75                  80

Leu Gln Met Asn Asn Leu Lys Pro Glu Asp Thr Ala Thr Tyr Tyr Cys
                85                  90                  95

Ala Ser Ala Ala Pro Tyr Ser Ser Trp Ser Arg Gly Leu Glu Tyr Asp
            100                 105                 110

Tyr Trp Gly Gln Gly Thr Gln Val Thr Val Ser Ser His His His His
        115                 120                 125

His His Glu Pro Glu Ala
    130


<210> SEQ ID NO 4
<211> LENGTH: 127
<212> TYPE: PRT
<213> ORGANISM: Artificial Sequence
<220> FEATURE:
<223> OTHER INFORMATION: MP1521_G9 Nanobody (CA15884)

<400> SEQUENCE: 4

Gln Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Tyr
            20                  25                  30

Arg Met Gly Trp Phe Arg Gln Ala Pro Gly Lys Glu Arg Glu Phe Val
        35                  40                  45
```

```
Ala Gly Trp Asn Ser Ile Asn Ile Tyr Tyr Ala Asp Ser Val Lys Gly
    50                  55                  60

Arg Phe Thr Ile Ser Gly Asp Asn Ala Lys Ser Thr Val Tyr Leu Gln
65                  70                  75                  80

Met Asn Ser Leu Lys Pro Glu Asp Thr Ala Val Tyr Tyr Cys Ala Ala
                85                  90                  95

Arg Gly Leu Gly Gln Thr Glu Tyr Asn Tyr Trp Gly Gln Gly Thr Gln
            100                 105                 110

Val Thr Val Ser Ser His His His His His His Glu Pro Glu Ala
        115                 120                 125
```

<210> SEQ ID NO 5
<211> LENGTH: 129
<212> TYPE: PRT
<213> ORGANISM: Artificial Sequence
<220> FEATURE:
<223> OTHER INFORMATION: MP1522_A12 Nanobody (CA15885)

<400> SEQUENCE: 5

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asn Met Ala Trp Phe Arg Gln Val Pro Gly Lys Glu Arg Glu Phe Val
        35                  40                  45

Ala Ser Ile Ala Arg Thr Gly Ser Gly Thr Tyr Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Gln Asp Thr Ala Val Tyr Tyr Cys
                85                  90                  95

Thr Ala Gly Gly Ser Leu Ala Thr Ile Ser Asp Tyr Trp Gly Gln Gly
            100                 105                 110

Thr Gln Val Thr Val Ser Ser His His His His His His Glu Pro Glu
        115                 120                 125

Ala
```

<210> SEQ ID NO 6
<211> LENGTH: 134
<212> TYPE: PRT
<213> ORGANISM: Artificial Sequence
<220> FEATURE:
<223> OTHER INFORMATION: MP1522_B7 Nanobody (CA15886)

<400> SEQUENCE: 6

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Gly Met Gly Trp Phe Arg Gln Ala Pro Gly Lys Glu Arg Glu Phe Ala
        35                  40                  45

Ala Gly Ile Thr Gly Thr Ala Gly Ile Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95
```

```
Ala Ala Gly Leu Thr Ser Tyr Ala Gly Arg Gly Ala Ala Gly Tyr Asp
            100                 105                 110

Tyr Trp Gly Gln Gly Thr Gln Val Thr Val Ser Ser His His His His
        115                 120                 125

His His Glu Pro Glu Ala
    130


<210> SEQ ID NO 7
<211> LENGTH: 136
<212> TYPE: PRT
<213> ORGANISM: Artificial Sequence
<220> FEATURE:
<223> OTHER INFORMATION: MP1522_E8 Nanobody (CA15887)

<400> SEQUENCE: 7

Gln Val Gln Leu Val Glu Ser Gly Gly Gly Leu Val Gln Ala Gly Gly
1               5                   10                  15

Ser Leu Arg Leu Ser Cys Ala Ala Pro Glu Arg Thr Phe Ser Ser His
            20                  25                  30

His Met Ala Trp Phe Arg Gln Ala Pro Gly Met Glu Arg Glu Phe Val
        35                  40                  45

Ala Gly Ile Ser Trp Ser Phe Gly Thr Thr Ser Tyr Ala Asp Ser Val
    50                  55                  60

Lys Gly Arg Phe Thr Ile Ser Arg Asp Asn Ala Lys Gly Thr Val Tyr
65                  70                  75                  80

Leu Gln Met Asn Ser Leu Lys Pro Glu Asp Thr Ala Val Tyr Tyr Cys
                85                  90                  95

Ala Ala Met Pro Thr Tyr Arg Gly Arg Lys Tyr Tyr Leu Ala Asp Asp
            100                 105                 110

Tyr Asn Tyr Trp Gly Gln Gly Thr Gln Val Thr Val Ser Ser His His
        115                 120                 125

His His His His Glu Pro Glu Ala
    130                 135


<210> SEQ ID NO 8
<211> LENGTH: 132
<212> TYPE: PRT
<213> ORGANISM: Artificial Sequence
<220> FEATURE:
<223> OTHER INFORMATION: MP1522_B9 Nanobody (CA15888)

<400> SEQUENCE: 8

Gln Val Gln Leu Val Glu Ser Gly Gly Gly Leu Val Gln Ala Gly Gly
1               5                   10                  15

Ser Leu Arg Leu Ser Cys Val Arg Ser Ala Arg Thr Phe Gly Ser Val
            20                  25                  30

Ala Met Gly Trp Phe Arg Gln Ala Pro Gly Lys Glu Arg Glu Phe Val
        35                  40                  45

Thr Ala Ile Asp Trp Ser Gly Ser Asn Thr Leu Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Ser Arg Arg Val Val Val Thr Thr Ser Asp Phe Asp Ser Trp
            100                 105                 110

Gly Gln Gly Thr Gln Val Thr Val Ser Ser His His His His His His
```

```
        115                 120                 125

Glu Pro Glu Ala
    130


<210> SEQ ID NO 9
<211> LENGTH: 127
<212> TYPE: PRT
<213> ORGANISM: Artificial Sequence
<220> FEATURE:
<223> OTHER INFORMATION: MP1521_E4 Nanobody (CA15889)

<400> SEQUENCE: 9

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Thr
            20                  25                  30

Phe Met Gly Trp Phe Arg Gln Ala Pro Gly Lys Glu Arg Asp Phe Val
        35                  40                  45

Ala Ser Ile Thr Trp Asn Arg Gly Leu Thr Thr Tyr Ala Asp Ser Val
    50                  55                  60

Lys Gly Arg Phe Thr Ile Ser Arg Asp Ser Ala Lys Asn Thr Val Asp
65                  70                  75                  80

Leu Gln Met Asn Asn Leu Lys Pro Glu Asp Thr Ala Val Tyr Tyr Cys
                85                  90                  95

Val Leu Gly Met Gly Thr Ser Phe Ala Ser Trp Gly Gln Gly Thr Gln
            100                 105                 110

Val Thr Val Ser Ser His His His His His His Glu Pro Glu Ala
        115                 120                 125


<210> SEQ ID NO 10
<211> LENGTH: 130
<212> TYPE: PRT
<213> ORGANISM: Artificial Sequence
<220> FEATURE:
<223> OTHER INFORMATION: MP1521_H5 Nanobody (CA15890)

<400> SEQUENCE: 10

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ser Met Ser Trp Val Arg Gln Ala Pro Gly Lys Gly Leu Glu Trp Val
        35                  40                  45

Ser Arg Ile Leu Thr Asp Gly Gly Thr Thr Ser Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Ala Arg Gly Trp Pro Ser Asp Gly Tyr Ser Gly Gly Tyr Arg Gly Gln
            100                 105                 110

Gly Thr Gln Val Thr Val Ser Ser His His His His His His Glu Pro
        115                 120                 125

Glu Ala
    130


<210> SEQ ID NO 11
<211> LENGTH: 135
```

<212> TYPE: PRT
<213> ORGANISM: Artificial Sequence
<220> FEATURE:
<223> OTHER INFORMATION: MP1522_C10 Nanobody (CA15891)

<400> SEQUENCE: 11

```
Gln Val Gln Leu Val Glu Ser Gly Gly Gly Leu Val Gln Ala Gly Gly
1               5                   10                  15

Ser Leu Arg Leu Ala Cys Ala Ala Ser Gly Arg Thr Ser Gly Ser Tyr
            20                  25                  30

Ala Ile Gly Trp Phe Arg Gln Ala Pro Gly Lys Glu Arg Glu Phe Ala
        35                  40                  45

Ala Ala Ile Ser Phe Thr Ala Gly Val Thr Tyr Tyr Ser Asn Ser Val
    50                  55                  60

Lys Gly Arg Phe Thr Ile Ser Arg Asp Ser Ala Lys Asn Thr Ala Tyr
65                  70                  75                  80

Leu Gln Met Asn Thr Leu Lys Pro Glu Asp Thr Ala Val Tyr Tyr Cys
                85                  90                  95

Ala Thr Leu Pro Ser Leu Val Leu Ile Leu Thr Ala Lys Pro Asn Ile
            100                 105                 110

Gly Tyr Trp Gly Gln Gly Thr Gln Val Thr Val Ser Ser His His His
        115                 120                 125

His His His Glu Pro Glu Ala
    130                 135
```

<210> SEQ ID NO 12
<211> LENGTH: 132
<212> TYPE: PRT
<213> ORGANISM: Artificial Sequence
<220> FEATURE:
<223> OTHER INFORMATION: MP1522_A5 Nanobody (CA15892)

<400> SEQUENCE: 12

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Ser
            20                  25                  30

Tyr Met Ser Trp Val Arg Gln Ala Pro Gly Lys Gly Pro Glu Trp Val
        35                  40                  45

Ser Ser Ile Ser Pro Ser Ala Trp Ile Ile Thr His Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn His Leu Lys Pro Glu Asp Ala Ala Leu Tyr Tyr Cys
                85                  90                  95

Ala Arg Arg Gln Gly Tyr Asp Gly Tyr Val Pro Ser Arg Asp Tyr Trp
            100                 105                 110

Gly Gln Gly Thr Gln Val Thr Val Ser Ser His His His His His His
        115                 120                 125

Glu Pro Glu Ala
    130
```

<210> SEQ ID NO 13
<211> LENGTH: 127
<212> TYPE: PRT
<213> ORGANISM: Artificial Sequence
<220> FEATURE:
<223> OTHER INFORMATION: MP1521_B4 Nanobody (CA15893)

<400> SEQUENCE: 13

```
Gln Val Gln Leu Val Glu Ser Gly Gly Gly Leu Val Gln Pro Gly Gly
1               5                   10                  15

Ser Leu Arg Leu Ser Cys Ala Ala Ser Lys Ser Phe Phe Asn Ile Tyr
            20                  25                  30

Asp Leu Ala Trp Tyr Arg Gln Ala Pro Gly Lys Gln Arg Glu Leu Val
        35                  40                  45

Ala Ser Ile Thr Lys Val Gly Ser Thr Asn Tyr Ala Asp Ser Val Lys
    50                  55                  60

Gly Arg Phe Thr Thr Ser Arg Asp Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Leu Val Ser Pro Gly Gly Val Tyr Asn Tyr Trp Gly Gln Gly Thr Gln
            100                 105                 110

Val Thr Val Ser Ser His His His His His His Glu Pro Glu Ala
        115                 120                 125
```

<210> SEQ ID NO 14
<211> LENGTH: 125
<212> TYPE: PRT
<213> ORGANISM: Artificial Sequence
<220> FEATURE:
<223> OTHER INFORMATION: MP1521_F3 Nanobody (CA15894)

<400> SEQUENCE: 14

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Gly Phe Gly Pro Asn
            20                  25                  30

Val Met Gly Trp Tyr Arg Gln Ala Pro Gly Lys Arg Arg Glu Leu Val
        35                  40                  45

Ala Thr Ile Asn Arg Ile Gly Asn Ile Asn Tyr Gly Asp Ser Val Lys
    50                  55                  60

Gly Arg Phe Thr Leu Ser Arg Glu Ile Ala Val Asn Thr Val Tyr Leu
65                  70                  75                  80

Gln Met Asn Ser Leu Lys Pro Glu Asp Ala Ala Asn Tyr Tyr Cys Tyr
                85                  90                  95

Ala Ala Lys Tyr Gly Val Asp Tyr Trp Gly Lys Gly Thr Gln Val Thr
            100                 105                 110

Val Ser Ser His His His His His His Glu Pro Glu Ala
        115                 120                 125
```

<210> SEQ ID NO 15
<211> LENGTH: 121
<212> TYPE: PRT
<213> ORGANISM: Artificial Sequence
<220> FEATURE:
<223> OTHER INFORMATION: MP1521_B1 Nanobody (CA15895)

<400> SEQUENCE: 15

```
Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ser
            20                  25                  30

Tyr Met Asp Trp Val Arg Gln Ala Pro Gly Lys Gly Ile Glu Trp Val
        35                  40                  45
```

-continued

```
Ser Thr Ile Ser Pro Gly Gly Arg Ile Thr Tyr Ala Val Ser Val Glu
    50                  55                  60

Gly Arg Phe Thr Leu Ser Arg Asp Asn Ala Lys Asn Thr Leu Ser Leu
65                  70                  75                  80

Gln Met Asn Glu Leu Lys Pro Glu Asp Thr Ala Val Tyr Tyr Cys Arg
                85                  90                  95

Arg Leu Gly Glu Lys Gly Gln Gly Thr Gln Val Thr Val Ser Ser His
            100                 105                 110

His His His His His Glu Pro Glu Ala
        115                 120


<210> SEQ ID NO 16
<211> LENGTH: 125
<212> TYPE: PRT
<213> ORGANISM: Artificial Sequence
<220> FEATURE:
<223> OTHER INFORMATION: MP1521_E1 Nanobody (CA15896)

<400> SEQUENCE: 16

Gln Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Thr Arg Ser Pro
            20                  25                  30

Thr Met Ser Trp Ala Arg Gln Ala Pro Gly Arg Gln Arg Glu Trp Val
        35                  40                  45

Thr Ser Ile Leu Gly Thr Gly Arg Thr Asp Tyr Ala Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Asn Leu Lys Pro Glu Asp Ser Ala Val Tyr Tyr Cys Tyr
                85                  90                  95

Thr Val Leu Asn Gly Arg Pro Ser Trp Gly Gln Gly Thr Gln Val Thr
            100                 105                 110

Val Ser Ser His His His His His His Glu Pro Glu Ala
        115                 120                 125


<210> SEQ ID NO 17
<211> LENGTH: 13
<212> TYPE: PRT
<213> ORGANISM: Artificial Sequence
<220> FEATURE:
<223> OTHER INFORMATION: conserved  beta-strand A of a Nanobody

<400> SEQUENCE: 17

Gln Val Gln Leu Val Glu Ser Gly Gly Gly Leu Val Gln
1               5                   10


<210> SEQ ID NO 18
<211> LENGTH: 389
<212> TYPE: PRT
<213> ORGANISM: Artificial Sequence
<220> FEATURE:
<223> OTHER INFORMATION: circularly permutated c7HopQ variant of
      Helicobacter pylori strain G27 HopQ adhesin domain protein

<400> SEQUENCE: 18

Thr Lys Thr Thr Thr Ser Val Ile Asp Thr Thr Asn Asp Ala Gln Asn
1               5                   10                  15

Leu Leu Thr Gln Ala Gln Thr Ile Val Asn Thr Leu Lys Asp Tyr Cys
            20                  25                  30
```

-continued

```
Pro Ile Leu Ile Ala Lys Ser Ser Ser Ser Asn Gly Gly Thr Asn Asn
        35                  40                  45

Ala Asn Thr Pro Ser Trp Gln Thr Ala Gly Gly Gly Lys Asn Ser Cys
    50                  55                  60

Ala Thr Phe Gly Ala Glu Phe Ser Ala Ala Ser Asp Met Ile Asn Asn
65                  70                  75                  80

Ala Gln Lys Ile Val Gln Glu Thr Gln Gln Leu Ser Ala Asn Gln Pro
                85                  90                  95

Lys Asn Ile Thr Gln Pro His Asn Leu Asn Leu Asn Ser Pro Ser Ser
            100                 105                 110

Leu Thr Ala Leu Ala Gln Lys Met Leu Lys Asn Ala Gln Ser Gln Ala
        115                 120                 125

Glu Ile Leu Lys Leu Ala Asn Gln Val Glu Ser Asp Phe Asn Lys Leu
    130                 135                 140

Ser Ser Gly His Leu Lys Asp Tyr Ile Gly Lys Cys Asp Ala Ser Ala
145                 150                 155                 160

Ile Ser Ser Ala Asn Met Thr Met Gln Asn Gln Lys Asn Asn Trp Gly
                165                 170                 175

Asn Gly Cys Ala Gly Val Glu Glu Thr Gln Ser Leu Leu Lys Thr Ser
            180                 185                 190

Ala Ala Asp Phe Asn Asn Gln Thr Pro Gln Ile Asn Gln Ala Gln Asn
        195                 200                 205

Leu Ala Asn Thr Leu Ile Gln Glu Leu Gly Asn Asn Thr Tyr Glu Gln
    210                 215                 220

Leu Ser Arg Leu Leu Thr Asn Asp Asn Gly Thr Asn Ser Lys Thr Ser
225                 230                 235                 240

Ala Gln Ala Ile Asn Gln Ala Val Asn Asn Leu Asn Glu Arg Ala Lys
                245                 250                 255

Thr Leu Ala Gly Gly Thr Thr Asn Ser Pro Ala Tyr Gln Ala Thr Leu
            260                 265                 270

Leu Ala Leu Arg Ser Val Leu Gly Leu Trp Asn Ser Met Gly Tyr Ala
        275                 280                 285

Val Ile Cys Gly Gly Tyr Thr Lys Ser Pro Gly Glu Asn Asn Gln Lys
    290                 295                 300

Asp Phe His Tyr Thr Asp Glu Asn Gly Asn Gly Thr Thr Ile Asn Cys
305                 310                 315                 320

Gly Gly Ser Thr Asn Ser Asn Gly Thr His Ser Tyr Asn Gly Thr Asn
                325                 330                 335

Thr Leu Lys Ala Asp Lys Asn Val Ser Leu Ser Ile Glu Gln Tyr Glu
            340                 345                 350

Lys Ile His Glu Ala Tyr Gln Ile Leu Ser Lys Ala Leu Lys Gln Ala
        355                 360                 365

Gly Leu Ala Pro Leu Asn Ser Lys Gly Glu Lys Leu Glu Ala His Val
    370                 375                 380

Thr Thr Ser Lys Tyr
385
```

<210> SEQ ID NO 19
<211> LENGTH: 7
<212> TYPE: PRT
<213> ORGANISM: Artificial Sequence
<220> FEATURE:
<223> OTHER INFORMATION: conserved beta -strand B of a Nanobody

<400> SEQUENCE: 19

-continued

```
Gly Ser Leu Arg Leu Ser Cys
1               5


<210> SEQ ID NO 20
<211> LENGTH: 521
<212> TYPE: PRT
<213> ORGANISM: Artificial Sequence
<220> FEATURE:
<223> OTHER INFORMATION: MbNb1_B9c7HopQ MegaBody (CA15898)

<400> SEQUENCE: 20

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350
```

```
Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Leu
                405                 410                 415

Cys Ser Ile Pro Met Gly Trp Phe Arg Gln Ala Pro Gly Lys Glu Arg
            420                 425                 430

Glu Phe Val Ala Ala Ile Arg Trp Ser Gly Gly Ser Thr Tyr Tyr Ala
        435                 440                 445

Asp Ser Val Lys Gly Arg Phe Ser Ile Ser Lys Asp Asn Ala Lys Asn
    450                 455                 460

Thr Val Tyr Leu Gln Met Asn Asn Leu Lys Pro Glu Asp Thr Ala Thr
465                 470                 475                 480

Tyr Tyr Cys Ala Ser Ala Ala Pro Tyr Ser Ser Trp Ser Arg Gly Leu
                485                 490                 495

Glu Tyr Asp Tyr Trp Gly Gln Gly Thr Gln Val Thr Val Ser Ser His
            500                 505                 510

His His His His His Glu Pro Glu Ala
        515                 520


<210> SEQ ID NO 21
<211> LENGTH: 514
<212> TYPE: PRT
<213> ORGANISM: Artificial Sequence
<220> FEATURE:
<223> OTHER INFORMATION: MbNbG9c7HopQ MegaBody (CA15899)

<400> SEQUENCE: 21

Gln Val Gln Leu Val Glu Ser Gly Gly Gly Ser Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190
```

```
Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Phe
                405                 410                 415

Ser Thr Tyr Arg Met Gly Trp Phe Arg Gln Ala Pro Gly Lys Glu Arg
            420                 425                 430

Glu Phe Val Ala Gly Trp Asn Ser Ile Asn Ile Tyr Tyr Ala Asp Ser
        435                 440                 445

Val Lys Gly Arg Phe Thr Ile Ser Gly Asp Asn Ala Lys Ser Thr Val
    450                 455                 460

Tyr Leu Gln Met Asn Ser Leu Lys Pro Glu Asp Thr Ala Val Tyr Tyr
465                 470                 475                 480

Cys Ala Ala Arg Gly Leu Gly Gln Thr Glu Tyr Asn Tyr Trp Gly Gln
                485                 490                 495

Gly Thr Gln Val Thr Val Ser Ser His His His His His His Glu Pro
            500                 505                 510

Glu Ala
```

<210> SEQ ID NO 22
<211> LENGTH: 516
<212> TYPE: PRT
<213> ORGANISM: Artificial Sequence
<220> FEATURE:
<223> OTHER INFORMATION: MbNbA12c7HopQ MegaBody (CA15900)

<400> SEQUENCE: 22

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
```

-continued

```
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Phe
                405                 410                 415

Ser Ser Tyr Asn Met Ala Trp Phe Arg Gln Val Pro Gly Lys Glu Arg
            420                 425                 430

Glu Phe Val Ala Ser Ile Ala Arg Thr Gly Ser Gly Thr Tyr Tyr Arg
        435                 440                 445

Asp Ser Val Lys Gly Arg Phe Thr Ile Ser Arg Asp Asn Ala Lys Asn
    450                 455                 460
```

Thr Val Tyr Leu Gln Met Asn Ser Leu Lys Pro Gln Asp Thr Ala Val
465 470 475 480

Tyr Tyr Cys Thr Ala Gly Gly Ser Leu Ala Thr Ile Ser Asp Tyr Trp
485 490 495

Gly Gln Gly Thr Gln Val Thr Val Ser Ser His His His His His His
500 505 510

Glu Pro Glu Ala
515

<210> SEQ ID NO 23
<211> LENGTH: 521
<212> TYPE: PRT
<213> ORGANISM: Artificial Sequence
<220> FEATURE:
<223> OTHER INFORMATION: MbNbB7c7HopQ MegaBody (CA15901)

<400> SEQUENCE: 23

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

Thr Leu Ile Gln Glu Leu Gly Asn Asn Thr Tyr Glu Gln Leu Ser Arg
225 230 235 240

Leu Leu Thr Asn Asp Asn Gly Thr Asn Ser Lys Thr Ser Ala Gln Ala
245 250 255

Ile Asn Gln Ala Val Asn Asn Leu Asn Glu Arg Ala Lys Thr Leu Ala
260 265 270

Gly Gly Thr Thr Asn Ser Pro Ala Tyr Gln Ala Thr Leu Leu Ala Leu
275 280 285

Arg Ser Val Leu Gly Leu Trp Asn Ser Met Gly Tyr Ala Val Ile Cys
290 295 300

```
Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Ser Phe
                405                 410                 415

Ser Ser Tyr Gly Met Gly Trp Phe Arg Gln Ala Pro Gly Lys Glu Arg
            420                 425                 430

Glu Phe Ala Ala Gly Ile Thr Gly Thr Ala Gly Ile Thr Tyr Tyr Thr
        435                 440                 445

Asp Ser Val Lys Gly Arg Phe Thr Ile Ser Arg Asp Asn Ala Lys Asn
    450                 455                 460

Thr Val Tyr Leu Gln Met Asn Asn Leu Lys Pro Glu Asp Thr Ala Val
465                 470                 475                 480

Tyr Tyr Cys Ala Ala Gly Leu Thr Ser Tyr Ala Gly Arg Gly Ala Ala
                485                 490                 495

Gly Tyr Asp Tyr Trp Gly Gln Gly Thr Gln Val Thr Val Ser Ser His
            500                 505                 510

His His His His His Glu Pro Glu Ala
        515                 520
```

<210> SEQ ID NO 24
<211> LENGTH: 523
<212> TYPE: PRT
<213> ORGANISM: Artificial Sequence
<220> FEATURE:
<223> OTHER INFORMATION: MbNbE8c7HopQ MegaBody (CA15902)

<400> SEQUENCE: 24

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140
```

-continued

```
Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Pro Glu Arg Thr Phe
                405                 410                 415

Ser Ser His His Met Ala Trp Phe Arg Gln Ala Pro Gly Met Glu Arg
            420                 425                 430

Glu Phe Val Ala Gly Ile Ser Trp Ser Phe Gly Thr Thr Ser Tyr Ala
        435                 440                 445

Asp Ser Val Lys Gly Arg Phe Thr Ile Ser Arg Asp Asn Ala Lys Gly
    450                 455                 460

Thr Val Tyr Leu Gln Met Asn Ser Leu Lys Pro Glu Asp Thr Ala Val
465                 470                 475                 480

Tyr Tyr Cys Ala Ala Met Pro Thr Tyr Arg Gly Arg Lys Tyr Tyr Leu
                485                 490                 495

Ala Asp Asp Tyr Asn Tyr Trp Gly Gln Gly Thr Gln Val Thr Val Ser
            500                 505                 510

Ser His His His His His His Glu Pro Glu Ala
        515                 520
```

<210> SEQ ID NO 25
<211> LENGTH: 519
<212> TYPE: PRT
<213> ORGANISM: Artificial Sequence
<220> FEATURE:

-continued

<223> OTHER INFORMATION: MbNb2_B9c7HopQ MegaBody (CA15903)

<400> SEQUENCE: 25

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

-continued

```
Lys Tyr Gly Ser Leu Arg Leu Ser Cys Val Arg Ser Ala Arg Thr Phe
                405                 410                 415

Gly Ser Val Ala Met Gly Trp Phe Arg Gln Ala Pro Gly Lys Glu Arg
            420                 425                 430

Glu Phe Val Thr Ala Ile Asp Trp Ser Gly Ser Asn Thr Leu Tyr Ala
        435                 440                 445

Asp Ser Val Lys Gly Arg Phe Thr Ile Ser Arg Asp Asn Ala Lys Asn
    450                 455                 460

Thr Val Tyr Leu Gln Met Asn Ser Leu Lys Pro Asp Asp Thr Ala Val
465                 470                 475                 480

Tyr Tyr Cys Ala Ala Ser Arg Arg Val Val Val Thr Thr Ser Asp Phe
                485                 490                 495

Asp Ser Trp Gly Gln Gly Thr Gln Val Thr Val Ser Ser His His His
            500                 505                 510

His His His Glu Pro Glu Ala
        515


<210> SEQ ID NO 26
<211> LENGTH: 514
<212> TYPE: PRT
<213> ORGANISM: Artificial Sequence
<220> FEATURE:
<223> OTHER INFORMATION: MbNbE4c7HopQ MegaBody (CA15191)

<400> SEQUENCE: 26

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240
```

-continued

```
Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Phe
                405                 410                 415

Gly Ser Thr Phe Met Gly Trp Phe Arg Gln Ala Pro Gly Lys Glu Arg
            420                 425                 430

Asp Phe Val Ala Ser Ile Thr Trp Asn Arg Gly Leu Thr Thr Tyr Ala
        435                 440                 445

Asp Ser Val Lys Gly Arg Phe Thr Ile Ser Arg Asp Ser Ala Lys Asn
    450                 455                 460

Thr Val Asp Leu Gln Met Asn Asn Leu Lys Pro Glu Asp Thr Ala Val
465                 470                 475                 480

Tyr Tyr Cys Val Leu Gly Met Gly Thr Ser Phe Ala Ser Trp Gly Gln
                485                 490                 495

Gly Thr Gln Val Thr Val Ser Ser His His His His His His Glu Pro
            500                 505                 510

Glu Ala


<210> SEQ ID NO 27
<211> LENGTH: 517
<212> TYPE: PRT
<213> ORGANISM: Artificial Sequence
<220> FEATURE:
<223> OTHER INFORMATION: MbNbH5c7HopQ MegaBody (CA15904)

<400> SEQUENCE: 27

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
```

-continued

```
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Phe Thr Phe
                405                 410                 415

Ser Thr Tyr Ser Met Ser Trp Val Arg Gln Ala Pro Gly Lys Gly Leu
            420                 425                 430

Glu Trp Val Ser Arg Ile Leu Thr Asp Gly Gly Thr Thr Ser Tyr Pro
        435                 440                 445

Asp Ser Val Lys Gly Arg Phe Thr Ile Ser Arg Asp Asn Ala Lys Asn
    450                 455                 460

Thr Leu Tyr Leu Gln Met Asn Asn Leu Lys Pro Glu Asp Thr Ala Val
465                 470                 475                 480

Tyr Tyr Cys Ala Arg Gly Trp Pro Ser Asp Gly Tyr Ser Gly Gly Tyr
                485                 490                 495

Arg Gly Gln Gly Thr Gln Val Thr Val Ser Ser His His His His His
            500                 505                 510
```

```
His Glu Pro Glu Ala
        515


<210> SEQ ID NO 28
<211> LENGTH: 522
<212> TYPE: PRT
<213> ORGANISM: Artificial Sequence
<220> FEATURE:
<223> OTHER INFORMATION: MbNbC10c7HopQ MegaBody (CA15905)

<400> SEQUENCE: 28

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350
```

-continued

Ala Asp Lys Asn Val Ser Leu Ser Ile Glu Gln Tyr Glu Lys Ile His
355 360 365

Glu Ala Tyr Gln Ile Leu Ser Lys Ala Leu Lys Gln Ala Gly Leu Ala
370 375 380

Pro Leu Asn Ser Lys Gly Glu Lys Leu Glu Ala His Val Thr Thr Ser
385 390 395 400

Lys Tyr Gly Ser Leu Arg Leu Ser Cys Ala Ala Ser Gly Arg Thr Ser
405 410 415

Gly Ser Tyr Ala Ile Gly Trp Phe Arg Gln Ala Pro Gly Lys Glu Arg
420 425 430

Glu Phe Ala Ala Ala Ile Ser Phe Thr Ala Gly Val Thr Tyr Tyr Ser
435 440 445

Asn Ser Val Lys Gly Arg Phe Thr Ile Ser Arg Asp Ser Ala Lys Asn
450 455 460

Thr Ala Tyr Leu Gln Met Asn Thr Leu Lys Pro Glu Asp Thr Ala Val
465 470 475 480

Tyr Tyr Cys Ala Thr Leu Pro Ser Leu Val Leu Ile Leu Thr Ala Lys
485 490 495

Pro Asn Ile Gly Tyr Trp Gly Gln Gly Thr Gln Val Thr Val Ser Ser
500 505 510

His His His His His His Glu Pro Glu Ala
515 520

<210> SEQ ID NO 29
<211> LENGTH: 519
<212> TYPE: PRT
<213> ORGANISM: Artificial Sequence
<220> FEATURE:
<223> OTHER INFORMATION: MbNbA5c7HopQ MegaBody (CA15906)

<400> SEQUENCE: 29

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

-continued

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

Thr Leu Ile Gln Glu Leu Gly Asn Asn Thr Tyr Glu Gln Leu Ser Arg
225 230 235 240

Leu Leu Thr Asn Asp Asn Gly Thr Asn Ser Lys Thr Ser Ala Gln Ala
245 250 255

Ile Asn Gln Ala Val Asn Asn Leu Asn Glu Arg Ala Lys Thr Leu Ala
260 265 270

Gly Gly Thr Thr Asn Ser Pro Ala Tyr Gln Ala Thr Leu Leu Ala Leu
275 280 285

Arg Ser Val Leu Gly Leu Trp Asn Ser Met Gly Tyr Ala Val Ile Cys
290 295 300

Gly Gly Tyr Thr Lys Ser Pro Gly Glu Asn Asn Gln Lys Asp Phe His
305 310 315 320

Tyr Thr Asp Glu Asn Gly Asn Gly Thr Thr Ile Asn Cys Gly Gly Ser
325 330 335

Thr Asn Ser Asn Gly Thr His Ser Tyr Asn Gly Thr Asn Thr Leu Lys
340 345 350

Ala Asp Lys Asn Val Ser Leu Ser Ile Glu Gln Tyr Glu Lys Ile His
355 360 365

Glu Ala Tyr Gln Ile Leu Ser Lys Ala Leu Lys Gln Ala Gly Leu Ala
370 375 380

Pro Leu Asn Ser Lys Gly Glu Lys Leu Glu Ala His Val Thr Thr Ser
385 390 395 400

Lys Tyr Gly Ser Leu Arg Leu Ser Cys Ala Ala Ser Gly Phe Ala Phe
405 410 415

Ser Asn Ser Tyr Met Ser Trp Val Arg Gln Ala Pro Gly Lys Gly Pro
420 425 430

Glu Trp Val Ser Ser Ile Ser Pro Ser Ala Trp Ile Ile Thr His Gly
435 440 445

Asp Ser Val Lys Gly Arg Phe Thr Ile Ser Arg Asp Asn Ala Lys Asn
450 455 460

Thr Leu Tyr Leu Gln Met Asn His Leu Lys Pro Glu Asp Ala Ala Leu
465 470 475 480

Tyr Tyr Cys Ala Arg Arg Gln Gly Tyr Asp Gly Tyr Val Pro Ser Arg
485 490 495

Asp Tyr Trp Gly Gln Gly Thr Gln Val Thr Val Ser Ser His His His
500 505 510

His His His Glu Pro Glu Ala
515

<210> SEQ ID NO 30
<211> LENGTH: 514
<212> TYPE: PRT
<213> ORGANISM: Artificial Sequence
<220> FEATURE:
<223> OTHER INFORMATION: MbNbB4c7HopQ MegaBody (CA15907)

<400> SEQUENCE: 30

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

-continued

```
Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Lys Ser Phe Phe
                405                 410                 415

Asn Ile Tyr Asp Leu Ala Trp Tyr Arg Gln Ala Pro Gly Lys Gln Arg
            420                 425                 430

Glu Leu Val Ala Ser Ile Thr Lys Val Gly Ser Thr Asn Tyr Ala Asp
        435                 440                 445
```

-continued

Ser Val Lys Gly Arg Phe Thr Thr Ser Arg Asp Asn Ala Lys Lys Thr
450 455 460

Val Tyr Leu Gln Met Asn Ser Leu Lys Pro Glu Asp Thr Ala Val Tyr
465 470 475 480

Tyr Cys Asn Leu Val Ser Pro Gly Gly Val Tyr Asn Tyr Trp Gly Gln
485 490 495

Gly Thr Gln Val Thr Val Ser Ser His His His His His His Glu Pro
500 505 510

Glu Ala

<210> SEQ ID NO 31
<211> LENGTH: 512
<212> TYPE: PRT
<213> ORGANISM: Artificial Sequence
<220> FEATURE:
<223> OTHER INFORMATION: MbNbF3c7HopQ MegaBody (CA15192)

<400> SEQUENCE: 31

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

Thr Leu Ile Gln Glu Leu Gly Asn Asn Thr Tyr Glu Gln Leu Ser Arg
225 230 235 240

Leu Leu Thr Asn Asp Asn Gly Thr Asn Ser Lys Thr Ser Ala Gln Ala
245 250 255

Ile Asn Gln Ala Val Asn Asn Leu Asn Glu Arg Ala Lys Thr Leu Ala
260 265 270

Gly Gly Thr Thr Asn Ser Pro Ala Tyr Gln Ala Thr Leu Leu Ala Leu
275 280 285

Arg Ser Val Leu Gly Leu Trp Asn Ser Met Gly Tyr Ala Val Ile Cys 290 295 300

Gly Gly Tyr Thr Lys Ser Pro Gly Glu Asn Asn Gln Lys Asp Phe His
305 310 315 320

Tyr Thr Asp Glu Asn Gly Asn Gly Thr Thr Ile Asn Cys Gly Gly Ser
325 330 335

Thr Asn Ser Asn Gly Thr His Ser Tyr Asn Gly Thr Asn Thr Leu Lys
340 345 350

Ala Asp Lys Asn Val Ser Leu Ser Ile Glu Gln Tyr Glu Lys Ile His
355 360 365

Glu Ala Tyr Gln Ile Leu Ser Lys Ala Leu Lys Gln Ala Gly Leu Ala
370 375 380

Pro Leu Asn Ser Lys Gly Glu Lys Leu Glu Ala His Val Thr Thr Ser
385 390 395 400

Lys Tyr Gly Ser Leu Arg Leu Ser Cys Ala Ala Ser Gly Ser Gly Phe
405 410 415

Gly Pro Asn Val Met Gly Trp Tyr Arg Gln Ala Pro Gly Lys Arg Arg
420 425 430

Glu Leu Val Ala Thr Ile Asn Arg Ile Gly Asn Ile Asn Tyr Gly Asp
435 440 445

Ser Val Lys Gly Arg Phe Thr Leu Ser Arg Glu Ile Ala Val Asn Thr
450 455 460

Val Tyr Leu Gln Met Asn Ser Leu Lys Pro Glu Asp Ala Ala Asn Tyr
465 470 475 480

Tyr Cys Tyr Ala Ala Lys Tyr Gly Val Asp Tyr Trp Gly Lys Gly Thr
485 490 495

Gln Val Thr Val Ser Ser His His His His His His Glu Pro Glu Ala
500 505 510

<210> SEQ ID NO 32
<211> LENGTH: 508
<212> TYPE: PRT
<213> ORGANISM: Artificial Sequence
<220> FEATURE:
<223> OTHER INFORMATION: MbNbB1c7HopQ MegaBody (CA15908)

<400> SEQUENCE: 32

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly

-continued

```
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Thr Ala Ser Gly Phe Ser Leu
                405                 410                 415

Ser Ser Ser Tyr Met Asp Trp Val Arg Gln Ala Pro Gly Lys Gly Ile
            420                 425                 430

Glu Trp Val Ser Thr Ile Ser Pro Gly Gly Arg Ile Thr Tyr Ala Val
        435                 440                 445

Ser Val Glu Gly Arg Phe Thr Leu Ser Arg Asp Asn Ala Lys Asn Thr
    450                 455                 460

Leu Ser Leu Gln Met Asn Glu Leu Lys Pro Glu Asp Thr Ala Val Tyr
465                 470                 475                 480

Tyr Cys Arg Arg Leu Gly Glu Lys Gly Gln Gly Thr Gln Val Thr Val
                485                 490                 495

Ser Ser His His His His His His Glu Pro Glu Ala
            500                 505
```

<210> SEQ ID NO 33
<211> LENGTH: 512
<212> TYPE: PRT
<213> ORGANISM: Artificial Sequence
<220> FEATURE:
<223> OTHER INFORMATION: MbNbE1c7HopQ MegaBody (CA15909)

<400> SEQUENCE: 33

```
Gln Val Gln Leu Val Glu Ser Gly Gly Gly Leu Val Gln Thr Lys Thr
```

-continued

```
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Thr Ile Thr
                405                 410                 415

Arg Ser Pro Thr Met Ser Trp Ala Arg Gln Ala Pro Gly Arg Gln Arg
            420                 425                 430
```

```
Glu Trp Val Thr Ser Ile Leu Gly Thr Gly Arg Thr Asp Tyr Ala Asp
        435                 440                 445

Ser Val Lys Gly Arg Phe Thr Ile Ser Arg Asp Asn Ala Asn Asn Thr
    450                 455                 460

Val Tyr Leu Gln Met Asn Asn Leu Lys Pro Glu Asp Ser Ala Val Tyr
465                 470                 475                 480

Tyr Cys Tyr Thr Val Leu Asn Gly Arg Pro Ser Trp Gly Gln Gly Thr
                485                 490                 495

Gln Val Thr Val Ser Ser His His His His His His Glu Pro Glu Ala
            500                 505                 510


<210> SEQ ID NO 34
<211> LENGTH: 522
<212> TYPE: PRT
<213> ORGANISM: Artificial Sequence
<220> FEATURE:
<223> OTHER INFORMATION: MegaBody MbNb25c7HopQ against GABAAR-beta3

<400> SEQUENCE: 34

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285
```

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly His Thr Phe
                405                 410                 415

Asn Tyr Pro Ile Met Gly Trp Phe Arg Gln Ala Pro Gly Lys Glu Arg
            420                 425                 430

Glu Phe Val Gly Ala Ile Ser Trp Ser Gly Gly Ser Thr Ser Tyr Ala
        435                 440                 445

Asp Ser Val Lys Asp Arg Phe Thr Ile Ser Arg Asp Asn Ala Lys Asn
    450                 455                 460

Thr Val Tyr Leu Glu Met Asn Asn Leu Lys Pro Glu Asp Thr Ala Val
465                 470                 475                 480

Tyr Tyr Cys Ala Ala Lys Gly Arg Tyr Ser Gly Gly Leu Tyr Tyr Pro
                485                 490                 495

Thr Asn Tyr Asp Tyr Trp Gly Gln Gly Thr Gln Val Thr Val Ser Ser
            500                 505                 510

His His His His His His Glu Pro Glu Ala
        515                 520

<210> SEQ ID NO 35
<211> LENGTH: 352
<212> TYPE: PRT
<213> ORGANISM: Artificial Sequence
<220> FEATURE:
<223> OTHER INFORMATION: human GABAAR-beta3 with C-terminal 1D4 tag

<400> SEQUENCE: 35

Gln Ser Val Asn Asp Pro Gly Asn Met Ser Phe Val Lys Glu Thr Val
1               5                   10                  15

Asp Lys Leu Leu Lys Gly Tyr Asp Ile Arg Leu Arg Pro Asp Phe Gly
            20                  25                  30

Gly Pro Pro Val Cys Val Gly Met Asn Ile Asp Ile Ala Ser Ile Asp
        35                  40                  45

Met Val Ser Glu Val Asn Met Asp Tyr Thr Leu Thr Met Tyr Phe Gln
    50                  55                  60

Gln Tyr Trp Arg Asp Lys Arg Leu Ala Tyr Ser Gly Ile Pro Leu Asn
65                  70                  75                  80

Leu Thr Leu Asp Asn Arg Val Ala Asp Gln Leu Trp Val Pro Asp Thr
                85                  90                  95

Tyr Phe Leu Asn Asp Lys Lys Ser Phe Val His Gly Val Thr Val Lys
            100                 105                 110

Asn Arg Met Ile Arg Leu His Pro Asp Gly Thr Val Leu Tyr Gly Leu
        115                 120                 125

```
Arg Ile Thr Thr Thr Ala Ala Cys Met Met Asp Leu Arg Arg Tyr Pro
    130                 135                 140

Leu Asp Glu Gln Asn Cys Thr Leu Glu Ile Glu Ser Tyr Gly Tyr Thr
145                 150                 155                 160

Thr Asp Asp Ile Glu Phe Tyr Trp Arg Gly Gly Asp Lys Ala Val Thr
                165                 170                 175

Gly Val Glu Arg Ile Glu Leu Pro Gln Phe Ser Ile Val Glu His Arg
            180                 185                 190

Leu Val Ser Arg Asn Val Val Phe Ala Thr Gly Ala Tyr Pro Arg Leu
        195                 200                 205

Ser Leu Ser Phe Arg Leu Lys Arg Asn Ile Gly Tyr Phe Ile Leu Gln
    210                 215                 220

Thr Tyr Met Pro Ser Ile Leu Ile Thr Ile Leu Ser Trp Val Ser Phe
225                 230                 235                 240

Trp Ile Asn Tyr Asp Ala Ser Ala Ala Arg Val Ala Leu Gly Ile Thr
                245                 250                 255

Thr Val Leu Thr Met Thr Thr Ile Asn Thr His Leu Arg Glu Thr Leu
            260                 265                 270

Pro Lys Ile Pro Tyr Val Thr Ala Ile Asp Met Tyr Leu Met Gly Cys
        275                 280                 285

Phe Val Phe Val Phe Leu Ala Leu Leu Glu Tyr Ala Phe Val Asn Tyr
    290                 295                 300

Ile Phe Phe Ser Gln Pro Ala Arg Ala Ala Ala Ile Asp Arg Trp Ser
305                 310                 315                 320

Arg Ile Val Phe Pro Phe Thr Phe Ser Leu Phe Asn Leu Val Tyr Trp
                325                 330                 335

Leu Tyr Tyr Val Asn Gly Ala Thr Glu Thr Ser Gln Val Ala Pro Ala
            340                 345                 350
```

<210> SEQ ID NO 36
<211> LENGTH: 135
<212> TYPE: PRT
<213> ORGANISM: Artificial Sequence
<220> FEATURE:
<223> OTHER INFORMATION: Nanobody Nb25 against GABAAR-beta3 (CA8125)

<400> SEQUENCE: 36

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly His Thr Phe Asn Tyr Pro
            20                  25                  30

Ile Met Gly Trp Phe Arg Gln Ala Pro Gly Lys Glu Arg Glu Phe Val
        35                  40                  45

Gly Ala Ile Ser Trp Ser Gly Gly Ser Thr Ser Tyr Ala Asp Ser Val
    50                  55                  60

Lys Asp Arg Phe Thr Ile Ser Arg Asp Asn Ala Lys Asn Thr Val Tyr
65                  70                  75                  80

Leu Glu Met Asn Asn Leu Lys Pro Glu Asp Thr Ala Val Tyr Tyr Cys
                85                  90                  95

Ala Ala Lys Gly Arg Tyr Ser Gly Gly Leu Tyr Tyr Pro Thr Asn Tyr
            100                 105                 110

Asp Tyr Trp Gly Gln Gly Thr Gln Val Thr Val Ser Ser His His His
        115                 120                 125

His His His Glu Pro Glu Ala
    130                 135
```

-continued

<210> SEQ ID NO 37
<211> LENGTH: 124
<212> TYPE: PRT
<213> ORGANISM: Artificial Sequence
<220> FEATURE:
<223> OTHER INFORMATION: MP1521_B9 Nanobody (CA15883)

<400> SEQUENCE: 37

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Cys Ser Ile
            20                  25                  30

Pro Met Gly Trp Phe Arg Gln Ala Pro Gly Lys Glu Arg Glu Phe Val
        35                  40                  45

Ala Ala Ile Arg Trp Ser Gly Gly Ser Thr Tyr Tyr Ala Asp Ser Val
    50                  55                  60

Lys Gly Arg Phe Ser Ile Ser Lys Asp Asn Ala Lys Asn Thr Val Tyr
65                  70                  75                  80

Leu Gln Met Asn Asn Leu Lys Pro Glu Asp Thr Ala Thr Tyr Tyr Cys
                85                  90                  95

Ala Ser Ala Ala Pro Tyr Ser Ser Trp Ser Arg Gly Leu Glu Tyr Asp
            100                 105                 110

Tyr Trp Gly Gln Gly Thr Gln Val Thr Val Ser Ser
        115                 120
```

<210> SEQ ID NO 38
<211> LENGTH: 117
<212> TYPE: PRT
<213> ORGANISM: Artificial Sequence
<220> FEATURE:
<223> OTHER INFORMATION: MP1521_G9 Nanobody (CA15884)

<400> SEQUENCE: 38

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Phe Ser Thr Tyr
            20                  25                  30

Arg Met Gly Trp Phe Arg Gln Ala Pro Gly Lys Glu Arg Glu Phe Val
        35                  40                  45

Ala Gly Trp Asn Ser Ile Asn Ile Tyr Tyr Ala Asp Ser Val Lys Gly
    50                  55                  60

Arg Phe Thr Ile Ser Gly Asp Asn Ala Lys Ser Thr Val Tyr Leu Gln
65                  70                  75                  80

Met Asn Ser Leu Lys Pro Glu Asp Thr Ala Val Tyr Tyr Cys Ala Ala
                85                  90                  95

Arg Gly Leu Gly Gln Thr Glu Tyr Asn Tyr Trp Gly Gln Gly Thr Gln
            100                 105                 110

Val Thr Val Ser Ser
        115
```

<210> SEQ ID NO 39
<211> LENGTH: 119
<212> TYPE: PRT
<213> ORGANISM: Artificial Sequence
<220> FEATURE:
<223> OTHER INFORMATION: MP1522_A12 Nanobody (CA15885)

<400> SEQUENCE: 39

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asn Met Ala Trp Phe Arg Gln Val Pro Gly Lys Glu Arg Glu Phe Val
        35                  40                  45

Ala Ser Ile Ala Arg Thr Gly Ser Gly Thr Tyr Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Gln Asp Thr Ala Val Tyr Tyr Cys
                85                  90                  95

Thr Ala Gly Gly Ser Leu Ala Thr Ile Ser Asp Tyr Trp Gly Gln Gly
            100                 105                 110

Thr Gln Val Thr Val Ser Ser
        115
```

<210> SEQ ID NO 40
<211> LENGTH: 124
<212> TYPE: PRT
<213> ORGANISM: Artificial Sequence
<220> FEATURE:
<223> OTHER INFORMATION: MP1522_B7 Nanobody (CA15886)

<400> SEQUENCE: 40

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Gly Met Gly Trp Phe Arg Gln Ala Pro Gly Lys Glu Arg Glu Phe Ala
        35                  40                  45

Ala Gly Ile Thr Gly Thr Ala Gly Ile Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Gly Leu Thr Ser Tyr Ala Gly Arg Gly Ala Ala Gly Tyr Asp
            100                 105                 110

Tyr Trp Gly Gln Gly Thr Gln Val Thr Val Ser Ser
        115                 120
```

<210> SEQ ID NO 41
<211> LENGTH: 126
<212> TYPE: PRT
<213> ORGANISM: Artificial Sequence
<220> FEATURE:
<223> OTHER INFORMATION: MP1522_E8 Nanobody (CA15887)

<400> SEQUENCE: 41

```
Gln Val Gln Leu Val Glu Ser Gly Gly Gly Leu Val Gln Ala Gly Gly
1               5                   10                  15

Ser Leu Arg Leu Ser Cys Ala Ala Pro Glu Arg Thr Phe Ser Ser His
            20                  25                  30

His Met Ala Trp Phe Arg Gln Ala Pro Gly Met Glu Arg Glu Phe Val
        35                  40                  45

Ala Gly Ile Ser Trp Ser Phe Gly Thr Thr Ser Tyr Ala Asp Ser Val
    50                  55                  60
```

-continued

```
Lys Gly Arg Phe Thr Ile Ser Arg Asp Asn Ala Lys Gly Thr Val Tyr
65                  70                  75                  80

Leu Gln Met Asn Ser Leu Lys Pro Glu Asp Thr Ala Val Tyr Tyr Cys
                85                  90                  95

Ala Ala Met Pro Thr Tyr Arg Gly Arg Lys Tyr Tyr Leu Ala Asp Asp
            100                 105                 110

Tyr Asn Tyr Trp Gly Gln Gly Thr Gln Val Thr Val Ser Ser
        115                 120                 125


<210> SEQ ID NO 42
<211> LENGTH: 122
<212> TYPE: PRT
<213> ORGANISM: Artificial Sequence
<220> FEATURE:
<223> OTHER INFORMATION: MP1522_B9 Nanobody (CA15888)

<400> SEQUENCE: 42

Gln Val Gln Leu Val Glu Ser Gly Gly Gly Leu Val Gln Ala Gly Gly
1               5                   10                  15

Ser Leu Arg Leu Ser Cys Val Arg Ser Ala Arg Thr Phe Gly Ser Val
            20                  25                  30

Ala Met Gly Trp Phe Arg Gln Ala Pro Gly Lys Glu Arg Glu Phe Val
        35                  40                  45

Thr Ala Ile Asp Trp Ser Gly Ser Asn Thr Leu Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Ser Arg Arg Val Val Val Thr Thr Ser Asp Phe Asp Ser Trp
            100                 105                 110

Gly Gln Gly Thr Gln Val Thr Val Ser Ser
        115                 120


<210> SEQ ID NO 43
<211> LENGTH: 117
<212> TYPE: PRT
<213> ORGANISM: Artificial Sequence
<220> FEATURE:
<223> OTHER INFORMATION: MP1521_E4 Nanobody (CA15889)

<400> SEQUENCE: 43

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Thr
            20                  25                  30

Phe Met Gly Trp Phe Arg Gln Ala Pro Gly Lys Glu Arg Asp Phe Val
        35                  40                  45

Ala Ser Ile Thr Trp Asn Arg Gly Leu Thr Thr Tyr Ala Asp Ser Val
    50                  55                  60

Lys Gly Arg Phe Thr Ile Ser Arg Asp Ser Ala Lys Asn Thr Val Asp
65                  70                  75                  80

Leu Gln Met Asn Asn Leu Lys Pro Glu Asp Thr Ala Val Tyr Tyr Cys
                85                  90                  95

Val Leu Gly Met Gly Thr Ser Phe Ala Ser Trp Gly Gln Gly Thr Gln
            100                 105                 110

Val Thr Val Ser Ser
```

115

<210> SEQ ID NO 44
<211> LENGTH: 120
<212> TYPE: PRT
<213> ORGANISM: Artificial Sequence
<220> FEATURE:
<223> OTHER INFORMATION: MP1521_H5 Nanobody (CA15890)

<400> SEQUENCE: 44

Gln Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Ser Thr Tyr
20 25 30

Ser Met Ser Trp Val Arg Gln Ala Pro Gly Lys Gly Leu Glu Trp Val
35 40 45

Ser Arg Ile Leu Thr Asp Gly Gly Thr Thr Ser Tyr Pro Asp Ser Val
50 55 60

Lys Gly Arg Phe Thr Ile Ser Arg Asp Asn Ala Lys Asn Thr Leu Tyr
65 70 75 80

Leu Gln Met Asn Asn Leu Lys Pro Glu Asp Thr Ala Val Tyr Tyr Cys
85 90 95

Ala Arg Gly Trp Pro Ser Asp Gly Tyr Ser Gly Gly Tyr Arg Gly Gln
100 105 110

Gly Thr Gln Val Thr Val Ser Ser
115 120

<210> SEQ ID NO 45
<211> LENGTH: 125
<212> TYPE: PRT
<213> ORGANISM: Artificial Sequence
<220> FEATURE:
<223> OTHER INFORMATION: MP1522_C10 Nanobody (CA15891)

<400> SEQUENCE: 45

Gln Val Gln Leu Val Glu Ser Gly Gly Gly Leu Val Gln Ala Gly Gly
1 5 10 15

Ser Leu Arg Leu Ala Cys Ala Ala Ser Gly Arg Thr Ser Gly Ser Tyr
20 25 30

Ala Ile Gly Trp Phe Arg Gln Ala Pro Gly Lys Glu Arg Glu Phe Ala
35 40 45

Ala Ala Ile Ser Phe Thr Ala Gly Val Thr Tyr Tyr Ser Asn Ser Val
50 55 60

Lys Gly Arg Phe Thr Ile Ser Arg Asp Ser Ala Lys Asn Thr Ala Tyr
65 70 75 80

Leu Gln Met Asn Thr Leu Lys Pro Glu Asp Thr Ala Val Tyr Tyr Cys
85 90 95

Ala Thr Leu Pro Ser Leu Val Leu Ile Leu Thr Ala Lys Pro Asn Ile
100 105 110

Gly Tyr Trp Gly Gln Gly Thr Gln Val Thr Val Ser Ser
115 120 125

<210> SEQ ID NO 46
<211> LENGTH: 122
<212> TYPE: PRT
<213> ORGANISM: Artificial Sequence
<220> FEATURE:
<223> OTHER INFORMATION: MP1522_A5 Nanobody (CA15892)

<400> SEQUENCE: 46

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Ser
            20                  25                  30

Tyr Met Ser Trp Val Arg Gln Ala Pro Gly Lys Gly Pro Glu Trp Val
        35                  40                  45

Ser Ser Ile Ser Pro Ser Ala Trp Ile Ile Thr His Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn His Leu Lys Pro Glu Asp Ala Ala Leu Tyr Tyr Cys
                85                  90                  95

Ala Arg Arg Gln Gly Tyr Asp Gly Tyr Val Pro Ser Arg Asp Tyr Trp
            100                 105                 110

Gly Gln Gly Thr Gln Val Thr Val Ser Ser
        115                 120
```

<210> SEQ ID NO 47
<211> LENGTH: 117
<212> TYPE: PRT
<213> ORGANISM: Artificial Sequence
<220> FEATURE:
<223> OTHER INFORMATION: MP1521_B4 Nanobody (CA15893)

<400> SEQUENCE: 47

```
Gln Val Gln Leu Val Glu Ser Gly Gly Gly Leu Val Gln Pro Gly Gly
1               5                   10                  15

Ser Leu Arg Leu Ser Cys Ala Ala Ser Lys Ser Phe Phe Asn Ile Tyr
            20                  25                  30

Asp Leu Ala Trp Tyr Arg Gln Ala Pro Gly Lys Gln Arg Glu Leu Val
        35                  40                  45

Ala Ser Ile Thr Lys Val Gly Ser Thr Asn Tyr Ala Asp Ser Val Lys
    50                  55                  60

Gly Arg Phe Thr Thr Ser Arg Asp Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Leu Val Ser Pro Gly Gly Val Tyr Asn Tyr Trp Gly Gln Gly Thr Gln
            100                 105                 110

Val Thr Val Ser Ser
        115
```

<210> SEQ ID NO 48
<211> LENGTH: 115
<212> TYPE: PRT
<213> ORGANISM: Artificial Sequence
<220> FEATURE:
<223> OTHER INFORMATION: MP1521_F3 Nanobody (CA15894)

<400> SEQUENCE: 48

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Gly Phe Gly Pro Asn
            20                  25                  30

Val Met Gly Trp Tyr Arg Gln Ala Pro Gly Lys Arg Arg Glu Leu Val
        35                  40                  45

Ala Thr Ile Asn Arg Ile Gly Asn Ile Asn Tyr Gly Asp Ser Val Lys
```

-continued

```
    50                  55                  60

Gly Arg Phe Thr Leu Ser Arg Glu Ile Ala Val Asn Thr Val Tyr Leu
65                  70                  75                  80

Gln Met Asn Ser Leu Lys Pro Glu Asp Ala Ala Asn Tyr Tyr Cys Tyr
                85                  90                  95

Ala Ala Lys Tyr Gly Val Asp Tyr Trp Gly Lys Gly Thr Gln Val Thr
            100                 105                 110

Val Ser Ser
        115


<210> SEQ ID NO 49
<211> LENGTH: 111
<212> TYPE: PRT
<213> ORGANISM: Artificial Sequence
<220> FEATURE:
<223> OTHER INFORMATION: MP1521_B1 Nanobody (CA15895)

<400> SEQUENCE: 49

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ser
            20                  25                  30

Tyr Met Asp Trp Val Arg Gln Ala Pro Gly Lys Gly Ile Glu Trp Val
        35                  40                  45

Ser Thr Ile Ser Pro Gly Gly Arg Ile Thr Tyr Ala Val Ser Val Glu
    50                  55                  60

Gly Arg Phe Thr Leu Ser Arg Asp Asn Ala Lys Asn Thr Leu Ser Leu
65                  70                  75                  80

Gln Met Asn Glu Leu Lys Pro Glu Asp Thr Ala Val Tyr Tyr Cys Arg
                85                  90                  95

Arg Leu Gly Glu Lys Gly Gln Gly Thr Gln Val Thr Val Ser Ser
            100                 105                 110


<210> SEQ ID NO 50
<211> LENGTH: 115
<212> TYPE: PRT
<213> ORGANISM: Artificial Sequence
<220> FEATURE:
<223> OTHER INFORMATION: MP1521_E1 Nanobody (CA15896)

<400> SEQUENCE: 50

Gln Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Thr Arg Ser Pro
            20                  25                  30

Thr Met Ser Trp Ala Arg Gln Ala Pro Gly Arg Gln Arg Glu Trp Val
        35                  40                  45

Thr Ser Ile Leu Gly Thr Gly Arg Thr Asp Tyr Ala Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Asn Leu Lys Pro Glu Asp Ser Ala Val Tyr Tyr Cys Tyr
                85                  90                  95

Thr Val Leu Asn Gly Arg Pro Ser Trp Gly Gln Gly Thr Gln Val Thr
            100                 105                 110

Val Ser Ser
        115
```

<210> SEQ ID NO 51
<211> LENGTH: 775
<212> TYPE: PRT
<213> ORGANISM: Artificial Sequence
<220> FEATURE:
<223> OTHER INFORMATION: circular permutated E.coli Ygjk protein (PDB 3WFS; cYgjk)

<400> SEQUENCE: 51

Lys Glu Glu Thr Gln Ser Gly Leu Asn Asn Tyr Ala Arg Val Val Glu
1               5                   10                  15

Lys Gly Gln Tyr Asp Ser Leu Glu Ile Pro Ala Gln Val Ala Ala Ser
            20                  25                  30

Trp Glu Ser Gly Arg Asp Asp Ala Ala Val Phe Gly Phe Ile Asp Lys
        35                  40                  45

Glu Gln Leu Asp Lys Tyr Val Ala Asn Gly Gly Lys Arg Ser Asp Trp
    50                  55                  60

Thr Val Lys Phe Ala Glu Asn Arg Ser Gln Asp Gly Thr Leu Leu Gly
65                  70                  75                  80

Tyr Ser Leu Leu Gln Glu Ser Val Asp Gln Ala Ser Tyr Met Tyr Ser
                85                  90                  95

Asp Asn His Tyr Leu Ala Glu Met Ala Thr Ile Leu Gly Lys Pro Glu
            100                 105                 110

Glu Ala Lys Arg Tyr Arg Gln Leu Ala Gln Gln Leu Ala Asp Tyr Ile
        115                 120                 125

Asn Thr Cys Met Phe Asp Pro Thr Thr Gln Phe Tyr Tyr Asp Val Arg
    130                 135                 140

Ile Glu Asp Lys Pro Leu Ala Asn Gly Cys Ala Gly Lys Pro Ile Val
145                 150                 155                 160

Glu Arg Gly Lys Gly Pro Glu Gly Trp Ser Pro Leu Phe Asn Gly Ala
                165                 170                 175

Ala Thr Gln Ala Asn Ala Asp Ala Val Val Lys Val Met Leu Asp Pro
            180                 185                 190

Lys Glu Phe Asn Thr Phe Val Pro Leu Gly Thr Ala Ala Leu Thr Asn
        195                 200                 205

Pro Ala Phe Gly Ala Asp Ile Tyr Trp Arg Gly Arg Val Trp Val Asp
    210                 215                 220

Gln Phe Trp Phe Gly Leu Lys Gly Met Glu Arg Tyr Gly Tyr Arg Asp
225                 230                 235                 240

Asp Ala Leu Lys Leu Ala Asp Thr Phe Phe Arg His Ala Lys Gly Leu
                245                 250                 255

Thr Ala Asp Gly Pro Ile Gln Glu Asn Tyr Asn Pro Leu Thr Gly Ala
            260                 265                 270

Gln Gln Gly Ala Pro Asn Phe Ser Trp Ser Ala Ala His Leu Tyr Met
        275                 280                 285

Leu Tyr Asn Asp Phe Phe Arg Lys Gln Ala Ser Gly Gly Gly Ser Gly
    290                 295                 300

Gly Gly Gly Ser Gly Gly Gly Gly Ser Gly Asn Ala Asp Asn Tyr Lys
305                 310                 315                 320

Asn Val Ile Asn Arg Thr Gly Ala Pro Gln Tyr Met Lys Asp Tyr Asp
                325                 330                 335

Tyr Asp Asp His Gln Arg Phe Asn Pro Phe Phe Asp Leu Gly Ala Trp
            340                 345                 350

His Gly His Leu Leu Pro Asp Gly Pro Asn Thr Met Gly Gly Phe Pro
        355                 360                 365

-continued

```
Gly Val Ala Leu Leu Thr Glu Glu Tyr Ile Asn Phe Met Ala Ser Asn
    370                 375                 380

Phe Asp Arg Leu Thr Val Trp Gln Asp Gly Lys Lys Val Asp Phe Thr
385                 390                 395                 400

Leu Glu Ala Tyr Ser Ile Pro Gly Ala Leu Val Gln Lys Leu Thr Ala
                405                 410                 415

Lys Asp Val Gln Val Glu Met Thr Leu Arg Phe Ala Thr Pro Arg Thr
            420                 425                 430

Ser Leu Leu Glu Thr Lys Ile Thr Ser Asn Lys Pro Leu Asp Leu Val
        435                 440                 445

Trp Asp Gly Glu Leu Leu Glu Lys Leu Glu Ala Lys Glu Gly Lys Pro
    450                 455                 460

Leu Ser Asp Lys Thr Ile Ala Gly Glu Tyr Pro Asp Tyr Gln Arg Lys
465                 470                 475                 480

Ile Ser Ala Thr Arg Asp Gly Leu Lys Val Thr Phe Gly Lys Val Arg
                485                 490                 495

Ala Thr Trp Asp Leu Leu Thr Ser Gly Glu Ser Glu Tyr Gln Val His
            500                 505                 510

Lys Ser Leu Pro Val Gln Thr Glu Ile Asn Gly Asn Arg Phe Thr Ser
        515                 520                 525

Lys Ala His Ile Asn Gly Ser Thr Thr Leu Tyr Thr Thr Tyr Ser His
    530                 535                 540

Leu Leu Thr Ala Gln Glu Val Ser Lys Glu Gln Met Gln Ile Arg Asp
545                 550                 555                 560

Ile Leu Ala Arg Pro Ala Phe Tyr Leu Thr Ala Ser Gln Gln Arg Trp
                565                 570                 575

Glu Glu Tyr Leu Lys Lys Gly Leu Thr Asn Pro Asp Ala Thr Pro Glu
            580                 585                 590

Gln Thr Arg Val Ala Val Lys Ala Ile Glu Thr Leu Asn Gly Asn Trp
        595                 600                 605

Arg Ser Pro Gly Gly Ala Val Lys Phe Asn Thr Val Thr Pro Ser Val
    610                 615                 620

Thr Gly Arg Trp Phe Ser Gly Asn Gln Thr Trp Pro Trp Asp Thr Trp
625                 630                 635                 640

Lys Gln Ala Phe Ala Met Ala His Phe Asn Pro Asp Ile Ala Lys Glu
                645                 650                 655

Asn Ile Arg Ala Val Phe Ser Trp Gln Ile Gln Pro Gly Asp Ser Val
            660                 665                 670

Arg Pro Gln Asp Val Gly Phe Val Pro Asp Leu Ile Ala Trp Asn Leu
        675                 680                 685

Ser Pro Glu Arg Gly Gly Asp Gly Gly Asn Trp Asn Glu Arg Asn Thr
    690                 695                 700

Lys Pro Ser Leu Ala Ala Trp Ser Val Met Glu Val Tyr Asn Val Thr
705                 710                 715                 720

Gln Asp Lys Thr Trp Val Ala Glu Met Tyr Pro Lys Leu Val Ala Tyr
                725                 730                 735

His Asp Trp Trp Leu Arg Asn Arg Asp His Asn Gly Asn Gly Val Pro
            740                 745                 750

Glu Tyr Gly Ala Thr Arg Asp Lys Ala His Asn Thr Glu Ser Gly Glu
        755                 760                 765

Met Leu Phe Thr Val Lys Lys
    770                 775
```

<210> SEQ ID NO 52
<211> LENGTH: 896
<212> TYPE: PRT
<213> ORGANISM: Artificial Sequence
<220> FEATURE:
<223> OTHER INFORMATION: MbNbF3cYgjk_NO MegaBody

<400> SEQUENCE: 52

```
Gln Val Gln Leu Val Glu Ser Gly Gly Gly Leu Val Lys Glu Glu Thr
1               5                   10                  15

Gln Ser Gly Leu Asn Asn Tyr Ala Arg Val Val Glu Lys Gly Gln Tyr
            20                  25                  30

Asp Ser Leu Glu Ile Pro Ala Gln Val Ala Ala Ser Trp Glu Ser Gly
        35                  40                  45

Arg Asp Asp Ala Ala Val Phe Gly Phe Ile Asp Lys Glu Gln Leu Asp
    50                  55                  60

Lys Tyr Val Ala Asn Gly Gly Lys Arg Ser Asp Trp Thr Val Lys Phe
65                  70                  75                  80

Ala Glu Asn Arg Ser Gln Asp Gly Thr Leu Leu Gly Tyr Ser Leu Leu
                85                  90                  95

Gln Glu Ser Val Asp Gln Ala Ser Tyr Met Tyr Ser Asp Asn His Tyr
            100                 105                 110

Leu Ala Glu Met Ala Thr Ile Leu Gly Lys Pro Glu Glu Ala Lys Arg
        115                 120                 125

Tyr Arg Gln Leu Ala Gln Gln Leu Ala Asp Tyr Ile Asn Thr Cys Met
    130                 135                 140

Phe Asp Pro Thr Thr Gln Phe Tyr Tyr Asp Val Arg Ile Glu Asp Lys
145                 150                 155                 160

Pro Leu Ala Asn Gly Cys Ala Gly Lys Pro Ile Val Glu Arg Gly Lys
                165                 170                 175

Gly Pro Glu Gly Trp Ser Pro Leu Phe Asn Gly Ala Ala Thr Gln Ala
            180                 185                 190

Asn Ala Asp Ala Val Val Lys Val Met Leu Asp Pro Lys Glu Phe Asn
        195                 200                 205

Thr Phe Val Pro Leu Gly Thr Ala Ala Leu Thr Asn Pro Ala Phe Gly
    210                 215                 220

Ala Asp Ile Tyr Trp Arg Gly Arg Val Trp Val Asp Gln Phe Trp Phe
225                 230                 235                 240

Gly Leu Lys Gly Met Glu Arg Tyr Gly Tyr Arg Asp Asp Ala Leu Lys
                245                 250                 255

Leu Ala Asp Thr Phe Phe Arg His Ala Lys Gly Leu Thr Ala Asp Gly
            260                 265                 270

Pro Ile Gln Glu Asn Tyr Asn Pro Leu Thr Gly Ala Gln Gln Gly Ala
        275                 280                 285

Pro Asn Phe Ser Trp Ser Ala Ala His Leu Tyr Met Leu Tyr Asn Asp
    290                 295                 300

Phe Phe Arg Lys Gln Ala Ser Gly Gly Gly Ser Gly Gly Gly Gly Ser
305                 310                 315                 320

Gly Gly Gly Gly Ser Gly Asn Ala Asp Asn Tyr Lys Asn Val Ile Asn
                325                 330                 335

Arg Thr Gly Ala Pro Gln Tyr Met Lys Asp Tyr Asp Tyr Asp Asp His
            340                 345                 350

Gln Arg Phe Asn Pro Phe Phe Asp Leu Gly Ala Trp His Gly His Leu
        355                 360                 365
```

-continued

```
Leu Pro Asp Gly Pro Asn Thr Met Gly Gly Phe Pro Gly Val Ala Leu
    370                 375                 380

Leu Thr Glu Glu Tyr Ile Asn Phe Met Ala Ser Asn Phe Asp Arg Leu
385                 390                 395                 400

Thr Val Trp Gln Asp Gly Lys Lys Val Asp Phe Thr Leu Glu Ala Tyr
                405                 410                 415

Ser Ile Pro Gly Ala Leu Val Gln Lys Leu Thr Ala Lys Asp Val Gln
            420                 425                 430

Val Glu Met Thr Leu Arg Phe Ala Thr Pro Arg Thr Ser Leu Leu Glu
        435                 440                 445

Thr Lys Ile Thr Ser Asn Lys Pro Leu Asp Leu Val Trp Asp Gly Glu
    450                 455                 460

Leu Leu Glu Lys Leu Glu Ala Lys Glu Gly Lys Pro Leu Ser Asp Lys
465                 470                 475                 480

Thr Ile Ala Gly Glu Tyr Pro Asp Tyr Gln Arg Lys Ile Ser Ala Thr
                485                 490                 495

Arg Asp Gly Leu Lys Val Thr Phe Gly Lys Val Arg Ala Thr Trp Asp
            500                 505                 510

Leu Leu Thr Ser Gly Glu Ser Glu Tyr Gln Val His Lys Ser Leu Pro
        515                 520                 525

Val Gln Thr Glu Ile Asn Gly Asn Arg Phe Thr Ser Lys Ala His Ile
    530                 535                 540

Asn Gly Ser Thr Thr Leu Tyr Thr Thr Tyr Ser His Leu Leu Thr Ala
545                 550                 555                 560

Gln Glu Val Ser Lys Glu Gln Met Gln Ile Arg Asp Ile Leu Ala Arg
                565                 570                 575

Pro Ala Phe Tyr Leu Thr Ala Ser Gln Gln Arg Trp Glu Glu Tyr Leu
            580                 585                 590

Lys Lys Gly Leu Thr Asn Pro Asp Ala Thr Pro Glu Gln Thr Arg Val
        595                 600                 605

Ala Val Lys Ala Ile Glu Thr Leu Asn Gly Asn Trp Arg Ser Pro Gly
    610                 615                 620

Gly Ala Val Lys Phe Asn Thr Val Thr Pro Ser Val Thr Gly Arg Trp
625                 630                 635                 640

Phe Ser Gly Asn Gln Thr Trp Pro Trp Asp Thr Trp Lys Gln Ala Phe
                645                 650                 655

Ala Met Ala His Phe Asn Pro Asp Ile Ala Lys Glu Asn Ile Arg Ala
            660                 665                 670

Val Phe Ser Trp Gln Ile Gln Pro Gly Asp Ser Val Arg Pro Gln Asp
        675                 680                 685

Val Gly Phe Val Pro Asp Leu Ile Ala Trp Asn Leu Ser Pro Glu Arg
    690                 695                 700

Gly Gly Asp Gly Gly Asn Trp Asn Glu Arg Asn Thr Lys Pro Ser Leu
705                 710                 715                 720

Ala Ala Trp Ser Val Met Glu Val Tyr Asn Val Thr Gln Asp Lys Thr
                725                 730                 735

Trp Val Ala Glu Met Tyr Pro Lys Leu Val Ala Tyr His Asp Trp Trp
            740                 745                 750

Leu Arg Asn Arg Asp His Asn Gly Asn Gly Val Pro Glu Tyr Gly Ala
        755                 760                 765

Thr Arg Asp Lys Ala His Asn Thr Glu Ser Gly Glu Met Leu Phe Thr
    770                 775                 780

Val Lys Lys Ser Leu Arg Leu Ser Cys Ala Ala Ser Gly Ser Gly Phe
```

785 790 795 800

Gly Pro Asn Val Met Gly Trp Tyr Arg Gln Ala Pro Gly Lys Arg Arg
805 810 815

Glu Leu Val Ala Thr Ile Asn Arg Ile Gly Asn Ile Asn Tyr Gly Asp
820 825 830

Ser Val Lys Gly Arg Phe Thr Leu Ser Arg Glu Ile Ala Val Asn Thr
835 840 845

Val Tyr Leu Gln Met Asn Ser Leu Lys Pro Glu Asp Ala Ala Asn Tyr
850 855 860

Tyr Cys Tyr Ala Ala Lys Tyr Gly Val Asp Tyr Trp Gly Lys Gly Thr
865 870 875 880

Gln Val Thr Val Ser Ser His His His His His His Glu Pro Glu Ala
885 890 895

<210> SEQ ID NO 53
<211> LENGTH: 511
<212> TYPE: PRT
<213> ORGANISM: Artificial Sequence
<220> FEATURE:
<223> OTHER INFORMATION: MbNb1_B9c7HopQ MegaBody (CA15898)

<400> SEQUENCE: 53

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

Thr Leu Ile Gln Glu Leu Gly Asn Asn Thr Tyr Glu Gln Leu Ser Arg
225 230 235 240

Leu Leu Thr Asn Asp Asn Gly Thr Asn Ser Lys Thr Ser Ala Gln Ala
245 250 255

Ile Asn Gln Ala Val Asn Asn Leu Asn Glu Arg Ala Lys Thr Leu Ala

```
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Leu
                405                 410                 415

Cys Ser Ile Pro Met Gly Trp Phe Arg Gln Ala Pro Gly Lys Glu Arg
            420                 425                 430

Glu Phe Val Ala Ala Ile Arg Trp Ser Gly Gly Ser Thr Tyr Tyr Ala
        435                 440                 445

Asp Ser Val Lys Gly Arg Phe Ser Ile Ser Lys Asp Asn Ala Lys Asn
    450                 455                 460

Thr Val Tyr Leu Gln Met Asn Asn Leu Lys Pro Glu Asp Thr Ala Thr
465                 470                 475                 480

Tyr Tyr Cys Ala Ser Ala Ala Pro Tyr Ser Ser Trp Ser Arg Gly Leu
                485                 490                 495

Glu Tyr Asp Tyr Trp Gly Gln Gly Thr Gln Val Thr Val Ser Ser
            500                 505                 510


<210> SEQ ID NO 54
<211> LENGTH: 504
<212> TYPE: PRT
<213> ORGANISM: Artificial Sequence
<220> FEATURE:
<223> OTHER INFORMATION: MbNbG9c7HopQ MegaBody (CA15899)

<400> SEQUENCE: 54

Gln Val Gln Leu Val Glu Ser Gly Gly Gly Ser Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
```

-continued

```
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Phe
                405                 410                 415

Ser Thr Tyr Arg Met Gly Trp Phe Arg Gln Ala Pro Gly Lys Glu Arg
            420                 425                 430

Glu Phe Val Ala Gly Trp Asn Ser Ile Asn Ile Tyr Tyr Ala Asp Ser
        435                 440                 445

Val Lys Gly Arg Phe Thr Ile Ser Gly Asp Asn Ala Lys Ser Thr Val
    450                 455                 460

Tyr Leu Gln Met Asn Ser Leu Lys Pro Glu Asp Thr Ala Val Tyr Tyr
465                 470                 475                 480

Cys Ala Ala Arg Gly Leu Gly Gln Thr Glu Tyr Asn Tyr Trp Gly Gln
                485                 490                 495

Gly Thr Gln Val Thr Val Ser Ser
            500
```

<210> SEQ ID NO 55
<211> LENGTH: 506
<212> TYPE: PRT
<213> ORGANISM: Artificial Sequence
<220> FEATURE:
<223> OTHER INFORMATION: MbNbA12c7HopQ MegaBody (CA15900)

<400> SEQUENCE: 55

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

Thr Leu Ile Gln Glu Leu Gly Asn Asn Thr Tyr Glu Gln Leu Ser Arg
225 230 235 240

Leu Leu Thr Asn Asp Asn Gly Thr Asn Ser Lys Thr Ser Ala Gln Ala
245 250 255

Ile Asn Gln Ala Val Asn Asn Leu Asn Glu Arg Ala Lys Thr Leu Ala
260 265 270

Gly Gly Thr Thr Asn Ser Pro Ala Tyr Gln Ala Thr Leu Leu Ala Leu
275 280 285

Arg Ser Val Leu Gly Leu Trp Asn Ser Met Gly Tyr Ala Val Ile Cys
290 295 300

Gly Gly Tyr Thr Lys Ser Pro Gly Glu Asn Asn Gln Lys Asp Phe His
305 310 315 320

Tyr Thr Asp Glu Asn Gly Asn Gly Thr Thr Ile Asn Cys Gly Gly Ser
325 330 335

Thr Asn Ser Asn Gly Thr His Ser Tyr Asn Gly Thr Asn Thr Leu Lys
340 345 350

Ala Asp Lys Asn Val Ser Leu Ser Ile Glu Gln Tyr Glu Lys Ile His
355 360 365

Glu Ala Tyr Gln Ile Leu Ser Lys Ala Leu Lys Gln Ala Gly Leu Ala
370 375 380

Pro Leu Asn Ser Lys Gly Glu Lys Leu Glu Ala His Val Thr Thr Ser
385 390 395 400

```
Lys Tyr Gly Ser Leu Arg Leu Ser Cys Ala Ala Ser Gly Arg Thr Phe
                405                 410                 415

Ser Ser Tyr Asn Met Ala Trp Phe Arg Gln Val Pro Gly Lys Glu Arg
            420                 425                 430

Glu Phe Val Ala Ser Ile Ala Arg Thr Gly Ser Gly Thr Tyr Tyr Arg
        435                 440                 445

Asp Ser Val Lys Gly Arg Phe Thr Ile Ser Arg Asp Asn Ala Lys Asn
    450                 455                 460

Thr Val Tyr Leu Gln Met Asn Ser Leu Lys Pro Gln Asp Thr Ala Val
465                 470                 475                 480

Tyr Tyr Cys Thr Ala Gly Gly Ser Leu Ala Thr Ile Ser Asp Tyr Trp
                485                 490                 495

Gly Gln Gly Thr Gln Val Thr Val Ser Ser
            500                 505


<210> SEQ ID NO 56
<211> LENGTH: 511
<212> TYPE: PRT
<213> ORGANISM: Artificial Sequence
<220> FEATURE:
<223> OTHER INFORMATION: MbNbB7c7HopQ MegaBody (CA15901)

<400> SEQUENCE: 56

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255
```

```
Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Ser Phe
                405                 410                 415

Ser Ser Tyr Gly Met Gly Trp Phe Arg Gln Ala Pro Gly Lys Glu Arg
            420                 425                 430

Glu Phe Ala Ala Gly Ile Thr Gly Thr Ala Gly Ile Thr Tyr Tyr Thr
        435                 440                 445

Asp Ser Val Lys Gly Arg Phe Thr Ile Ser Arg Asp Asn Ala Lys Asn
    450                 455                 460

Thr Val Tyr Leu Gln Met Asn Asn Leu Lys Pro Glu Asp Thr Ala Val
465                 470                 475                 480

Tyr Tyr Cys Ala Ala Gly Leu Thr Ser Tyr Ala Gly Arg Gly Ala Ala
                485                 490                 495

Gly Tyr Asp Tyr Trp Gly Gln Gly Thr Gln Val Thr Val Ser Ser
            500                 505                 510


<210> SEQ ID NO 57
<211> LENGTH: 513
<212> TYPE: PRT
<213> ORGANISM: Artificial Sequence
<220> FEATURE:
<223> OTHER INFORMATION: MbNbE8c7HopQ MegaBody (CA15902)

<400> SEQUENCE: 57

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110
```

```
Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Pro Glu Arg Thr Phe
                405                 410                 415

Ser Ser His His Met Ala Trp Phe Arg Gln Ala Pro Gly Met Glu Arg
            420                 425                 430

Glu Phe Val Ala Gly Ile Ser Trp Ser Phe Gly Thr Thr Ser Tyr Ala
        435                 440                 445

Asp Ser Val Lys Gly Arg Phe Thr Ile Ser Arg Asp Asn Ala Lys Gly
    450                 455                 460

Thr Val Tyr Leu Gln Met Asn Ser Leu Lys Pro Glu Asp Thr Ala Val
465                 470                 475                 480

Tyr Tyr Cys Ala Ala Met Pro Thr Tyr Arg Gly Arg Lys Tyr Tyr Leu
                485                 490                 495

Ala Asp Asp Tyr Asn Tyr Trp Gly Gln Gly Thr Gln Val Thr Val Ser
            500                 505                 510

Ser
```

<210> SEQ ID NO 58
<211> LENGTH: 509
<212> TYPE: PRT
<213> ORGANISM: Artificial Sequence
<220> FEATURE:
<223> OTHER INFORMATION: MbNb2_B9c7HopQ MegaBody (CA15903)

<400> SEQUENCE: 58

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
```

-continued

```
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Val Arg Ser Ala Arg Thr Phe
                405                 410                 415

Gly Ser Val Ala Met Gly Trp Phe Arg Gln Ala Pro Gly Lys Glu Arg
            420                 425                 430

Glu Phe Val Thr Ala Ile Asp Trp Ser Gly Ser Asn Thr Leu Tyr Ala
        435                 440                 445

Asp Ser Val Lys Gly Arg Phe Thr Ile Ser Arg Asp Asn Ala Lys Asn
    450                 455                 460

Thr Val Tyr Leu Gln Met Asn Ser Leu Lys Pro Asp Asp Thr Ala Val
465                 470                 475                 480

Tyr Tyr Cys Ala Ala Ser Arg Arg Val Val Val Thr Thr Ser Asp Phe
                485                 490                 495

Asp Ser Trp Gly Gln Gly Thr Gln Val Thr Val Ser Ser
            500                 505


<210> SEQ ID NO 59
<211> LENGTH: 504
<212> TYPE: PRT
<213> ORGANISM: Artificial Sequence
<220> FEATURE:
<223> OTHER INFORMATION: MbNbE4c7HopQ MegaBody (CA15191)

<400> SEQUENCE: 59

Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
```

-continued

```
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Arg Thr Phe
                405                 410                 415

Gly Ser Thr Phe Met Gly Trp Phe Arg Gln Ala Pro Gly Lys Glu Arg
            420                 425                 430

Asp Phe Val Ala Ser Ile Thr Trp Asn Arg Gly Leu Thr Thr Tyr Ala
        435                 440                 445

Asp Ser Val Lys Gly Arg Phe Thr Ile Ser Arg Asp Ser Ala Lys Asn
    450                 455                 460

Thr Val Asp Leu Gln Met Asn Asn Leu Lys Pro Glu Asp Thr Ala Val
465                 470                 475                 480

Tyr Tyr Cys Val Leu Gly Met Gly Thr Ser Phe Ala Ser Trp Gly Gln
                485                 490                 495

Gly Thr Gln Val Thr Val Ser Ser
            500
```

<210> SEQ ID NO 60
<211> LENGTH: 507
<212> TYPE: PRT
<213> ORGANISM: Artificial Sequence
<220> FEATURE:
<223> OTHER INFORMATION: MbNbH5c7HopQ MegaBody (CA15904)

<400> SEQUENCE: 60

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
```

-continued

```
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Phe Thr Phe
                405                 410                 415

Ser Thr Tyr Ser Met Ser Trp Val Arg Gln Ala Pro Gly Lys Gly Leu
            420                 425                 430

Glu Trp Val Ser Arg Ile Leu Thr Asp Gly Gly Thr Thr Ser Tyr Pro
        435                 440                 445

Asp Ser Val Lys Gly Arg Phe Thr Ile Ser Arg Asp Asn Ala Lys Asn
    450                 455                 460

Thr Leu Tyr Leu Gln Met Asn Asn Leu Lys Pro Glu Asp Thr Ala Val
465                 470                 475                 480

Tyr Tyr Cys Ala Arg Gly Trp Pro Ser Asp Gly Tyr Ser Gly Gly Tyr
                485                 490                 495

Arg Gly Gln Gly Thr Gln Val Thr Val Ser Ser
            500                 505
```

<210> SEQ ID NO 61
<211> LENGTH: 512
<212> TYPE: PRT
<213> ORGANISM: Artificial Sequence
<220> FEATURE:
<223> OTHER INFORMATION: MbNbC10c7HopQ MegaBody (CA15905)

<400> SEQUENCE: 61

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365
```

Glu Ala Tyr Gln Ile Leu Ser Lys Ala Leu Lys Gln Ala Gly Leu Ala
370 375 380

Pro Leu Asn Ser Lys Gly Glu Lys Leu Glu Ala His Val Thr Thr Ser
385 390 395 400

Lys Tyr Gly Ser Leu Arg Leu Ser Cys Ala Ala Ser Gly Arg Thr Ser
405 410 415

Gly Ser Tyr Ala Ile Gly Trp Phe Arg Gln Ala Pro Gly Lys Glu Arg
420 425 430

Glu Phe Ala Ala Ala Ile Ser Phe Thr Ala Gly Val Thr Tyr Tyr Ser
435 440 445

Asn Ser Val Lys Gly Arg Phe Thr Ile Ser Arg Asp Ser Ala Lys Asn
450 455 460

Thr Ala Tyr Leu Gln Met Asn Thr Leu Lys Pro Glu Asp Thr Ala Val
465 470 475 480

Tyr Tyr Cys Ala Thr Leu Pro Ser Leu Val Leu Ile Leu Thr Ala Lys
485 490 495

Pro Asn Ile Gly Tyr Trp Gly Gln Gly Thr Gln Val Thr Val Ser Ser
500 505 510

<210> SEQ ID NO 62
<211> LENGTH: 509
<212> TYPE: PRT
<213> ORGANISM: Artificial Sequence
<220> FEATURE:
<223> OTHER INFORMATION: MbNbA5c7HopQ MegaBody (CA15906)

<400> SEQUENCE: 62

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

```
Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Phe Ala Phe
                405                 410                 415

Ser Asn Ser Tyr Met Ser Trp Val Arg Gln Ala Pro Gly Lys Gly Pro
            420                 425                 430

Glu Trp Val Ser Ser Ile Ser Pro Ser Ala Trp Ile Ile Thr His Gly
        435                 440                 445

Asp Ser Val Lys Gly Arg Phe Thr Ile Ser Arg Asp Asn Ala Lys Asn
    450                 455                 460

Thr Leu Tyr Leu Gln Met Asn His Leu Lys Pro Glu Asp Ala Ala Leu
465                 470                 475                 480

Tyr Tyr Cys Ala Arg Arg Gln Gly Tyr Asp Gly Tyr Val Pro Ser Arg
                485                 490                 495

Asp Tyr Trp Gly Gln Gly Thr Gln Val Thr Val Ser Ser
            500                 505
```

<210> SEQ ID NO 63
<211> LENGTH: 504
<212> TYPE: PRT
<213> ORGANISM: Artificial Sequence
<220> FEATURE:
<223> OTHER INFORMATION: MbNbB4c7HopQ MegaBody (CA15907)

<400> SEQUENCE: 63

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
65                  70                  75                  80
```

-continued

```
Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Lys Ser Phe Phe
                405                 410                 415

Asn Ile Tyr Asp Leu Ala Trp Tyr Arg Gln Ala Pro Gly Lys Gln Arg
            420                 425                 430

Glu Leu Val Ala Ser Ile Thr Lys Val Gly Ser Thr Asn Tyr Ala Asp
        435                 440                 445

Ser Val Lys Gly Arg Phe Thr Thr Ser Arg Asp Asn Ala Lys Lys Thr
    450                 455                 460

Val Tyr Leu Gln Met Asn Ser Leu Lys Pro Glu Asp Thr Ala Val Tyr
465                 470                 475                 480

Tyr Cys Asn Leu Val Ser Pro Gly Gly Val Tyr Asn Tyr Trp Gly Gln
                485                 490                 495
```

Gly Thr Gln Val Thr Val Ser Ser
500

<210> SEQ ID NO 64
<211> LENGTH: 502
<212> TYPE: PRT
<213> ORGANISM: Artificial Sequence
<220> FEATURE:
<223> OTHER INFORMATION: MbNbF3c7HopQ MegaBody (CA15192)

<400> SEQUENCE: 64

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

Phe Asn Asn Gln Thr Pro Gln Ile Asn Gln Ala Gln Asn Leu Ala Asn
210 215 220

Thr Leu Ile Gln Glu Leu Gly Asn Asn Thr Tyr Glu Gln Leu Ser Arg
225 230 235 240

Leu Leu Thr Asn Asp Asn Gly Thr Asn Ser Lys Thr Ser Ala Gln Ala
245 250 255

Ile Asn Gln Ala Val Asn Asn Leu Asn Glu Arg Ala Lys Thr Leu Ala
260 265 270

Gly Gly Thr Thr Asn Ser Pro Ala Tyr Gln Ala Thr Leu Leu Ala Leu
275 280 285

Arg Ser Val Leu Gly Leu Trp Asn Ser Met Gly Tyr Ala Val Ile Cys
290 295 300

Gly Gly Tyr Thr Lys Ser Pro Gly Glu Asn Asn Gln Lys Asp Phe His
305 310 315 320

Tyr Thr Asp Glu Asn Gly Asn Gly Thr Thr Ile Asn Cys Gly Gly Ser
325 330 335

Thr Asn Ser Asn Gly Thr His Ser Tyr Asn Gly Thr Asn Thr Leu Lys
340 345 350

-continued

Ala Asp Lys Asn Val Ser Leu Ser Ile Glu Gln Tyr Glu Lys Ile His
355 360 365

Glu Ala Tyr Gln Ile Leu Ser Lys Ala Leu Lys Gln Ala Gly Leu Ala
370 375 380

Pro Leu Asn Ser Lys Gly Glu Lys Leu Glu Ala His Val Thr Thr Ser
385 390 395 400

Lys Tyr Gly Ser Leu Arg Leu Ser Cys Ala Ala Ser Gly Ser Gly Phe
405 410 415

Gly Pro Asn Val Met Gly Trp Tyr Arg Gln Ala Pro Gly Lys Arg Arg
420 425 430

Glu Leu Val Ala Thr Ile Asn Arg Ile Gly Asn Ile Asn Tyr Gly Asp
435 440 445

Ser Val Lys Gly Arg Phe Thr Leu Ser Arg Glu Ile Ala Val Asn Thr
450 455 460

Val Tyr Leu Gln Met Asn Ser Leu Lys Pro Glu Asp Ala Ala Asn Tyr
465 470 475 480

Tyr Cys Tyr Ala Ala Lys Tyr Gly Val Asp Tyr Trp Gly Lys Gly Thr
485 490 495

Gln Val Thr Val Ser Ser
500

<210> SEQ ID NO 65
<211> LENGTH: 498
<212> TYPE: PRT
<213> ORGANISM: Artificial Sequence
<220> FEATURE:
<223> OTHER INFORMATION: MbNbB1c7HopQ MegaBody (CA15908)

<400> SEQUENCE: 65

Gln Val Gln Leu Val Glu Ser Gly Gly Gly Leu Val Gln Thr Lys Thr
1 5 10 15

Thr Thr Ser Val Ile Asp Thr Thr Asn Asp Ala Gln Asn Leu Leu Thr
20 25 30

Gln Ala Gln Thr Ile Val Asn Thr Leu Lys Asp Tyr Cys Pro Ile Leu
35 40 45

Ile Ala Lys Ser Ser Ser Ser Asn Gly Gly Thr Asn Asn Ala Asn Thr
50 55 60

Pro Ser Trp Gln Thr Ala Gly Gly Gly Lys Asn Ser Cys Ala Thr Phe
65 70 75 80

Gly Ala Glu Phe Ser Ala Ala Ser Asp Met Ile Asn Asn Ala Gln Lys
85 90 95

Ile Val Gln Glu Thr Gln Gln Leu Ser Ala Asn Gln Pro Lys Asn Ile
100 105 110

Thr Gln Pro His Asn Leu Asn Leu Asn Ser Pro Ser Ser Leu Thr Ala
115 120 125

Leu Ala Gln Lys Met Leu Lys Asn Ala Gln Ser Gln Ala Glu Ile Leu
130 135 140

Lys Leu Ala Asn Gln Val Glu Ser Asp Phe Asn Lys Leu Ser Ser Gly
145 150 155 160

His Leu Lys Asp Tyr Ile Gly Lys Cys Asp Ala Ser Ala Ile Ser Ser
165 170 175

Ala Asn Met Thr Met Gln Asn Gln Lys Asn Asn Trp Gly Asn Gly Cys
180 185 190

Ala Gly Val Glu Glu Thr Gln Ser Leu Leu Lys Thr Ser Ala Ala Asp
195 200 205

-continued

```
Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Thr Ala Ser Gly Phe Ser Leu
                405                 410                 415

Ser Ser Ser Tyr Met Asp Trp Val Arg Gln Ala Pro Gly Lys Gly Ile
            420                 425                 430

Glu Trp Val Ser Thr Ile Ser Pro Gly Gly Arg Ile Thr Tyr Ala Val
        435                 440                 445

Ser Val Glu Gly Arg Phe Thr Leu Ser Arg Asp Asn Ala Lys Asn Thr
    450                 455                 460

Leu Ser Leu Gln Met Asn Glu Leu Lys Pro Glu Asp Thr Ala Val Tyr
465                 470                 475                 480

Tyr Cys Arg Arg Leu Gly Glu Lys Gly Gln Gly Thr Gln Val Thr Val
                485                 490                 495

Ser Ser
```

<210> SEQ ID NO 66
<211> LENGTH: 502
<212> TYPE: PRT
<213> ORGANISM: Artificial Sequence
<220> FEATURE:
<223> OTHER INFORMATION: MbNbE1c7HopQ MegaBody (CA15909)

<400> SEQUENCE: 66

```
Gln Val Gln Leu Val Glu Ser Gly Gly Gly Leu Val Gln Thr Lys Thr
1               5                   10                  15

Thr Thr Ser Val Ile Asp Thr Thr Asn Asp Ala Gln Asn Leu Leu Thr
            20                  25                  30

Gln Ala Gln Thr Ile Val Asn Thr Leu Lys Asp Tyr Cys Pro Ile Leu
        35                  40                  45

Ile Ala Lys Ser Ser Ser Ser Asn Gly Gly Thr Asn Asn Ala Asn Thr
    50                  55                  60

Pro Ser Trp Gln Thr Ala Gly Gly Gly Lys Asn Ser Cys Ala Thr Phe
```

-continued

```
65                  70                  75                  80

Gly Ala Glu Phe Ser Ala Ala Ser Asp Met Ile Asn Asn Ala Gln Lys
                85                  90                  95

Ile Val Gln Glu Thr Gln Gln Leu Ser Ala Asn Gln Pro Lys Asn Ile
            100                 105                 110

Thr Gln Pro His Asn Leu Asn Leu Asn Ser Pro Ser Ser Leu Thr Ala
        115                 120                 125

Leu Ala Gln Lys Met Leu Lys Asn Ala Gln Ser Gln Ala Glu Ile Leu
    130                 135                 140

Lys Leu Ala Asn Gln Val Glu Ser Asp Phe Asn Lys Leu Ser Ser Gly
145                 150                 155                 160

His Leu Lys Asp Tyr Ile Gly Lys Cys Asp Ala Ser Ala Ile Ser Ser
                165                 170                 175

Ala Asn Met Thr Met Gln Asn Gln Lys Asn Asn Trp Gly Asn Gly Cys
            180                 185                 190

Ala Gly Val Glu Glu Thr Gln Ser Leu Leu Lys Thr Ser Ala Ala Asp
        195                 200                 205

Phe Asn Asn Gln Thr Pro Gln Ile Asn Gln Ala Gln Asn Leu Ala Asn
    210                 215                 220

Thr Leu Ile Gln Glu Leu Gly Asn Asn Thr Tyr Glu Gln Leu Ser Arg
225                 230                 235                 240

Leu Leu Thr Asn Asp Asn Gly Thr Asn Ser Lys Thr Ser Ala Gln Ala
                245                 250                 255

Ile Asn Gln Ala Val Asn Asn Leu Asn Glu Arg Ala Lys Thr Leu Ala
            260                 265                 270

Gly Gly Thr Thr Asn Ser Pro Ala Tyr Gln Ala Thr Leu Leu Ala Leu
        275                 280                 285

Arg Ser Val Leu Gly Leu Trp Asn Ser Met Gly Tyr Ala Val Ile Cys
    290                 295                 300

Gly Gly Tyr Thr Lys Ser Pro Gly Glu Asn Asn Gln Lys Asp Phe His
305                 310                 315                 320

Tyr Thr Asp Glu Asn Gly Asn Gly Thr Thr Ile Asn Cys Gly Gly Ser
                325                 330                 335

Thr Asn Ser Asn Gly Thr His Ser Tyr Asn Gly Thr Asn Thr Leu Lys
            340                 345                 350

Ala Asp Lys Asn Val Ser Leu Ser Ile Glu Gln Tyr Glu Lys Ile His
        355                 360                 365

Glu Ala Tyr Gln Ile Leu Ser Lys Ala Leu Lys Gln Ala Gly Leu Ala
    370                 375                 380

Pro Leu Asn Ser Lys Gly Glu Lys Leu Glu Ala His Val Thr Thr Ser
385                 390                 395                 400

Lys Tyr Gly Ser Leu Arg Leu Ser Cys Ala Ala Ser Gly Thr Ile Thr
                405                 410                 415

Arg Ser Pro Thr Met Ser Trp Ala Arg Gln Ala Pro Gly Arg Gln Arg
            420                 425                 430

Glu Trp Val Thr Ser Ile Leu Gly Thr Gly Arg Thr Asp Tyr Ala Asp
        435                 440                 445

Ser Val Lys Gly Arg Phe Thr Ile Ser Arg Asp Asn Ala Asn Asn Thr
    450                 455                 460

Val Tyr Leu Gln Met Asn Asn Leu Lys Pro Glu Asp Ser Ala Val Tyr
465                 470                 475                 480

Tyr Cys Tyr Thr Val Leu Asn Gly Arg Pro Ser Trp Gly Gln Gly Thr
                485                 490                 495
```

Gln Val Thr Val Ser Ser
500

<210> SEQ ID NO 67
<211> LENGTH: 886
<212> TYPE: PRT
<213> ORGANISM: Artificial Sequence
<220> FEATURE:
<223> OTHER INFORMATION: MbNbF3cYgjk_NO MegaBody

<400> SEQUENCE: 67

Gln Val Gln Leu Val Glu Ser Gly Gly Gly Leu Val Lys Glu Glu Thr
1 5 10 15

Gln Ser Gly Leu Asn Asn Tyr Ala Arg Val Val Glu Lys Gly Gln Tyr
20 25 30

Asp Ser Leu Glu Ile Pro Ala Gln Val Ala Ala Ser Trp Glu Ser Gly
35 40 45

Arg Asp Asp Ala Ala Val Phe Gly Phe Ile Asp Lys Glu Gln Leu Asp
50 55 60

Lys Tyr Val Ala Asn Gly Gly Lys Arg Ser Asp Trp Thr Val Lys Phe
65 70 75 80

Ala Glu Asn Arg Ser Gln Asp Gly Thr Leu Leu Gly Tyr Ser Leu Leu
85 90 95

Gln Glu Ser Val Asp Gln Ala Ser Tyr Met Tyr Ser Asp Asn His Tyr
100 105 110

Leu Ala Glu Met Ala Thr Ile Leu Gly Lys Pro Glu Glu Ala Lys Arg
115 120 125

Tyr Arg Gln Leu Ala Gln Gln Leu Ala Asp Tyr Ile Asn Thr Cys Met
130 135 140

Phe Asp Pro Thr Thr Gln Phe Tyr Tyr Asp Val Arg Ile Glu Asp Lys
145 150 155 160

Pro Leu Ala Asn Gly Cys Ala Gly Lys Pro Ile Val Glu Arg Gly Lys
165 170 175

Gly Pro Glu Gly Trp Ser Pro Leu Phe Asn Gly Ala Ala Thr Gln Ala
180 185 190

Asn Ala Asp Ala Val Val Lys Val Met Leu Asp Pro Lys Glu Phe Asn
195 200 205

Thr Phe Val Pro Leu Gly Thr Ala Ala Leu Thr Asn Pro Ala Phe Gly
210 215 220

Ala Asp Ile Tyr Trp Arg Gly Arg Val Trp Val Asp Gln Phe Trp Phe
225 230 235 240

Gly Leu Lys Gly Met Glu Arg Tyr Gly Tyr Arg Asp Asp Ala Leu Lys
245 250 255

Leu Ala Asp Thr Phe Phe Arg His Ala Lys Gly Leu Thr Ala Asp Gly
260 265 270

Pro Ile Gln Glu Asn Tyr Asn Pro Leu Thr Gly Ala Gln Gln Gly Ala
275 280 285

Pro Asn Phe Ser Trp Ser Ala Ala His Leu Tyr Met Leu Tyr Asn Asp
290 295 300

Phe Phe Arg Lys Gln Ala Ser Gly Gly Gly Ser Gly Gly Gly Gly Ser
305 310 315 320

Gly Gly Gly Gly Ser Gly Asn Ala Asp Asn Tyr Lys Asn Val Ile Asn
325 330 335

Arg Thr Gly Ala Pro Gln Tyr Met Lys Asp Tyr Asp Tyr Asp Asp His
340 345 350

```
Gln Arg Phe Asn Pro Phe Phe Asp Leu Gly Ala Trp His Gly His Leu
        355                 360                 365

Leu Pro Asp Gly Pro Asn Thr Met Gly Gly Phe Pro Gly Val Ala Leu
    370                 375                 380

Leu Thr Glu Glu Tyr Ile Asn Phe Met Ala Ser Asn Phe Asp Arg Leu
385                 390                 395                 400

Thr Val Trp Gln Asp Gly Lys Lys Val Asp Phe Thr Leu Glu Ala Tyr
                405                 410                 415

Ser Ile Pro Gly Ala Leu Val Gln Lys Leu Thr Ala Lys Asp Val Gln
            420                 425                 430

Val Glu Met Thr Leu Arg Phe Ala Thr Pro Arg Thr Ser Leu Leu Glu
        435                 440                 445

Thr Lys Ile Thr Ser Asn Lys Pro Leu Asp Leu Val Trp Asp Gly Glu
    450                 455                 460

Leu Leu Glu Lys Leu Glu Ala Lys Glu Gly Lys Pro Leu Ser Asp Lys
465                 470                 475                 480

Thr Ile Ala Gly Glu Tyr Pro Asp Tyr Gln Arg Lys Ile Ser Ala Thr
                485                 490                 495

Arg Asp Gly Leu Lys Val Thr Phe Gly Lys Val Arg Ala Thr Trp Asp
            500                 505                 510

Leu Leu Thr Ser Gly Glu Ser Glu Tyr Gln Val His Lys Ser Leu Pro
        515                 520                 525

Val Gln Thr Glu Ile Asn Gly Asn Arg Phe Thr Ser Lys Ala His Ile
    530                 535                 540

Asn Gly Ser Thr Thr Leu Tyr Thr Thr Tyr Ser His Leu Leu Thr Ala
545                 550                 555                 560

Gln Glu Val Ser Lys Glu Gln Met Gln Ile Arg Asp Ile Leu Ala Arg
                565                 570                 575

Pro Ala Phe Tyr Leu Thr Ala Ser Gln Gln Arg Trp Glu Glu Tyr Leu
            580                 585                 590

Lys Lys Gly Leu Thr Asn Pro Asp Ala Thr Pro Glu Gln Thr Arg Val
        595                 600                 605

Ala Val Lys Ala Ile Glu Thr Leu Asn Gly Asn Trp Arg Ser Pro Gly
    610                 615                 620

Gly Ala Val Lys Phe Asn Thr Val Thr Pro Ser Val Thr Gly Arg Trp
625                 630                 635                 640

Phe Ser Gly Asn Gln Thr Trp Pro Trp Asp Thr Trp Lys Gln Ala Phe
                645                 650                 655

Ala Met Ala His Phe Asn Pro Asp Ile Ala Lys Glu Asn Ile Arg Ala
            660                 665                 670

Val Phe Ser Trp Gln Ile Gln Pro Gly Asp Ser Val Arg Pro Gln Asp
        675                 680                 685

Val Gly Phe Val Pro Asp Leu Ile Ala Trp Asn Leu Ser Pro Glu Arg
    690                 695                 700

Gly Gly Asp Gly Gly Asn Trp Asn Glu Arg Asn Thr Lys Pro Ser Leu
705                 710                 715                 720

Ala Ala Trp Ser Val Met Glu Val Tyr Asn Val Thr Gln Asp Lys Thr
                725                 730                 735

Trp Val Ala Glu Met Tyr Pro Lys Leu Val Ala Tyr His Asp Trp Trp
            740                 745                 750

Leu Arg Asn Arg Asp His Asn Gly Asn Gly Val Pro Glu Tyr Gly Ala
        755                 760                 765
```

```
Thr Arg Asp Lys Ala His Asn Thr Glu Ser Gly Glu Met Leu Phe Thr
    770                 775                 780

Val Lys Lys Ser Leu Arg Leu Ser Cys Ala Ala Ser Gly Ser Gly Phe
785                 790                 795                 800

Gly Pro Asn Val Met Gly Trp Tyr Arg Gln Ala Pro Gly Lys Arg Arg
                805                 810                 815

Glu Leu Val Ala Thr Ile Asn Arg Ile Gly Asn Ile Asn Tyr Gly Asp
            820                 825                 830

Ser Val Lys Gly Arg Phe Thr Leu Ser Arg Glu Ile Ala Val Asn Thr
        835                 840                 845

Val Tyr Leu Gln Met Asn Ser Leu Lys Pro Glu Asp Ala Ala Asn Tyr
    850                 855                 860

Tyr Cys Tyr Ala Ala Lys Tyr Gly Val Asp Tyr Trp Gly Lys Gly Thr
865                 870                 875                 880

Gln Val Thr Val Ser Ser
                885


<210> SEQ ID NO 68
<211> LENGTH: 278
<212> TYPE: PRT
<213> ORGANISM: Artificial Sequence
<220> FEATURE:
<223> OTHER INFORMATION: MSP1E1D3

<400> SEQUENCE: 68

Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Leu Asp Asp Phe Gln Lys Lys Trp Gln
    130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240
```

-continued

Lys Ala Lys Pro Ala Leu Glu Asp Leu Arg Gln Gly Leu Leu Pro Val
245 250 255

Leu Glu Ser Phe Lys Val Ser Phe Leu Ser Ala Leu Glu Glu Tyr Thr
260 265 270

Lys Lys Leu Asn Thr Gln
275

<210> SEQ ID NO 69
<211> LENGTH: 267
<212> TYPE: PRT
<213> ORGANISM: Homo sapiens

<400> SEQUENCE: 69

Met Lys Ala Ala Val Leu Thr Leu Ala Val Leu Phe Leu Thr Gly Ser
1 5 10 15

Gln Ala Arg His Phe Trp Gln Gln Asp Glu Pro Pro Gln Ser Pro Trp
20 25 30

Asp Arg Val Lys Asp Leu Ala Thr Val Tyr Val Asp Val Leu Lys Asp
35 40 45

Ser Gly Arg Asp Tyr Val Ser Gln Phe Glu Gly Ser Ala Leu Gly Lys
50 55 60

Gln Leu Asn Leu Lys Leu Leu Asp Asn Trp Asp Ser Val Thr Ser Thr
65 70 75 80

Phe Ser Lys Leu Arg Glu Gln Leu Gly Pro Val Thr Gln Glu Phe Trp
85 90 95

Asp Asn Leu Glu Lys Glu Thr Glu Gly Leu Arg Gln Glu Met Ser Lys
100 105 110

Asp Leu Glu Glu Val Lys Ala Lys Val Gln Pro Tyr Leu Asp Asp Phe
115 120 125

Gln Lys Lys Trp Gln Glu Glu Met Glu Leu Tyr Arg Gln Lys Val Glu
130 135 140

Pro Leu Arg Ala Glu Leu Gln Glu Gly Ala Arg Gln Lys Leu His Glu
145 150 155 160

Leu Gln Glu Lys Leu Ser Pro Leu Gly Glu Glu Met Arg Asp Arg Ala
165 170 175

Arg Ala His Val Asp Ala Leu Arg Thr His Leu Ala Pro Tyr Ser Asp
180 185 190

Glu Leu Arg Gln Arg Leu Ala Ala Arg Leu Glu Ala Leu Lys Glu Asn
195 200 205

Gly Gly Ala Arg Leu Ala Glu Tyr His Ala Lys Ala Thr Glu His Leu
210 215 220

Ser Thr Leu Ser Glu Lys Ala Lys Pro Ala Leu Glu Asp Leu Arg Gln
225 230 235 240

Gly Leu Leu Pro Val Leu Glu Ser Phe Lys Val Ser Phe Leu Ser Ala
245 250 255

Leu Glu Glu Tyr Thr Lys Lys Leu Asn Thr Gln
260 265

<210> SEQ ID NO 70
<211> LENGTH: 408
<212> TYPE: PRT
<213> ORGANISM: Artificial Sequence
<220> FEATURE:
<223> OTHER INFORMATION: circular permutated HopQ (cHopQ)

<400> SEQUENCE: 70

Thr Lys Thr Thr Thr Ser Val Ile Asp Thr Thr Asn Asp Ala Gln Asn

-continued

```
1               5                   10                  15

Leu Leu Thr Gln Ala Gln Thr Ile Val Asn Thr Leu Lys Asp Tyr Cys
            20                  25                  30

Pro Ile Leu Ile Ala Lys Ser Ser Ser Ser Asn Gly Gly Thr Asn Asn
        35                  40                  45

Ala Asn Thr Pro Ser Trp Gln Thr Ala Gly Gly Gly Lys Asn Ser Cys
    50                  55                  60

Ala Thr Phe Gly Ala Glu Phe Ser Ala Ala Ser Asp Met Ile Asn Asn
65                  70                  75                  80

Ala Gln Lys Ile Val Gln Glu Thr Gln Gln Leu Ser Ala Asn Gln Pro
                85                  90                  95

Lys Asn Ile Thr Gln Pro His Asn Leu Asn Leu Asn Ser Pro Ser Ser
            100                 105                 110

Leu Thr Ala Leu Ala Gln Lys Met Leu Lys Asn Ala Gln Ser Gln Ala
        115                 120                 125

Glu Ile Leu Lys Leu Ala Asn Gln Val Glu Ser Asp Phe Asn Lys Leu
    130                 135                 140

Ser Ser Gly His Leu Lys Asp Tyr Ile Gly Lys Cys Asp Ala Ser Ala
145                 150                 155                 160

Ile Ser Ser Ala Asn Met Thr Met Gln Asn Gln Lys Asn Asn Trp Gly
                165                 170                 175

Asn Gly Cys Ala Gly Val Glu Glu Thr Gln Ser Leu Leu Lys Thr Ser
            180                 185                 190

Ala Ala Asp Phe Asn Asn Gln Thr Pro Gln Ile Asn Gln Ala Gln Asn
        195                 200                 205

Leu Ala Asn Thr Leu Ile Gln Glu Leu Gly Asn Asn Pro Phe Arg Ala
    210                 215                 220

Ser Gly Gly Gly Ser Gly Gly Gly Gly Ser Gly Lys Leu Ser Asp Thr
225                 230                 235                 240

Tyr Glu Gln Leu Ser Arg Leu Leu Thr Asn Asp Asn Gly Thr Asn Ser
                245                 250                 255

Lys Thr Ser Ala Gln Ala Ile Asn Gln Ala Val Asn Asn Leu Asn Glu
            260                 265                 270

Arg Ala Lys Thr Leu Ala Gly Gly Thr Thr Asn Ser Pro Ala Tyr Gln
        275                 280                 285

Ala Thr Leu Leu Ala Leu Arg Ser Val Leu Gly Leu Trp Asn Ser Met
    290                 295                 300

Gly Tyr Ala Val Ile Cys Gly Gly Tyr Thr Lys Ser Pro Gly Glu Asn
305                 310                 315                 320

Asn Gln Lys Asp Phe His Tyr Thr Asp Glu Asn Gly Asn Gly Thr Thr
                325                 330                 335

Ile Asn Cys Gly Gly Ser Thr Asn Ser Asn Gly Thr His Ser Tyr Asn
            340                 345                 350

Gly Thr Asn Thr Leu Lys Ala Asp Lys Asn Val Ser Leu Ser Ile Glu
        355                 360                 365

Gln Tyr Glu Lys Ile His Glu Ala Tyr Gln Ile Leu Ser Lys Ala Leu
    370                 375                 380

Lys Gln Ala Gly Leu Ala Pro Leu Asn Ser Lys Gly Glu Lys Leu Glu
385                 390                 395                 400

Ala His Val Thr Thr Ser Lys Tyr
                405
```

<210> SEQ ID NO 71

<211> LENGTH: 389
<212> TYPE: PRT
<213> ORGANISM: Artificial Sequence
<220> FEATURE:
<223> OTHER INFORMATION: circular permutated HopQ wherein the linker and
      7 amino acids are truncated(c7HopQ)

<400> SEQUENCE: 71

```
Thr Lys Thr Thr Thr Ser Val Ile Asp Thr Thr Asn Asp Ala Gln Asn
1               5                   10                  15

Leu Leu Thr Gln Ala Gln Thr Ile Val Asn Thr Leu Lys Asp Tyr Cys
            20                  25                  30

Pro Ile Leu Ile Ala Lys Ser Ser Ser Ser Asn Gly Gly Thr Asn Asn
        35                  40                  45

Ala Asn Thr Pro Ser Trp Gln Thr Ala Gly Gly Gly Lys Asn Ser Cys
    50                  55                  60

Ala Thr Phe Gly Ala Glu Phe Ser Ala Ala Ser Asp Met Ile Asn Asn
65                  70                  75                  80

Ala Gln Lys Ile Val Gln Glu Thr Gln Gln Leu Ser Ala Asn Gln Pro
                85                  90                  95

Lys Asn Ile Thr Gln Pro His Asn Leu Asn Leu Asn Ser Pro Ser Ser
            100                 105                 110

Leu Thr Ala Leu Ala Gln Lys Met Leu Lys Asn Ala Gln Ser Gln Ala
        115                 120                 125

Glu Ile Leu Lys Leu Ala Asn Gln Val Glu Ser Asp Phe Asn Lys Leu
    130                 135                 140

Ser Ser Gly His Leu Lys Asp Tyr Ile Gly Lys Cys Asp Ala Ser Ala
145                 150                 155                 160

Ile Ser Ser Ala Asn Met Thr Met Gln Asn Gln Lys Asn Asn Trp Gly
                165                 170                 175

Asn Gly Cys Ala Gly Val Glu Glu Thr Gln Ser Leu Leu Lys Thr Ser
            180                 185                 190

Ala Ala Asp Phe Asn Asn Gln Thr Pro Gln Ile Asn Gln Ala Gln Asn
        195                 200                 205

Leu Ala Asn Thr Leu Ile Gln Glu Leu Gly Asn Asn Thr Tyr Glu Gln
    210                 215                 220

Leu Ser Arg Leu Leu Thr Asn Asp Asn Gly Thr Asn Ser Lys Thr Ser
225                 230                 235                 240

Ala Gln Ala Ile Asn Gln Ala Val Asn Asn Leu Asn Glu Arg Ala Lys
                245                 250                 255

Thr Leu Ala Gly Gly Thr Thr Asn Ser Pro Ala Tyr Gln Ala Thr Leu
            260                 265                 270

Leu Ala Leu Arg Ser Val Leu Gly Leu Trp Asn Ser Met Gly Tyr Ala
        275                 280                 285

Val Ile Cys Gly Gly Tyr Thr Lys Ser Pro Gly Glu Asn Asn Gln Lys
    290                 295                 300

Asp Phe His Tyr Thr Asp Glu Asn Gly Asn Gly Thr Thr Ile Asn Cys
305                 310                 315                 320

Gly Gly Ser Thr Asn Ser Asn Gly Thr His Ser Tyr Asn Gly Thr Asn
                325                 330                 335

Thr Leu Lys Ala Asp Lys Asn Val Ser Leu Ser Ile Glu Gln Tyr Glu
            340                 345                 350

Lys Ile His Glu Ala Tyr Gln Ile Leu Ser Lys Ala Leu Lys Gln Ala
        355                 360                 365
```

-continued

```
Gly Leu Ala Pro Leu Asn Ser Lys Gly Glu Lys Leu Glu Ala His Val
    370                 375                 380

Thr Thr Ser Lys Tyr
385
```